US009927396B2

(12) United States Patent
Peterson et al.

(10) Patent No.: US 9,927,396 B2
(45) Date of Patent: Mar. 27, 2018

(54) CAPILLARY ELECTROPHORESIS-ELECTROSPRAY IONIZATION-MASS SPECTROMETRY SYSTEM

(71) Applicant: Beckman Coulter, Inc., Brea, CA (US)

(72) Inventors: Brian D. Peterson, Ontario, CA (US); Dale Alan Owens, Corona, CA (US); Peter S. Kotowski, Yorba Linda, CA (US); Sunil S. Deliwala, Placentia, CA (US); Craig A. Hudson, Brownsburg, IN (US); James H. Reyes, Victoville, CA (US); Clive Cheung, Norco, CA (US); Tom Tran, Irvine, CA (US); Anna X. Lou, Arcadia, CA (US); Jane Luo, Irvine, CA (US); Jean-Marc Rene Lucien Busnel, Marseille (FR); Chitra K. Ratnayake, Yorba Linda, CA (US)

(73) Assignee: DH Technologies Development Pte. Ltd., Singapore (SG)

(*) Notice: Subject to any disclaimer, the term of this patent is extended or adjusted under 35 U.S.C. 154(b) by 556 days.

(21) Appl. No.: 14/354,489

(22) PCT Filed: Oct. 26, 2012

(86) PCT No.: PCT/US2012/062270
§ 371 (c)(1),
(2) Date: Apr. 25, 2014

(87) PCT Pub. No.: WO2013/063502
PCT Pub. Date: May 2, 2013

(65) Prior Publication Data
US 2014/0305801 A1    Oct. 16, 2014

Related U.S. Application Data

(60) Provisional application No. 61/552,411, filed on Oct. 27, 2011.

(51) Int. Cl.
*G01N 27/447* (2006.01)
*G01N 30/72* (2006.01)
(Continued)

(52) U.S. Cl.
CPC . *G01N 27/44743* (2013.01); *G01N 27/44717* (2013.01); *G01N 30/7266* (2013.01);
(Continued)

(58) Field of Classification Search
CPC ............ G01N 30/7266; G01N 27/447; G01N 27/44708; G01N 27/44743; H01J 49/167
See application file for complete search history.

(56) References Cited

U.S. PATENT DOCUMENTS 5,164,064 A * 11/1992 Dill .................. G01N 27/44708
                                                                    204/601
6,127,680 A * 10/2000 Andrien, Jr. .......... H01J 49/167
                                                                    250/281
(Continued)

*Primary Examiner* — Luan Van
*Assistant Examiner* — Steven E Rosenwald

(57) ABSTRACT

Aspects of the innovations presented herein relate to improved systems that in some embodiments perform capillary electrophoresis (CE) and CE in conjunction with electrospray ionization (ESI) as an input to a mass spectrometry system (MS). Some embodiments use a high voltage isolated CE power supply that is configured to float on the high voltage output of an ESI-MS power supply, with a protective resistance in the ESI-MS path, as well as DC/DC converter isolation and communication system isolation for the isolated CE power supply. Some embodiments additionally use a cartridge assembly integrating separation and conductive fluid capillaries with fluid cooling and protective retractable housings for the capillary end portions and for the ESI output. The protective housing may further be used with an adapter for interfacing with different MS systems.

19 Claims, 30 Drawing Sheets

(51) Int. Cl.
*H01J 49/02* (2006.01)
*H01J 49/16* (2006.01)

(52) U.S. Cl.
CPC .......... *H01J 49/022* (2013.01); *H01J 49/165* (2013.01); *Y10T 307/313* (2015.04)

(56) References Cited

U.S. PATENT DOCUMENTS

| | | | | |
|---|---|---|---|---|
| 2001/0040096 | A1* | 11/2001 | Yamamoto | G01N 27/44782 204/604 |
| 2004/0075050 | A1* | 4/2004 | Rossier | H01J 49/42 250/288 |
| 2006/0285999 | A1* | 12/2006 | Timperman | B01L 3/502746 422/400 |
| 2007/0068872 | A1* | 3/2007 | Gerhardt | B01L 3/565 210/656 |
| 2008/0038152 | A1* | 2/2008 | Van Pelt | B01L 3/565 285/384 |
| 2009/0263290 | A1* | 10/2009 | Yang | G01N 35/1065 422/400 |

* cited by examiner

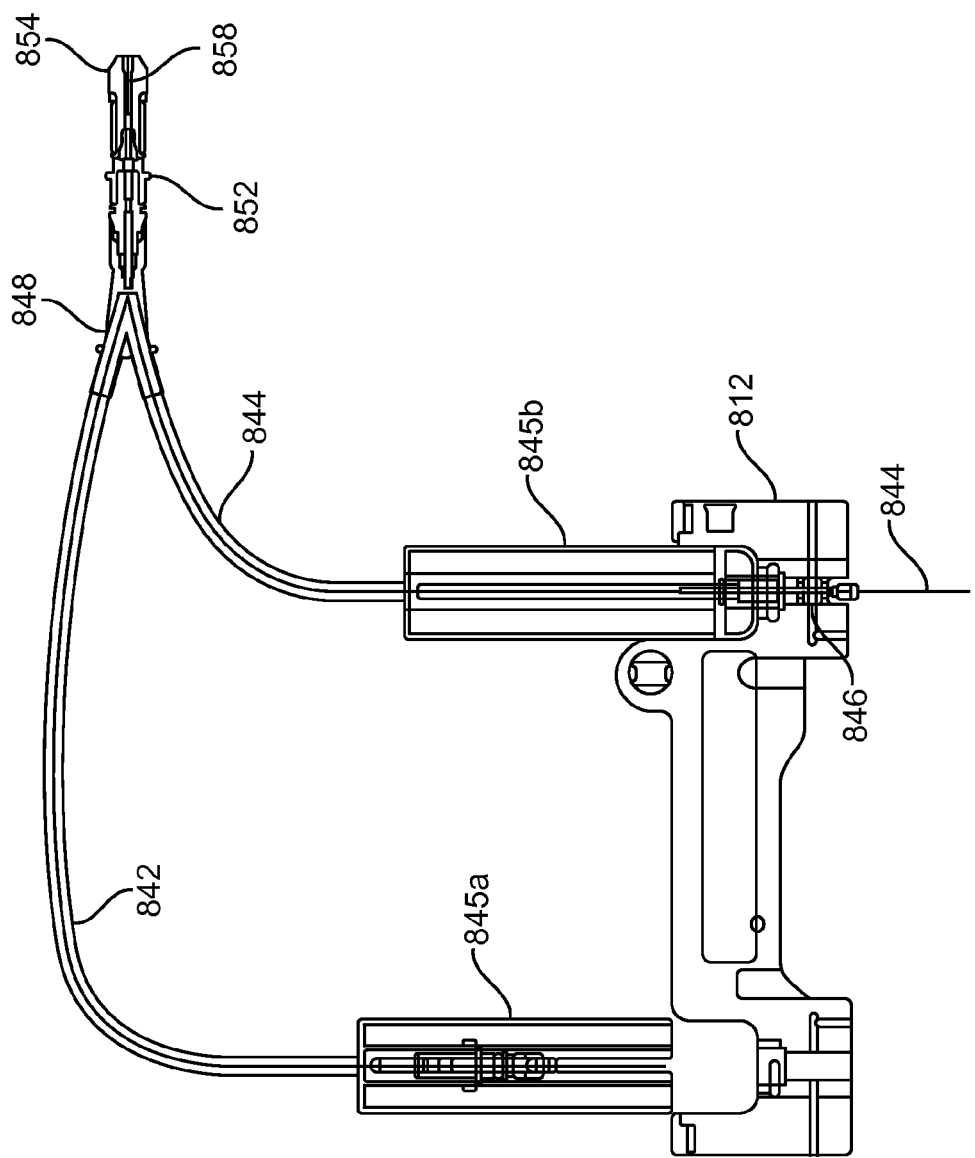

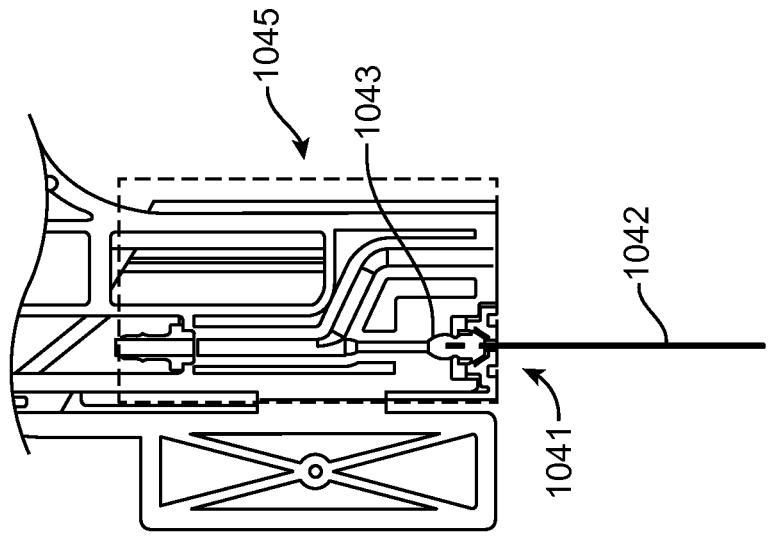
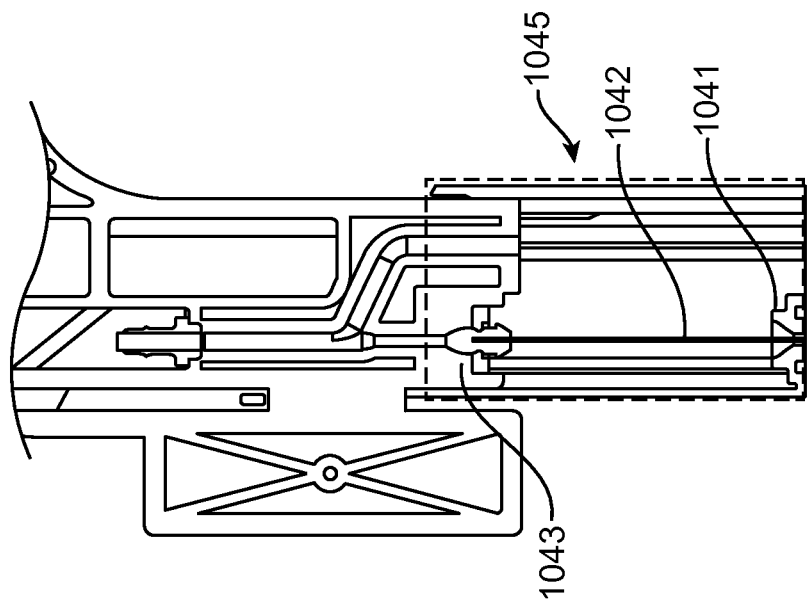
FIG. 10A
FIG. 10B

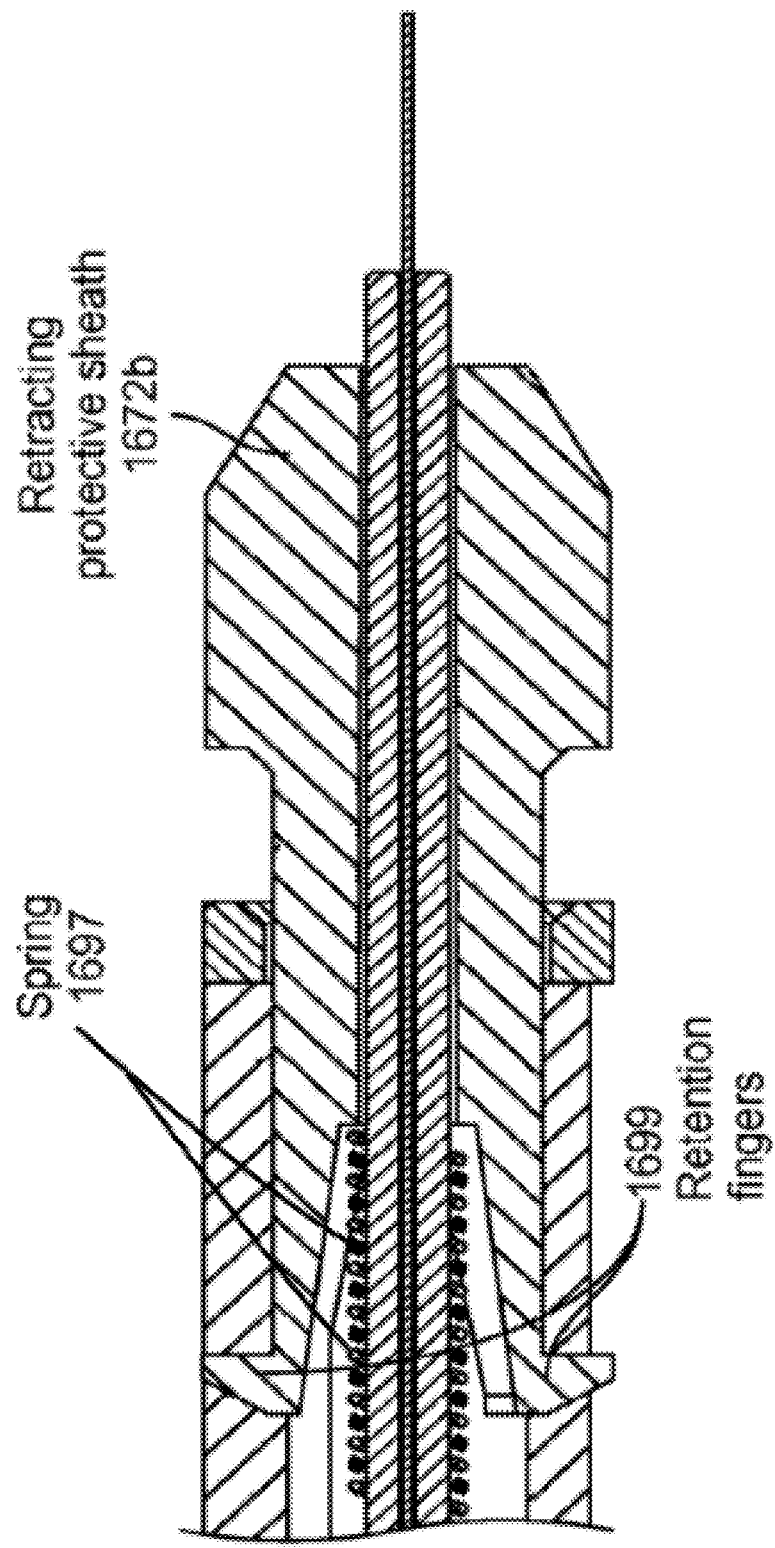

CAPILLARY ELECTROPHORESIS-ELECTROSPRAY IONIZATION-MASS SPECTROMETRY SYSTEM

RELATED APPLICATIONS

This application claims the benefit of U.S. Patent Application Ser. No. 61/552,411, filed Oct. 27, 2011, the content of which is incorporated by reference herein in its entirety.

BACKGROUND

This invention relates to electrophoresis and to capillary electrophoresis used in conjunction with electrospray ionization mass spectrometry.

Electrophoresis is fundamentally the movement of charged particles within an applied electric field. Capillary electrophoresis (CE) is a known process. In capillary electrophoresis, a sample is injected at one end of the capillary. A detector is attached on the capillary at the other end of the capillary distant from the sample. A voltage is applied along the length of the capillary.

With the electric potential applied, two separate flow effects occur. The first of these flow effects is a gross sample flow effect. The sample moves as a mass into the capillary. The second of these flow effects is the electrophoretic flow. This causes the constituents of the sample having differing electric charge to move relative to the main stream of fluid within the capillary. The portions of the sample having differing electric charges are thereby separated in the capillary.

Different detectors may be used to analyze the sample after the separation has occurred. In a system that combines capillary electrophoresis with electrospray ionization (ESI), and mass spectrometry (MS), the output of the capillary is input to an electrospray assembly. The electrospray ionization is accomplished by placing a high voltage potential at the outlet of the separation capillary with respect to the capillary inlet to the mass spectrometer. The separation capillary also requires a high voltage potential placed between its inlet and outlet. The separated portions of the sample are dispersed by the electrospray into a fine aerosol as they exit the capillary. The droplets of the aerosol then are observed by mass spectrometry.

Capillary electrophoresis coupled with electrospray ionization and mass spectrometry is a relatively difficult procedure. The capillary must be mechanically connected to the rest of the system and positioned with respect to a detector. The capillaries are small and fragile, and the alignment process with the electrospray ionization assembly into the mass spectrometer may be difficult, time consuming, and may damage the capillary.

The system is further complicated by the need to cool the capillary. This cooling is required because the small capillary is subject to electrical resistance heating during the period of time electrophoresis potential voltage is applied. A small current under high voltage flowing in the capillary generates heat. The cooling is required to prevent damage to the capillary and to prevent variations in temperature during analysis of the sample from impacting the results of the analysis. Excess heat may cause diffusion of the separated portions of the sample that migrate through the capillary at different speeds. The heat and its resultant diffusion degrade separation and following classification result that is the purpose of using electrophoresis.

FIG. 2A describes a known CE-MS system using a CE power supply 220a that is not isolated. This configuration may also be considered a non-floating configuration, where the high voltage from CE power supply 220a used to create separation in the sample capillary 242a has the same ground as the ESI-MS power supply 254 that is used by mass spectrometer 250. Using non-isolated (non-floating) power supplies requires that the return path, which is the path that the current from the DC power supply output follows to return to the power supply input, for both separation and electrospray power supplies are ground referenced. This presents a problem in that the separation power supply return creates an electrical short circuit for the electrospray power supply. This is seen in FIG. 2A in the connection from electrospray (ES) High Voltage Output 226 through Conductive Fluid Capillary 244a to CE High Voltage (HV) return 224a.

To alleviate this problem, one known approach is to have the high voltage return for the separation power supply disconnected. In FIG. 2A, this may be shown as disconnecting the direct path from conductive fluid vial 234a to CE Power Supply 220a. This changes the return path for CE Power Supply 220a, and then requires that current generated by the separation supply not only pass through the sample capillary 242a but also the electrospray assembly 252a, the mass spectrometer ESI-MS Power Supply 254, and the instrument chassis ground before finding its return to CE power supply 220a at CE HV return 224a. Although such a method provides the functionality for CE-ESI-MS, if the separation power supply requires current to return through a dedicated pin rather than chassis ground, a false current leakage reading may be induced. Furthermore, current measurements for the electrospray power supply will reflect the sum of both ESI and separation current. Because the separation current is typically one to two orders of magnitude greater than the electrospray current, the electrospray current cannot be determined for system diagnostic purposes.

Another alternative solution involves placing the electrospray needle or separation capillary outlet at ground potential. This may work with the operation of the CE-ESI-MS system but requires the inlet of the mass spectrometer to be at high voltage potentials. This complicates the design of the mass spectrometer.

Therefore, other alternative solutions to the problems presented by a non-isolated power supply may avoid the drawbacks of the known alternatives. Additionally, while systems and methods of using capillary electrophoresis with electrospray ionization and mass spectrometry are known, as described above, modifications to current systems as presented herein improve the ease of use, performance, and electrical functionality of these systems.

SUMMARY

The innovations presented herein relate to an improved system where capillary electrophoresis is used in conjunction with electrospray ionization mass spectrometry. In one potential implementation, a capillary electrophoresis electrospray ionization mass spectrometry (CE-ESI-MS) system is disclosed that comprises a mass spectrometry (MS) dc power supply having a first output and a first input and an isolated capillary electrophoresis (CE) dc power supply having a second output and a second input. A MS electrical path connected to a ground provides a mass spectrometry dc power supply return from the first output to the first input via a mass spectrometry load, and a CE electrical path provides a CE dc power supply return from the second output to the second input via a separation capillary. The second resistive electrical path in this system is isolated from ground and the first output is electrically coupled with the second input. The system finally includes a control circuit that is electrically coupled with the isolated CE dc power supply and is isolated from ground and a DC/DC converter that provides isolated input power to the second dc power supply and the isolated control circuit.

In further alternative embodiments, the CE-ESI-MS system comprises a voltage limit resistor coupled directly to the MS dc power supply and that is in the MS electrical path and is not in the CE electrical path, or a system wherein the control circuit is communicatively coupled with an interface board via a communication link, wherein the communication link maintains the isolation from the ground. In some of such additional embodiments, the communication link is selected for being capable of withstanding a voltage greater than or equal to the maximum output voltage of the MS or CE dc power supplies. In some embodiments, the relevant voltages include those whereby the maximum output voltage of the MS dc power supply is a voltage value between −10 kV and +10 kV (inclusive), and the maximum output voltage of the CE dc power supply is a voltage value between −30kV and +30 kV (inclusive). In some embodiments, other voltage ranges are appropriate depending on other variables in the system.

In certain embodiments the communication link comprises an optical fiber link, while in other embodiments, the link comprises a wireless link, such that the floating control circuit communicates with another circuit that is operating referenced to a ground potential without damaging either itself or the other component.

In additional embodiments according to an improved CE-ESI-MS system, a cartridge for use with a CE-ESI-MS system comprises both a protective sheath, configured to be coupled with the cartridge and capable of extending from and retracting with respect to a housing of the cartridge, and a capillary coupled with the protective sheath. In some embodiments, such a system is additionally a system wherein the sheath is a first sheath, the capillary is a first capillary, and wherein the cartridge comprises both a second sheath, capable of extending from and retracting with respect to the housing of the cartridge, and a second capillary coupled with the second protective sheath. In some embodiments a cartridge assembly further comprises first and second cooling tubes respectively surrounding a portion of the first and second capillaries, wherein the first and second cooling tubes are configured to contain a cooling fluid, and some embodiments include a system wherein the cooling fluid circulates in the first and second tubes in a cooling circuit.

Additional embodiments include systems comprising a cartridge assembly including a cartridge having a housing, a protective sheath configured to be coupled with the cartridge and capable of extending from and retracting with respect to the housing of the cartridge, a capillary coupled with the protective sheath, a sprayer housing comprising a first electrical contact coupled with the capillary; an adapter comprising a second electrical contact, wherein the first electrical contact is configured to contact the second electrical contact.

In one potential alternative embodiment, a cartridge assembly comprises a separation capillary, a first tube that surrounds at least a middle portion of the separation capillary, a cartridge having a first protective sheath that is adjustable from an extended position to a retracted position; and a sprayer housing. In some of such embodiments the first tube and the separation capillary enter a first opening of the cartridge at a first position along the separation capillary where the first tube surrounds the at least a middle portion of the separation capillary; in some of such embodiments, a first end portion of the capillary that is not surrounded by the first tube is covered by the first protective sheath when the first protective sheath is in an extended position, and in some of such embodiments the first end portion of the separation capillary extends through a first capillary interface as the first protective sheath is adjusted from the extended position to the retracted position such that the first end portion of the separation capillary protrudes from the cartridge to an extent sufficient to enter a CE vial. Additionally, in some embodiments, a second end portion of the separation capillary opposite the first end portion of the separation capillary extends through an electrospray needle in the sprayer housing, and the middle portion of the first capillary surrounded by the tube ends at an entrance to the sprayer housing.

In some embodiments, the system further includes a conductive fluid capillary and a second tube that surrounds at least a middle portion of the conductive fluid capillary, where the cartridge has a second protective sheath that is adjustable from an extended position to a retracted position, and the second tube and the conductive fluid capillary enter a second opening of the cartridge at a second position along the conductive fluid capillary where the second tube surrounds the at least a middle portion of the conductive fluid capillary. Additionally, a first end portion of the conductive fluid capillary that is not surrounded by the second tube is covered by the second protective sheath when the second protective sheath is in the extended position, and in some embodiments the first end portion of the conductive fluid capillary extends through a second capillary interface as the second protective sheath is adjusted from the extended position to the retracted position, such that the first end portion of the conductive fluid capillary protrudes from the cartridge to an extent sufficient to enter a conductive fluid vial. Finally, a second end portion of the conductive fluid capillary opposite the first end portion of the conductive fluid capillary extends into a double lumen tube and the double lumen tube is positioned in a central space in the sprayer housing and extends along a portion of the separation capillary that extends through the sprayer housing.

BRIEF DESCRIPTION OF THE DRAWINGS

FIG. 8 illustrates a cartridge assembly that is used as part of a CE-ESI mass spectrometry system in accordance with one potential embodiment of the innovations presented herein.

FIG. 10A illustrates a portion of a cartridge assembly including a capillary protection cover (sheath in extended position) that is used as part of a CE-ESI mass spectrometry system in accordance with one potential embodiment of the innovations presented herein.

FIG. 10B illustrates a portion of a cartridge assembly including a capillary protection cover (sheath in retracted position) that is used as part of a CE-ESI mass spectrometry system in accordance with one potential embodiment of the innovations presented herein.

FIG. 16C illustrates an electrospray assembly that is used as part of a CE-ESI mass spectrometry system in accordance with one potential embodiment of the innovations presented herein.

DETAILED DESCRIPTION OF THE INVENTION

The innovations presented herein relate to improved systems and methods integrating capillary electrophoresis (CE) with mass spectrometry (MS). In some embodiments such a system provides an integrated structure that as a whole is used to separate samples containing molecules such as protein complexes, proteins, peptides, glycans or drugs and/or metabolites using CE and to characterize and/or identify the separated molecules using MS. The innovations herein, in certain embodiments, apply to any capillary electrophoresis (CE) system coupled with a mass spectrometer (MS) system via electrospray ionization (ESI), and also apply to any MS system.

Figure 1:
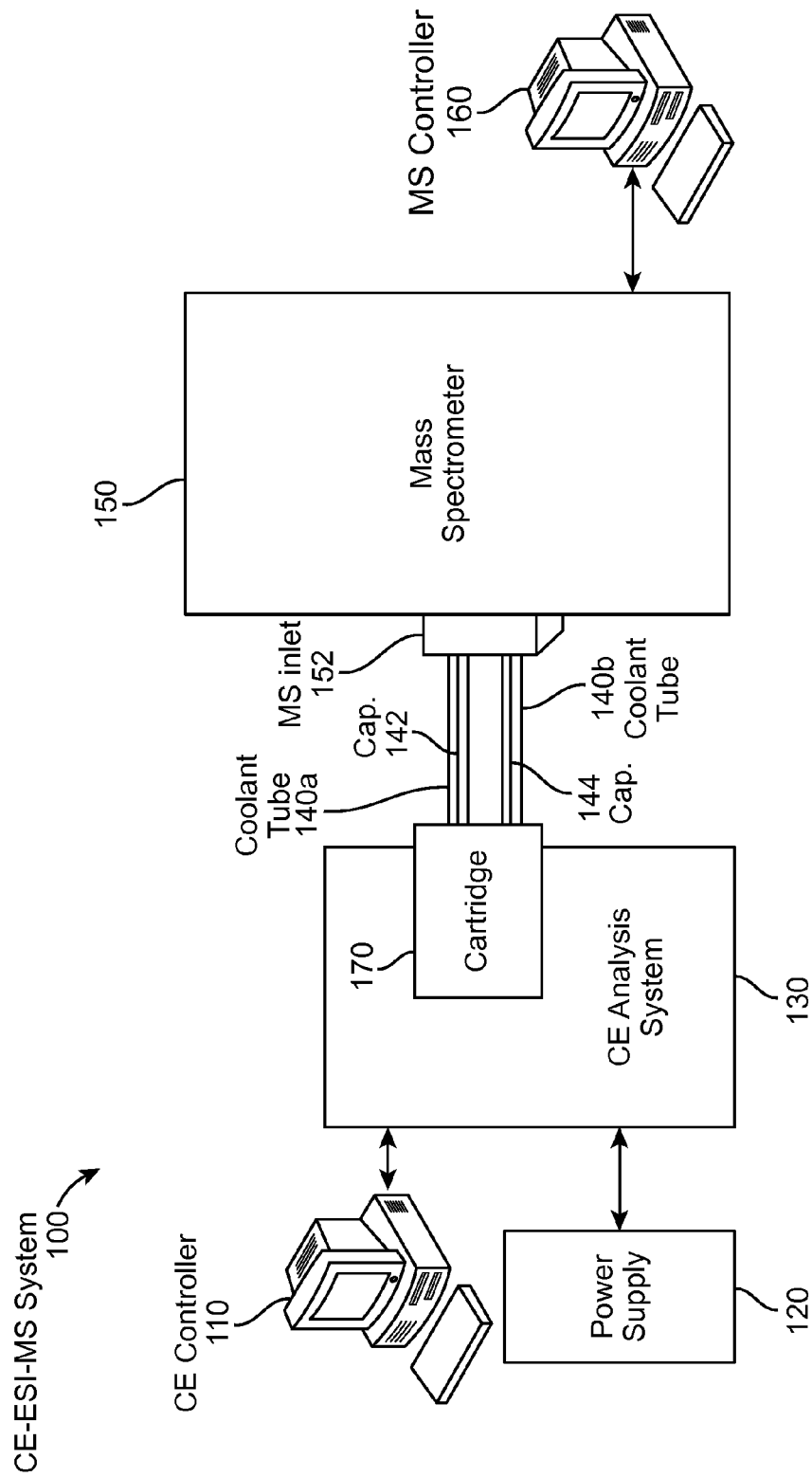
FIG. 1 illustrates a diagram of one potential implementation of a CE-ESI mass spectrometry system in accordance with one potential embodiment of the innovations presented herein.

FIG. 1 describes an overall system for CE-ESI-MS according to one potential embodiment of the innovations described herein. CE-ESI-MS system 100 includes a capillary electrophoresis (CE) controller 110, a power supply 120, a capillary electrophoresis analysis system 130, a cartridge 170, coolant tubes 140a and 140b, capillaries 142 and 144, mass spectrometer inlet 152, mass spectrometer 150, and mass spectrometer controller 160.

The basic functionality of the system is for a sample to be selected and introduced to the inlet of separation capillary 142 of FIG. 1 by CE analysis system 130. Power supply 120 provides a high voltage, which in some embodiments is on the order of 30 kV, across separation capillary 142. Conductive fluid capillary 144 introduces a conductive fluid at a sprayer housing attached to MS inlet 152 to enable ESI of the separated material where, in some embodiments, a mass spectrometer 150 then analyzes the separated sample. Coolant tube 140a cools separation capillary 142 and carries a coolant to the sprayer housing. Coolant tube 140b returns the coolant to the CE analysis system 130. Both capillaries are threaded through the coolant tubes such that the tubes, and the coolant carried by the tubes, surround a portion of the capillaries.

Power supply 120 comprises, in some embodiments, an isolated power supply as described below. In some embodiments, CE analysis system 130 comprises any device that functions to manage and implement CE separation of sample materials, along with any other tests on the materials that in some embodiments are done concurrently or as part of the same system. As one non-limiting example, CE analysis system 130 comprises a Beckman Coulter PA800 Pharmaceutical Analysis System™.

In some embodiments cartridge 170 comprises a removable, replaceable cartridge that is integrated with coolant tubes 140a and 140b, as well as capillaries 142 and 144, and a sprayer housing (that is not shown but is discussed below) to form integrated components of a cartridge assembly which connects to the mass spectrometer 150 at mass spectrometer inlet 152.

Figure 20:
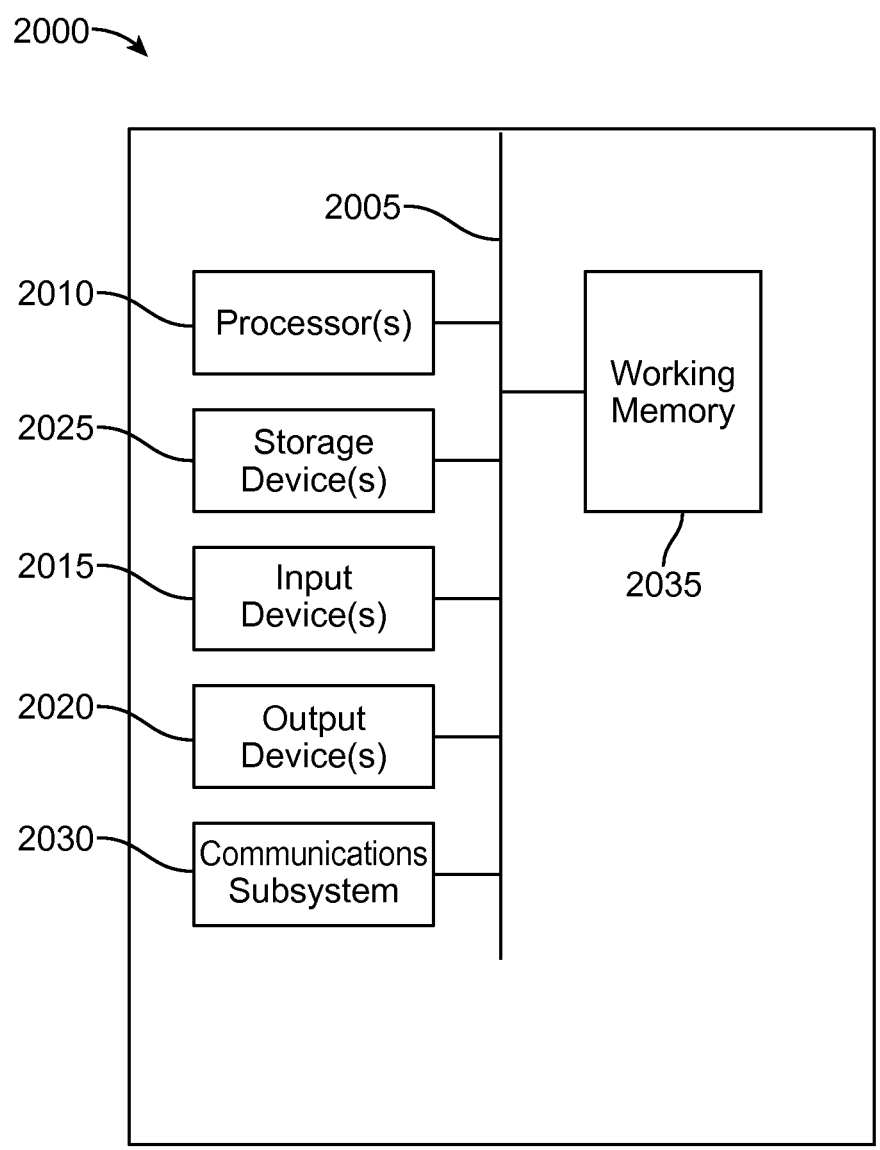
FIG. 20 illustrates one potential embodiment of a computer system or controller that is used in conjunction with a CE-ESI mass spectrometry system in accordance with various embodiments of the innovations presented herein.

In some embodiments, CE controller 110 and MS controller 160 are stand-alone computing devices, or any other acceptable device, as further described by FIG. 20. Controllers in some embodiments function to manage the operation of any component in the system, to receive and analyze data from any part of the system, and to monitor components of the system for errors. In various embodiments, CE controller 110 and/or MS controller 160 are integrated with their respective analysis systems, so that CE controller 110 is integrated with CE Analysis System 130, and/or MS controller 160 is integrated with mass spectrometer 150. Additionally, in certain embodiments, any of the above described components is/are integrated with any other component.

Isolated Power Supply

As described above, FIG. 2A describes a CE-ESI-MS system using a known prior art electrical system configuration where CE power supply 220a is not isolated. FIG. 2B describes a CE-ESI-MS system where the CE power supply is isolated and floating.

FIG. 2B includes CE power supply 220b, inlet vial 232b, conductive fluid vial 234b, electrospray assembly 252b, mass spectrometer 250, and ESI-MS power supply 254. In the system of FIG. 2B, the ESI-MS power supply 254 is grounded, and CE power supply 220b is floating on top of the ES high voltage output 226 of ESI-MS power supply 254. Therefore, if the voltage generated by ESI-MS power supply 254 is 5 kV and the voltage generated by CE power supply 220b is 30 kV, the voltage at CE high voltage output 222b, relative to ground, is 35 kV. This provides a higher CE power supply voltage across sample capillary 242b for the purposes of capillary electrophoresis compared to that which is provided across sample capillary 242a. The term "ground" as used herein is defined as earth ground, chassis ground, or electrical ground. The term "floating ground" as used herein is defined as a circuit ground that is isolated from ground.

Although various embodiments disclosed herein recite specific voltages, the innovations presented herein are not limited to specific voltages or voltage ranges, but apply to any acceptable voltage ranges adequate for function of the described implementation. As a non-limiting example, the voltage rating of an isolated CE power supply is in some embodiments selected from the group consisting of a voltage rating value between 0 kV and 50 kV (inclusive), between 0 kV and 45 kV (inclusive), between 0 kV and 40 kV (inclusive), between 0 kV and 35 kV (inclusive), between 0 kV and 30 kV (inclusive), between 0 kV and 25 kV (inclusive), between 0 kV and 20 kV (inclusive), between 0 kV and −50 kV (inclusive), between 0 kV and −45 kV (inclusive), between 0 kV and −40 kV (inclusive), between 0 kV and −35 kV (inclusive), between 0 kV and −30 kV (inclusive), between 0 kV and −25 kV (inclusive), and between 0 kV and −20 kV (inclusive).

In some embodiments the voltage rating of a non-electrically isolated DC power supply for an ESI-MS power supply is, but is not limited to being, selected from the group consisting of a voltage rating value between 0 kV and 25 kV (inclusive), between 0 kV and 20 kV (inclusive), between 0 kV and 15 kV (inclusive), between 0 kV and 10 kV (inclusive), between 0 kV and 5 kV (inclusive), between 0 kV and 4 kV (inclusive), between 0 kV and 3 kV (inclusive), between 0 kV and 2 kV (inclusive) and between 0 kV and 1 kV (inclusive).

The input to output voltage isolation rating of a DC/DC converter in some embodiments is, but is not limited to being, selected from the group consisting of a voltage isolation rating value between 1 kV and 200 kV (inclusive), between 5 kV and 150 kV (inclusive), between 10 kV and 135 kV (inclusive), between 15 kV and 125 kV (inclusive), between 20 kV and 110 kV (inclusive), between 25 kV and 95 kV (inclusive), between 30 kV and 80 kV (inclusive), between 35 kV and 65 kV (inclusive), between 40 kV and 50 kV (inclusive), between −1 kV and −200 kV (inclusive), between −5 kV and −150 kV (inclusive), between −10 kV and −135 kV (inclusive), between −15 kV and −125 kV (inclusive), between −20 kV and −110 kV (inclusive), between −25 kV and −95 kV (inclusive), between −30 kV and −80 kV (inclusive), between −35 kV and −65 kV (inclusive), and between −40 kV and −50 kV (inclusive).

Figure 2A:
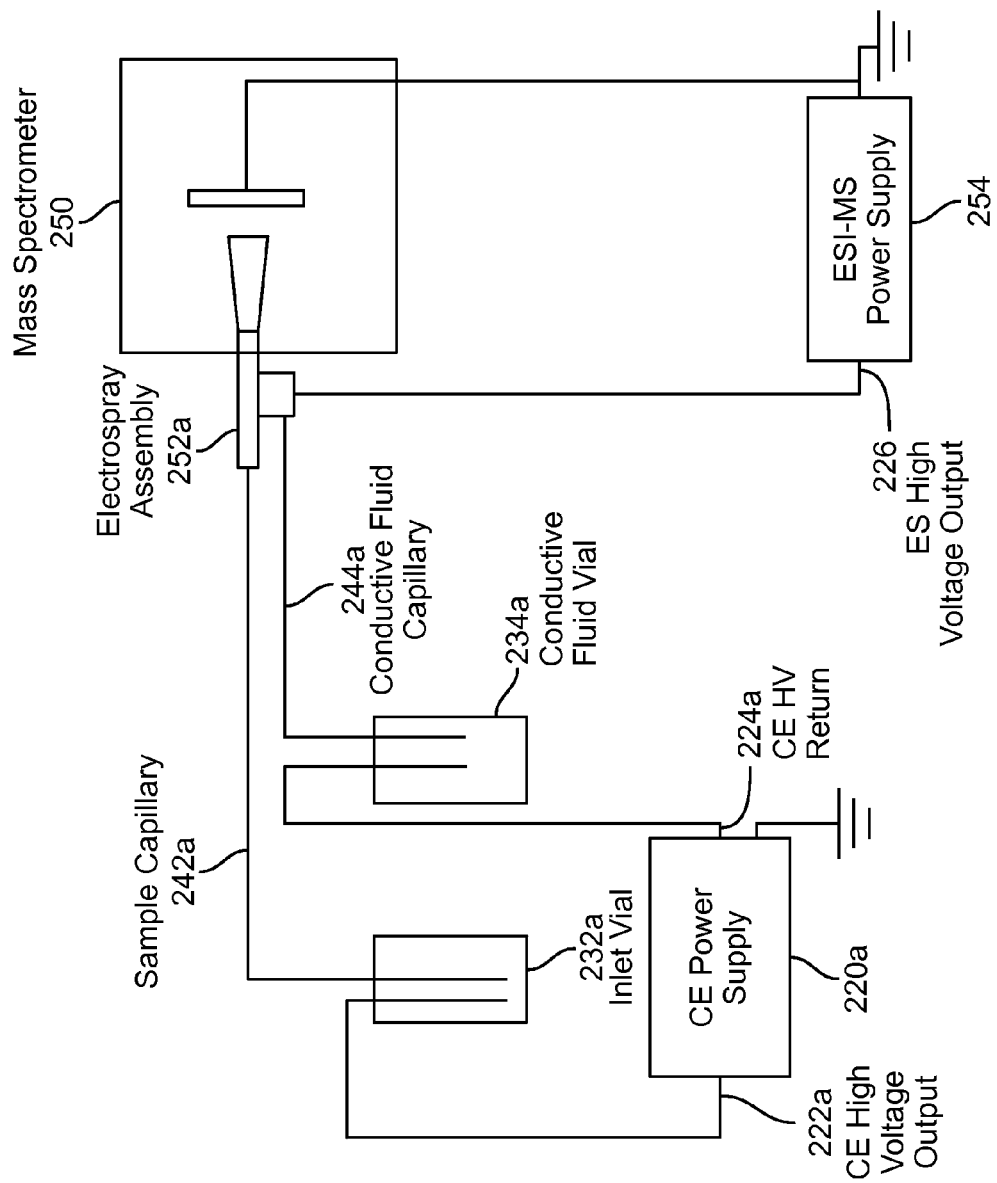
FIG. 2A illustrates a prior art implementation of a CE-ESI mass spectrometry system with a non-isolated power supply.
Figure 2B:
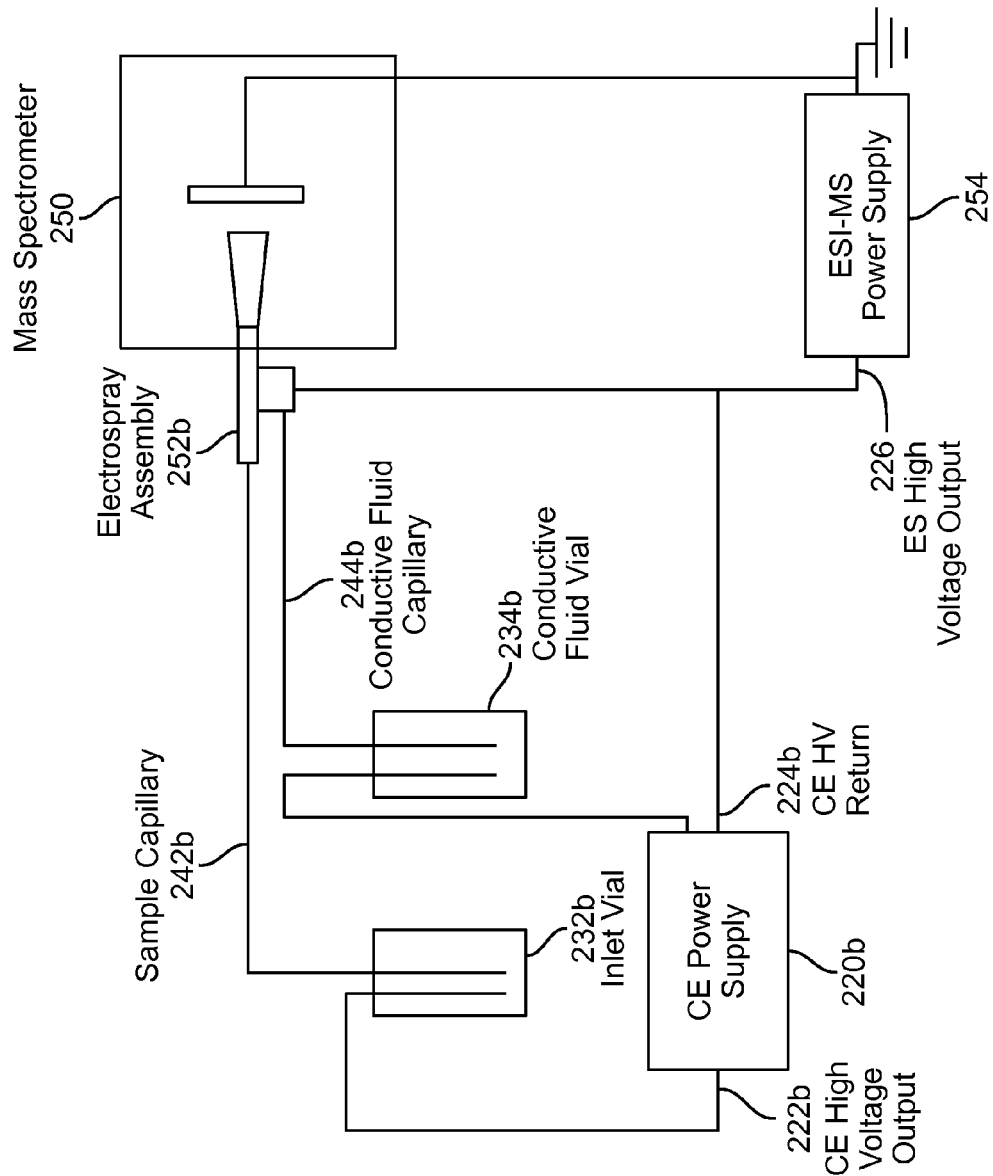
FIG. 2B illustrates a diagram of one potential implementation of a CE-ESI mass spectrometry system with an isolated power supply in accordance with one potential embodiment of the innovations presented herein.

Additionally, in FIG. 2A, the electrospray voltage interacts with the capillary electrophoresis separation voltage because the ESI-MS Power Supply 254 that is used to ionize the separated samples is in the return path of the CE power supply 220a. This creates an additional variable in the capillary electrophoresis component in the system. In the system of FIG. 2B, the electrospray voltage does not interact with the capillary electrophoresis separation voltage. This is a convenience which eliminates a variable of capillary electrophoresis and mass spectrometry data. Use of an isolated power supply thus allows the current returning to the isolated CE power supply to return directly to the CE power supply, bypassing any other components including the ESI-MS power supply. The separation of the CE return current from the MS delivered current enables measurement of the ESI current through a resistor that is only placed in the current path of the MS power supply, and not placed in the return path of the CE power supply.

Figure 3:
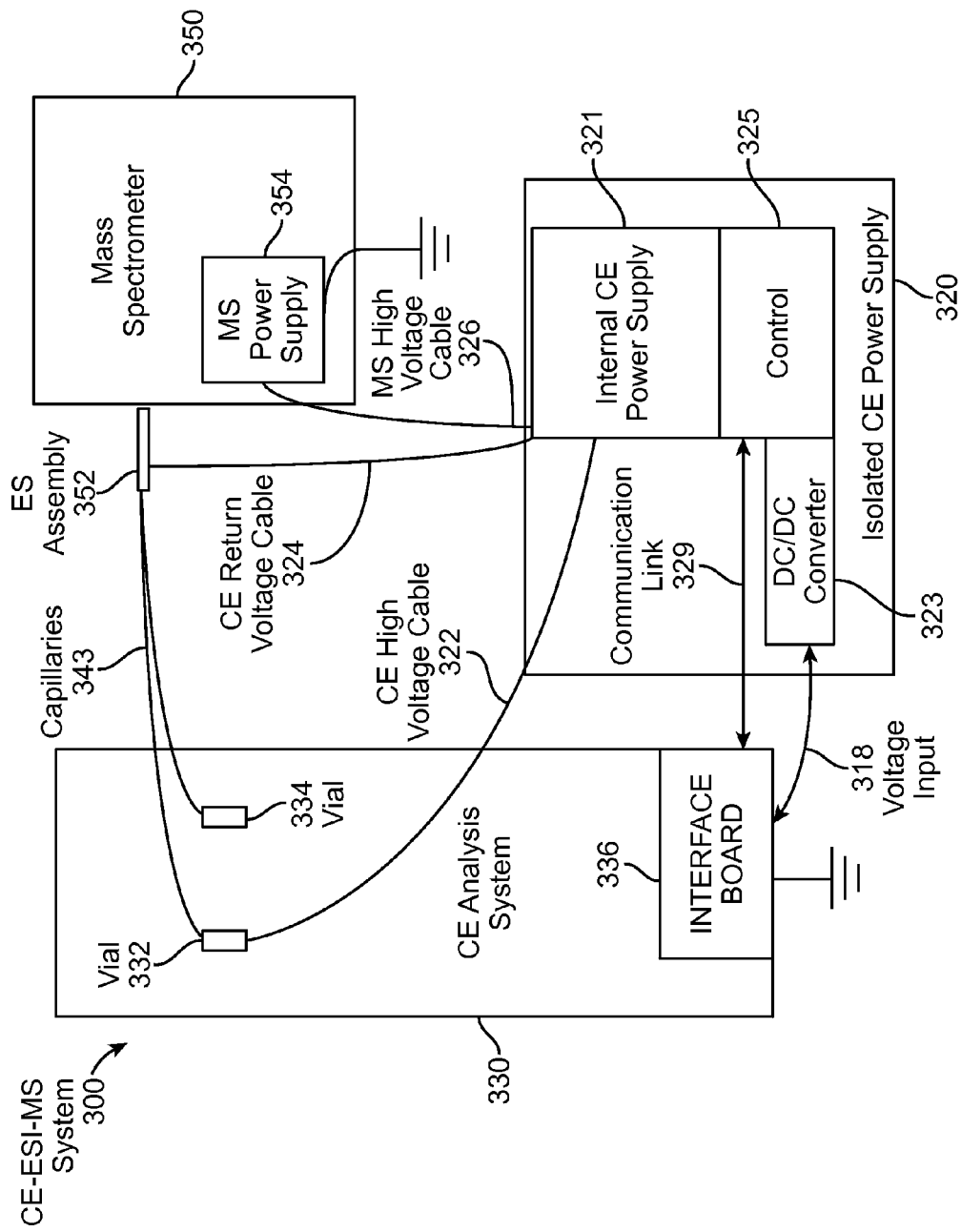
FIG. 3 illustrates a diagram of one potential implementation of a CE-ESI mass spectrometry system with an isolated power supply in accordance with one potential embodiment of the innovations presented herein.

FIG. 3 provides additional details of one potential embodiment of a CE-ESI-MS system 300 that includes an isolated power supply. While CE-ESI-MS system 300 includes a CE analysis system 330, a mass spectrometer 350, and other components similar to the components of FIG. 2A, the system of FIG. 3 describes a system that includes features as part of isolated CE power supply 320 that, in at least one potential embodiment, enable the functionality of a CE-ESI-MS system with a floating power supply that is not possible in the system of FIG. 2A.

Isolated CE power supply 320 includes a floating control 325 and a DC/DC converter 323, and a CE power supply 321. CE power supply 321 is in some embodiments comparable to CE power supply 220a of FIG. 2A. CE power supply 321 provides CE separation voltage, but has no integrated special function for dealing with the necessities of isolation. Floating control 325 and DC/DC converter 323 are in some embodiments integrated with CE power supply 321 to enable operation as isolated CE power supply 320.

Floating control 325 is isolated from chassis ground but maintains a link to CE analysis system 330 across communication link 329. In some embodiments, communication link 329 comprises a wireless communication link. Alternatively, communication link 329 comprises an optical communication link such as a link via an optical fiber. An optical fiber communication link provides the benefit of being highly resistive, and therefore able to function across the isolation when the isolated CE power supply 320 is floating on a large voltage. In some embodiments, optical coupler devices with a sufficient isolation rating are used directly to pass digital inputs and outputs. Because power supply units such as CE power supply 321 frequently require analog input controls, but optical couples are not directly functional for most such controls, analog signals in some embodiments are first converted to a logic pulse stream, routed through the same optical coupler devices used for any digital signals, and then reconstructed back into analog signals. In some embodiments, such translation is performed using interface board 336 and control circuitry 325.

Voltage for the analog circuitry on the remote end is provided by the host instrument DC supply and on the isolated end by the DC/DC converter 323 which, in some embodiments, comprises a DC switcher. Interface board 336 that is on the other side of the communication from the floating control 325 is therefore able to operate at the chassis ground with no risk of an electrical short across communication link 329.

A DC/DC converter 323 similarly functions for providing voltage outputs for control circuit 325 and CE power supply 321 while isolating these components of the isolated CE power supply 320. Converter 323 is therefore a high isolation voltage (40 kV, as a non-limiting example) DC/DC power converter or DC switcher power supply or power isolator (DC/DC converter) that is used to isolate input power to the other components of the Isolated CE Power Supply 320. For example, in some embodiments DC/DC converter 323 accepts a 24V voltage input from the interface board 336, and using that input voltage, provides an isolated output for use by the rest of the components of isolated CE power supply 320 that are floating on the voltage output of MS power supply 354. In such embodiments, DC/DC converter provides reference and operation voltages across large isolation voltages that in some embodiments are in the order of 15kV or more.

Isolated CE power supply 320 therefore functions using an isolated communication channel in the form of communication link 329 and using an isolated voltage input from DC/DC converter 323.

Figure 4:
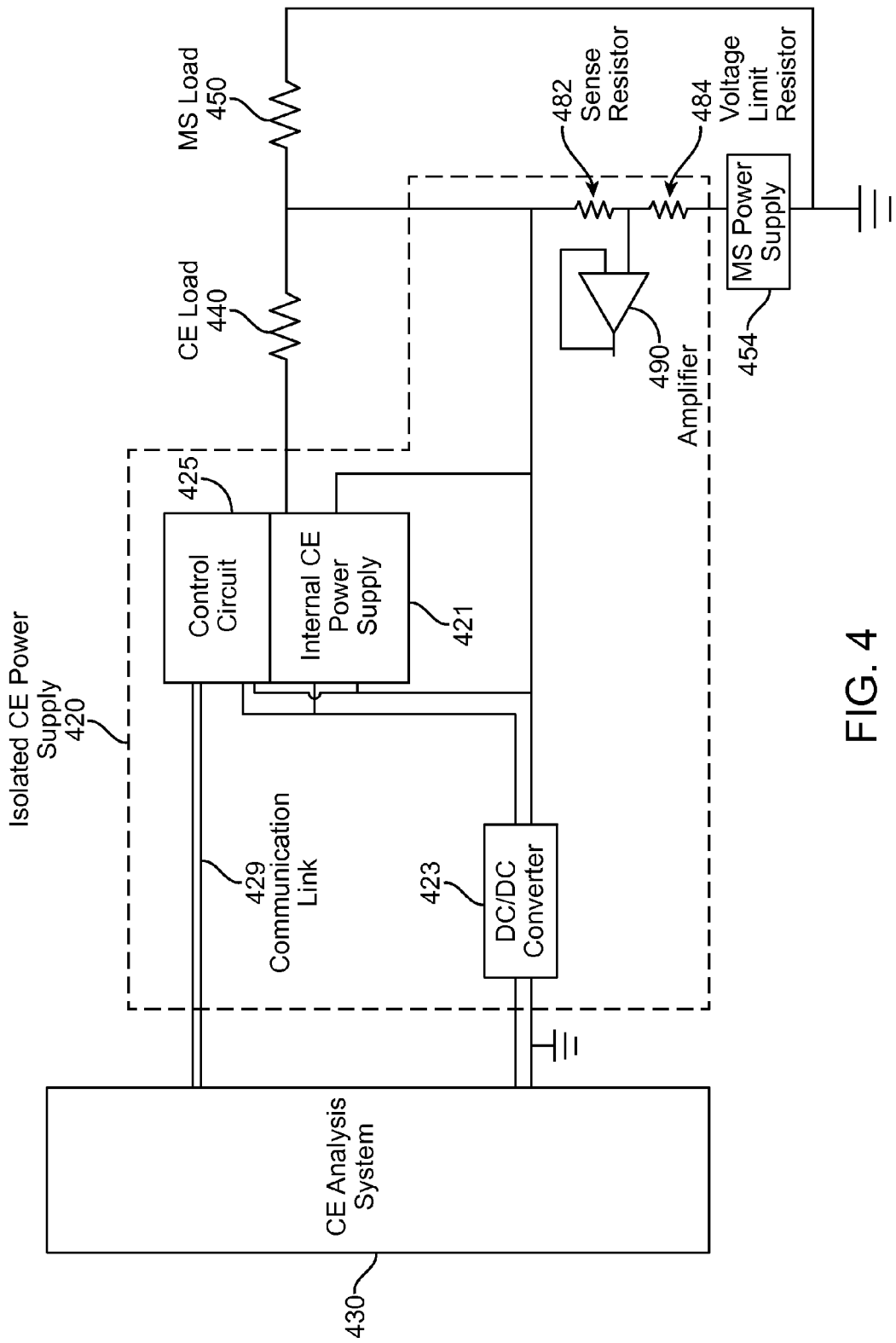
FIG. 4 illustrates a diagram of one potential implementation of a CE-ESI mass spectrometry system with an isolated power supply in accordance with one potential embodiment of the innovations presented herein.
Figure 5:
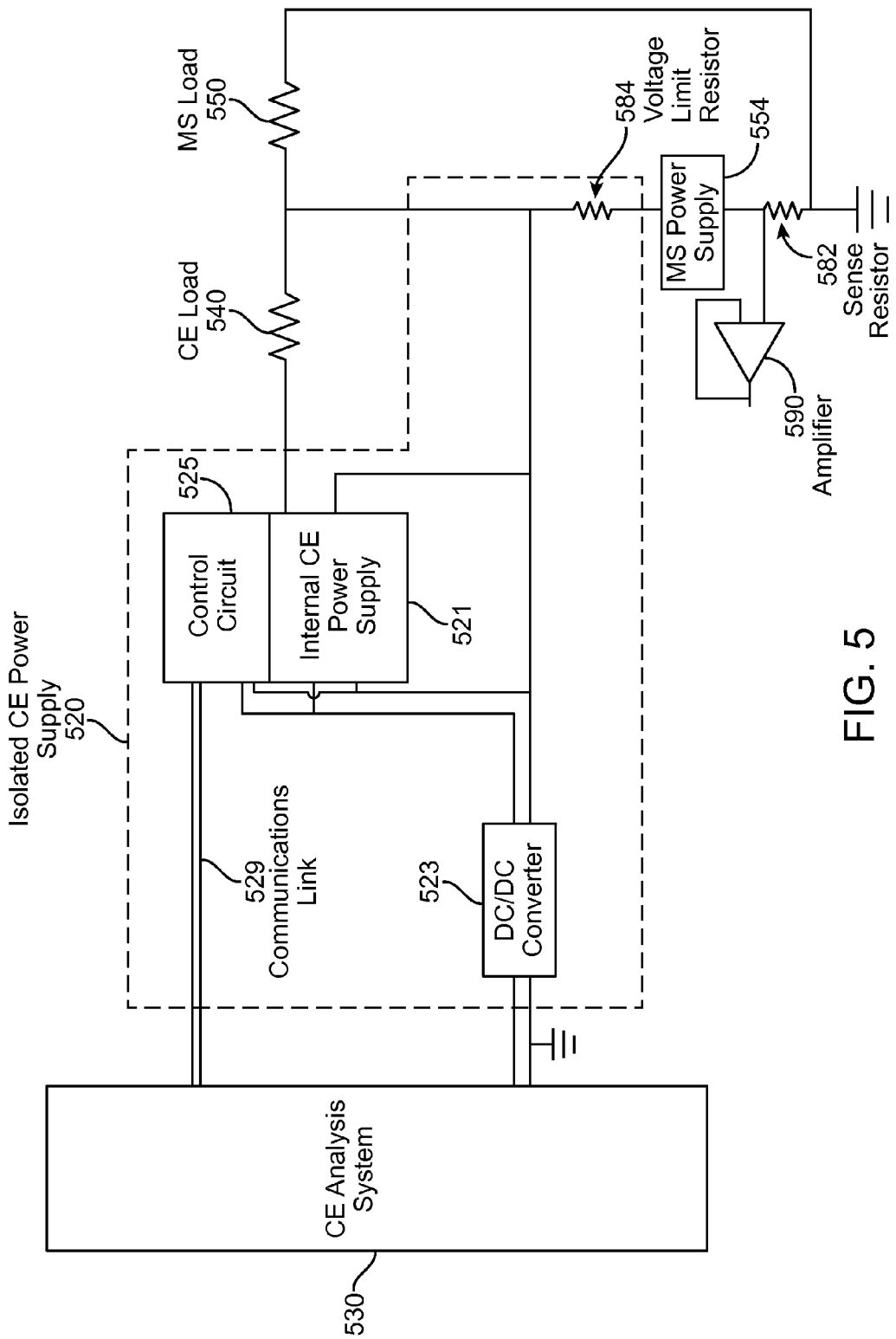
FIG. 5 illustrates a diagram of one potential implementation of a CE-ESI mass spectrometry system with an isolated power supply in accordance with one potential embodiment of the innovations presented herein.
Figure 6:
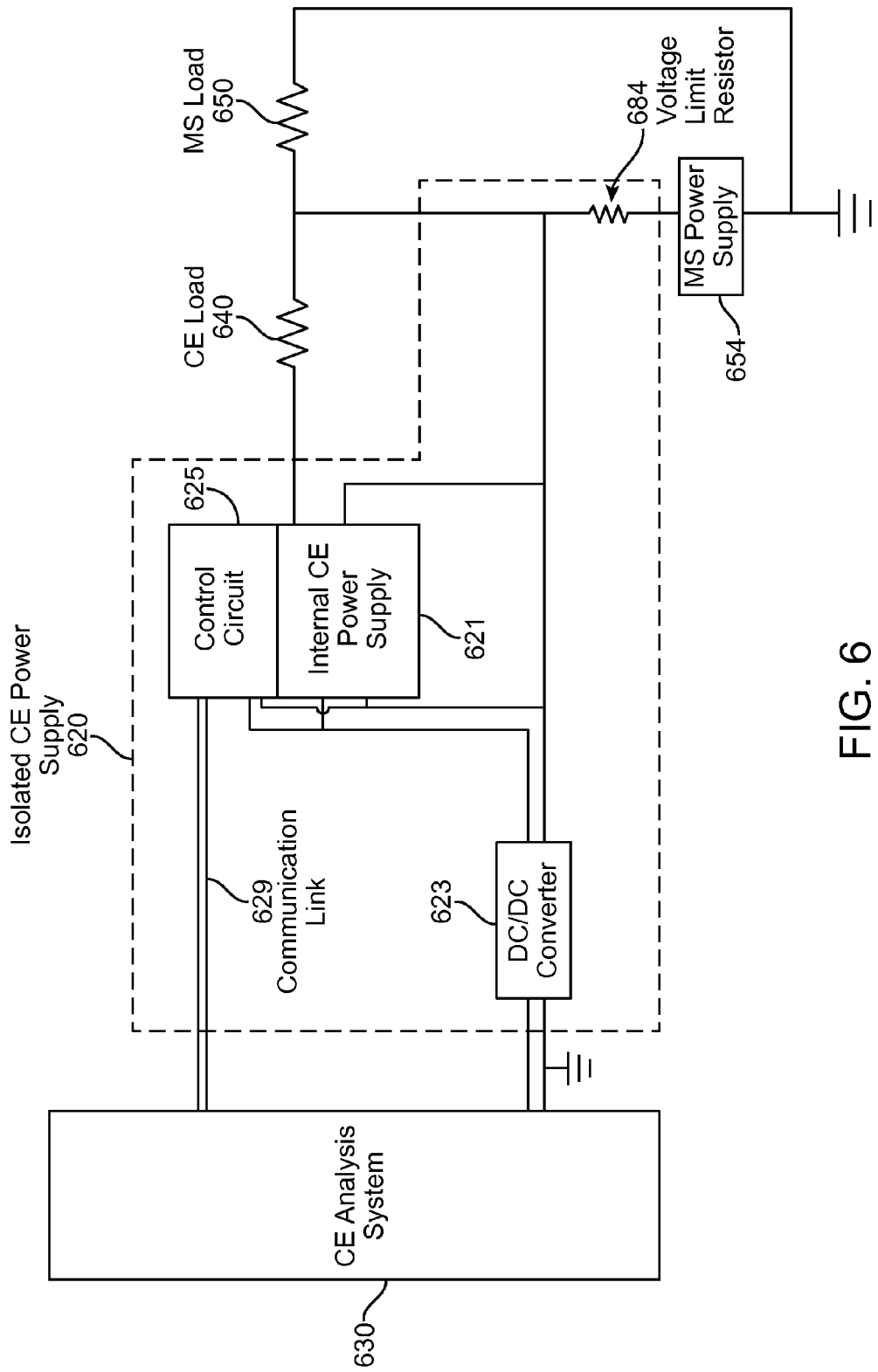
FIG. 6 illustrates a diagram of one potential implementation of a CE-ESI mass spectrometry system with an isolated power supply in accordance with one potential embodiment of the innovations presented herein.

In addition to the above described benefits of an isolated power supply in a CE-ESI-MS system, certain embodiments include improvements related to leakage current. FIGS. 4, 5, and 6 describe different embodiments that include such improvements.

FIGS. 4, 5, and 6 illustrate CE-ESI-MS systems having an isolated CE power supply 420, 520, and 620, respectively. Each isolated CE power supply includes a DC/DC converter (423, 523, and 623, respectively) an isolated control circuit (425, 525, and 625, respectively) and an internal CE power supply (421, 521, and 621, respectively). In FIGS. 4, 5, and 6, the electrical path along separation capillary is shown as CE load 440, 540, and 640, respectively, and the ESI-MS electrical return path for MS power supply 454, 554, and 654 is shown as MS load 450, 550, and 650, respectively. FIGS. 4, 5, and 6 include a voltage limit resistor 484, 584, and 684, respectively. FIGS. 4 and 5 also include a sense resistor 482 and 582, respectively. FIGS. 4 and 5 additionally include an amplifier 490 and 590, respectively.

Voltage limit resistor 484 acts as a current limit resistor, which protects both the current sense circuit that includes amplifier 490 and also protects the non-floating electrospray ionization-mass spectrometer power supply in the event of a failure. One non-limiting example of such a failure that is detected in some embodiments by sense resistor 482 and amplifier 490 is the formation of a salt bridge during capillary electrophoresis operation.

Along with voltage limit resistor 484, sense resistor 482 and amplifier 490 are in some embodiments part of a current sense circuit that detects leakage current. Whereas in standard CE-ESI-MS systems a visual or data based failure of sample separation or some other obvious system failure in the data is generally the first sign of system failure, the use of a current sense circuit in some embodiments provides feedback to automatically shut down operation if a fault mode is detected. The salt bridge failure mentioned above is a non-limiting example of a failure which is detected using some embodiments of the current sense circuit.

If leakage occurs, voltage limit resistor 484, which has a high value, prevents damage both to the current sense circuit comprising amplifier 490 and to the (non-isolated, non-floating) mass spectrometer power supply 454 because most of the voltage will appear across this voltage limit resistor 484. One non-limiting example of a high value voltage limit resistor 484 is a resistor having a value of 200 megaOhms. The DC/DC converter 423 is functionally in parallel with the current sense resistor 482, the voltage limit resistor 484, and the (non-isolated, non-floating) ESI-MS power supply 454. In case of leakage, the DC/DC power converter 423 in some embodiments is designed to withstand the sum of the CE 'separation capillary' and electrospray voltages in order to avoid damage to the system.

As described above for power supply ratings, the resistor values of voltage limit resistor 484 and sense resistor 482 are not limited to the specific values used for example purposes. For example, a current sense resistor according to the present innovations includes any value that enables the current sensing function and allows the described system to function. A current sense resistor, in one embodiment, comprises a resistor having a rating value between 1 kOhm and 503 kOhms, inclusive.

In one embodiment, voltage limit resistor 484 comprises a resistor having a value that is selected from the group consisting of between 10 megaOhms and 500 megaOhms (inclusive), between 50 megaOhms and 400 megaOhms (inclusive), between 100 megaOhms and 300 megaOhms (inclusive), between 150 megaOhms and 250 megaOhms (inclusive), between 175 megaOhms and 225 megaOhms (inclusive), between 185 megaOhms and 215 megaOhms (inclusive), between 190 megaOhms and 210 megaOhms (inclusive), and between 195 megaOhms and 205 megaOhms (inclusive).

In a conventional (grounded) CE-ESI-MS system such as the one shown in FIG. 2A, as well as in embodiments without a current detecting circuit, the leakage current generally is extremely difficult to detect, or only detectible with high margins of error, because the leakage current returns to the CE high voltage power supply along with the current delivered to the CE 'separation capillary' by bypassing the return current terminal in the CE high voltage supply. The current delivered to the CE 'separation capillary' will not return to the CE high voltage power supply through its return terminal (shown as CE HV return); instead it returns through the ground connection of the ESI-MS Power Supply. The leakage current will bypass all of the other circuitry, capillaries, and power supplies and return to the CE high voltage power supply through the connection to ground. To sense the current flowing through the ESI-MS power supply, the current sense resistor 482, which in some embodiments has a value in the order of 500 kOhms, is inserted between the high voltage output of the (non-isolated, non-floating) ESI-MS power supply 454 and the floating ground of the CE power supply 421. This is done out of the path of any current returning to CE power supply 421.

The voltage across the current sense resistor 482 then represents the sum of the electrospray ionization current delivered by the (non-isolated, non-floating) ESI-MS power supply 454 and any leakage current due to a fault condition caused by, as a non-limiting example, a salt bridge. An amplifier measures this voltage, and an absolute value amplifier ensures the signal can be read if the power supply polarity is reversed.

FIG. 5 shows an alternative embodiment of CE-ESI-MS system including a current sense circuit. In the embodiment shown in FIG. 5, the sense resistor 582 is grounded and placed outside the isolated CE power supply 520. The voltage limit resistor 584 remains on the high power side of the MS power supply 554 in order to serve in the protective function described above. Sense resistor 582 and amplifier 590 provide the sensing function in this alternative embodiment, and enable a controller or fault detection system to identify excess current and shut the system down, since sense resistor remains out of the return path of CE power supply 521 but in the path of any leakage current before it returns to the isolated CE supply 521. By operating outside of the isolated CE power supply, the current sense circuitry including amplifier 590 and sense resistor 582 in some embodiments lowers the usage and reliance on communication link 529, and in some embodiments reduces design complexity by reducing the number of components and complexity of components operating at the high floating voltage.

Finally, FIG. 6 shows an additional alternative embodiment without the leakage current sensing function shown in FIGS. 4 and 5. FIG. 6 includes voltage limit resistor 684 and does not have any equivalent to sense resistor 582 or amplifier 590. A high rated voltage limit resistor 684 in such embodiments continues to perform the protective function without the additional circuitry and fault detection controls necessary for the current sensing circuitry to function. Instead, at least some embodiments of FIG. 6 provide a lower cost and/or easier to implement solution, while protecting the system components from damage. As described above, a fault condition associated with a salt bridge, as a non-limiting example, in some embodiments is detected from identifiable performance degradation in sample separation, or identifiable characteristics of output data that do not conform with expected or acceptable data characteristics. Voltage limit resistor 684 in some embodiments protects MS power supply 654 from damage until such characteristics are identified and the system halted for repair.

CE Consumable Cartridge

Figure 7:
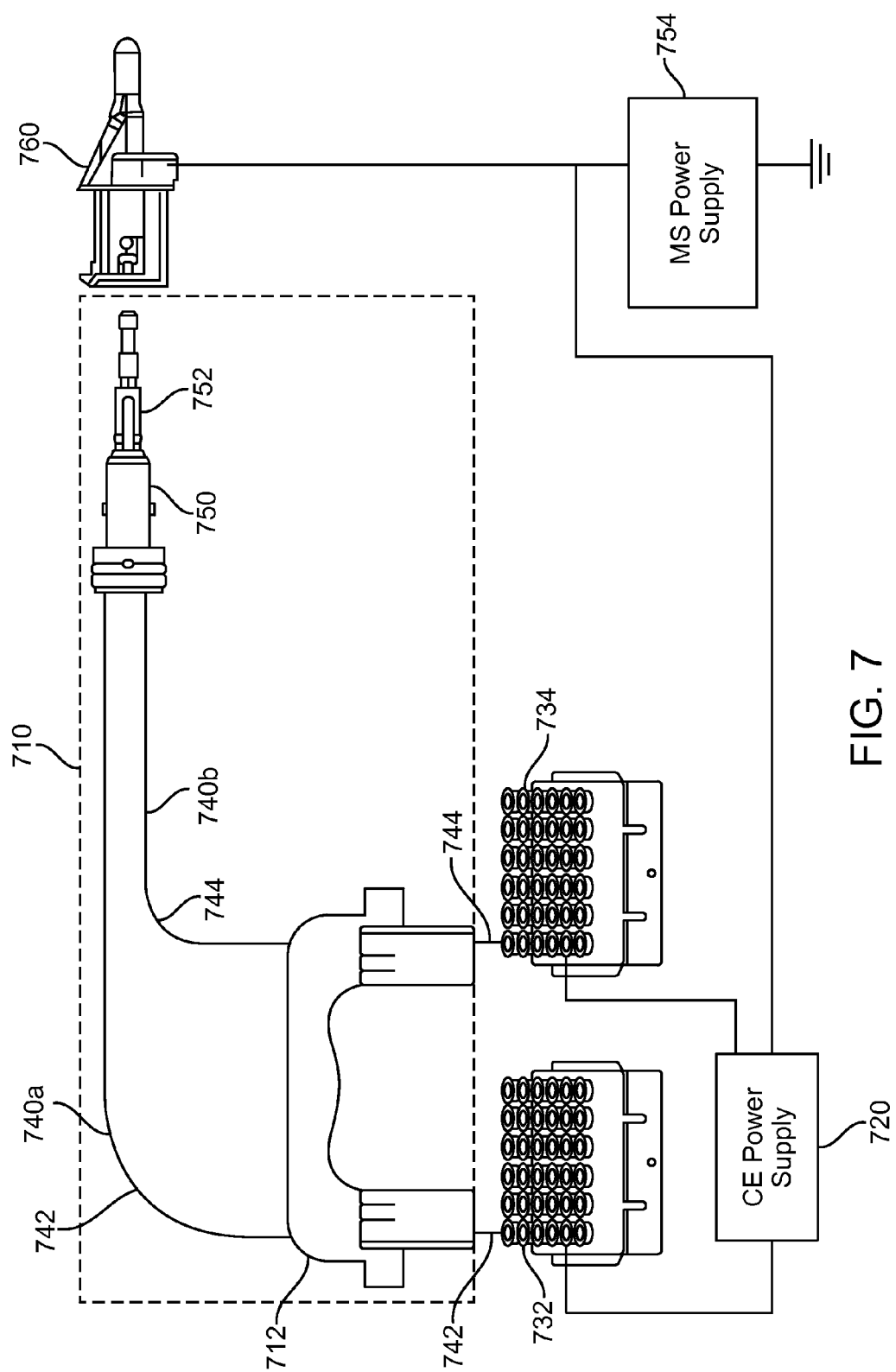
FIG. 7 illustrates a cartridge assembly and an adapter as part of a CE-ESI mass spectrometry system in accordance with one potential embodiment of the innovations presented herein.

FIG. 7 shows an aspect of a CE-ESI-MS system such as CE-ESI-MS system 100 of FIG. 1. FIG. 7 includes sample vials 732, conductive fluid vials 734, adapter 760, MS power supply 754, CE Power supply 720, and cartridge assembly 710. Cartridge assembly 710 includes separation capillary 742, conductive fluid capillary 744, cartridge 712, coolant tubes 740a and 740b, and sprayer housing 750. Sprayer housing 750 includes electrical contact 752, as well as other significant elements described in more detail below, especially in regard to FIGS. 15-17.

In some embodiments cartridge assembly 710 functions as a consumable assembly that enables capillaries to be inserted and removed much more easily than in traditional CE-ESI-MS systems. Interfacing a CE system with a mass spectrometer is a delicate and time consuming process. Traditional CE-ESI-MS alignment requires interfacing the inlet of an ESI sprayer tipped separation capillary to the CE system, and positioning the ESI sprayer tip accurately at the inlet of a MS for a proper ion spray. A prebuilt CE capillary holder cartridge assembly with at least one portion of the ESI sprayer tipped separation capillary enclosed in at least one protective holder simplifies the CE-MS interface. Some embodiments of such a cartridge assembly comprise an ESI sprayer tip enclosed in a protective sprayer housing that mounts readily on a mechanical stage at the inlet of the MS. More particularly, some embodiments of such a cartridge assembly comprise a sheathless ESI sprayer tip enclosed in a protective sprayer housing that mounts readily on a mechanical stage at the inlet of the MS. Some embodiments of such a cartridge assembly comprise a portion of a separation capillary enclosed in a CE cartridge that mounts readily on the CE system without requiring delicate operation. For a sheathless ESI sprayer tipped separation capillary, the conductive fluid necessary to make electrical contact with the inner bore of the capillary is in some embodiments supplied by the CE system through a conductive fluid capillary, wherein a portion of the conductive fluid capillary is enclosed in the CE cartridge that mounts readily on the CE system. Thus, in some embodiments, a cartridge assembly of the innovations presented herein is selected from the group consisting of a cartridge assembly comprising an ESI sprayer tip enclosed in a protective sprayer housing, a cartridge assembly comprising a portion of a separation capillary enclosed in a CE cartridge, a cartridge assembly comprising a portion of a conductive fluid capillary enclosed in a CE cartridge, or a combination thereof. Moreover, in some embodiments, a cartridge assembly of the innovations presented herein is selected from the group consisting of a cartridge assembly comprising a sheathless ESI sprayer tip enclosed in a protective sprayer housing, a cartridge assembly comprising a portion of a separation capillary enclosed in a CE cartridge, a cartridge assembly comprising a portion of a conductive fluid capillary enclosed in a CE cartridge, or a combination thereof The benefit of a cartridge assembly 710 is therefore both in the connection to a CE analysis system such as CE analysis system 130 of FIG. 1 and in the connection to a mass spectrometer such as mass spectrometer 150 of FIG. 1. On the CE analysis side of cartridge assembly 710, improved functionality is in some embodiments provided by disposing capillaries within a protective cartridge that in some embodiments interfaces with a CE analysis system as a cartridge, and not as individual capillaries. The fixed position and protective cartridge housing capillaries 744 and 742 in some embodiments additionally prevents damage to the fragile capillaries.

The same advantageous, prebuilt cartridge assembly 710 also provides a benefit with respect to cooling, where inflow and outflow of cooling fluid in some embodiments occur via a cartridge 712 interfacing with a CE analysis system. In one potential embodiment, cooling fluid enters cartridge 712 on the side of separation capillary 742, and enters cooling tube 740a at an interface within cartridge 712 that is sealed. Cooling fluid flows toward sprayer housing 750, and enters a fluid return block, where the separation capillary 742 that is threaded inside cooling tube 740a separates from cooling tube 740a. Cooling fluid is blocked by a seal from flowing toward the MS inlet where separation capillary 742 provides separated sample material to the ESI-MS input. The cooling fluid instead returns to cartridge 712 via cooling tube 740b that contains conductive fluid capillary 744 threaded within cooling tube 740b. The cooling fluid then exits cooling tube 740b and cartridge 712 to return to CE analysis system to be re-circulated through the cooling system. The cooling fluid thus travels a cooling fluid circuit through a cooling system.

On the MS side of the connection with the cartridge assembly 710, improved functionality is in some embodiments provided by an integrated ESI sprayer tip as part of sprayer housing 750. Sprayer housing 750 in some embodiments provides increased electrical safety by placing the electrical path to MS power supply 754 and CE power supply 720 on an adapter 760 which is attached to the mass spectrometer and rarely moved. In some embodiments electrical contact is made as the sprayer housing 750 is inserted into the adapter 760 and electrical contact 752 on the exterior of sprayer housing 750 makes connection with an electrical contact on the inside of adapter 760. Making this electrical connection without the need for the electrical connection to move with the sprayer housing 750 provides a benefit of reduced risk of damage to the electrical connection and reduced risk to an installer.

Further, mechanical damage is in some embodiments prevented through the use of a sprayer housing 750. A High Sensitivity Porous Sprayer (HSPS) capillary tip is very fragile and requires protection when it is not installed. In some embodiments this device has an automatically retracting and extending cover that protects the sprayer tip when it is not installed. Additionally, the fragile capillary sprayer tip within sprayer housing 750 does not need to be attached and adjusted directly. Instead, in some embodiments x, y, z position adjustments are made to the sprayer housing 750 and/or to the adapter 760 with the sprayer housing 750 inserted and attached.

The improvements described above of additional protection for the capillary tip, integrated liquid cooling, and fixed protective connection points for the capillary at both the CE and MS interfaces are benefits and improvements not previously known.

FIG. 8 shows an alternative embodiment of portions of a cartridge assembly. FIG. 8 shows ESI sprayer tip 858 of separation capillary 842 disposed inside retracting protective housing 854, protective sheaths 845a and 845b, capillary cassette 846, conductive fluid capillary 844 shown both exposed for interface with a vial and disposed inside coolant tubing, cartridge 812, coolant manifold 848, and electrical contact 852.

In certain embodiments, conductive fluid capillary 844 is assembled into a capillary cassette that plugs into a CE analysis instrument directly. In some embodiments, separation capillary 842 is assembled into a capillary cassette that plugs into a CE analysis instrument directly. In some embodiments, separation capillary 842 and conductive fluid capillary 844 are each assembled into discrete capillary cassettes that each plug into a CE analysis instrument directly. In alternate embodiments, such as the embodiment shown in FIG. 8, the conductive fluid capillary 844 is first assembled into the capillary cassette 846 and then attaches to the CE analysis instrument through an interface cartridge 812 to form a coolant interface. A protective sheath 845b houses the capillary and prevents breakage when the capillary is not installed. When the capillary is installed, the protective sheath retracts to expose the capillary as shown in FIG. 8 with sheath 845b. A similar mechanism exists for the separation capillary 842 which is shown within protective sheath 845a in a protective (not retracted) position.

In some embodiments, prior to assembly of a cartridge assembly with capillaries, each capillary is first integrated with a discrete capillary cassette and housed within a discrete protective sheath. In some embodiments each such protective sheath is inserted into an open slot within cartridge 812 as part of the creation of a cartridge assembly. In some embodiments protective sheaths 845a and 845b continue to protect the associated capillaries after completion of a cartridge assembly. In alternative embodiments, discrete protective sheaths 845a and 845b are integrated with cartridge 812 prior to insertion of each capillary cassette 846. Additional details related to capillary cassettes will be discussed below.

Each capillary is threaded through a discrete tubing which encases the coolant flow and which leads up to a coolant manifold 848. The conductive fluid capillary 844 delivers electrolyte to a conductive (e.g., steel, as a non-limiting example) tube that surrounds the separation capillary in the sprayer housing. At this point the conductive fluid capillary truncates. The separation capillary 842 is surrounded by the conductive electrolyte fluid as it passes through the conductive (e.g., steel, as a non-limiting example) tube; then the ESI sprayer tip 858 of separation capillary 842 extends beyond the conductive tube. As the ESI sprayer tip 858 is very fragile, it is covered by a protective housing 854 that in some embodiments retracts when the assembly is installed into the MS. A feature is built into the cartridge assembly that will allow electrical contact at 852 to be established when installed as described above with respect to electrical contact 752 in FIG. 7. The coolant manifold 848, the electrical contact 852 and the protective housing 854 for the ESI sprayer tip 858 form a consolidated end of the cartridge assembly at the MS end of one potential embodiment of a CE-ESI cartridge assembly.

Figure 9A:
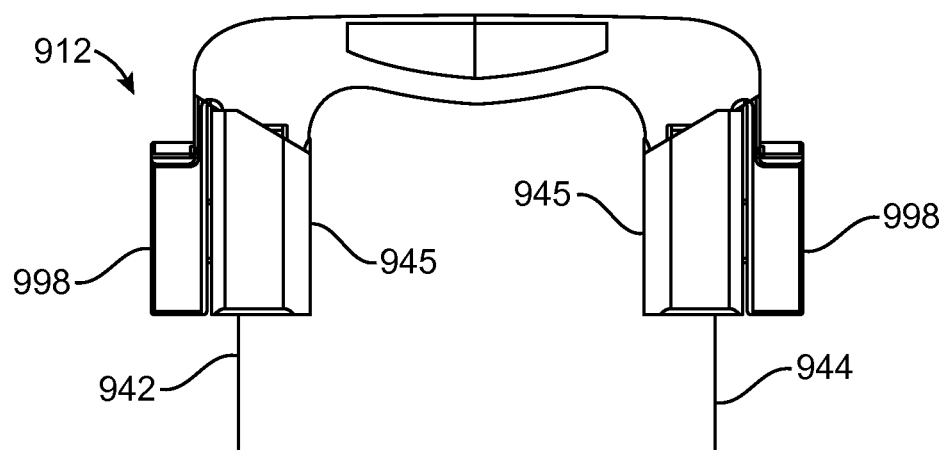
FIG. 9A illustrates a cartridge assembly that is used as part of a CE-ESI mass spectrometry system in accordance with one potential embodiment of the innovations presented herein.
Figure 9B:
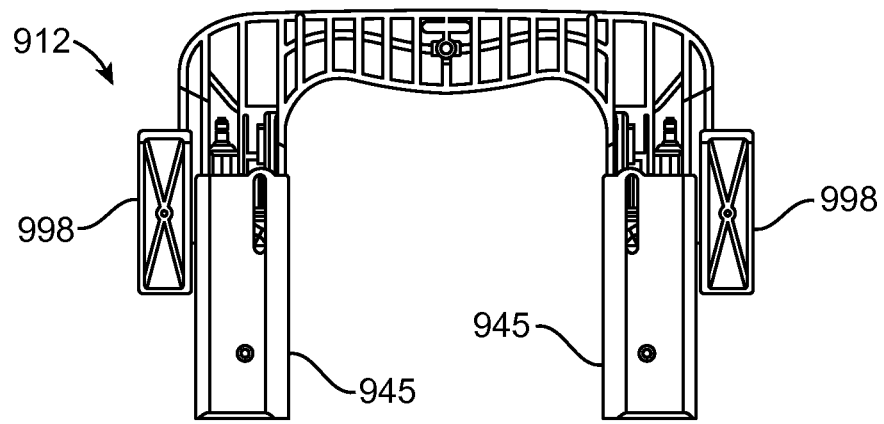
FIG. 9B illustrates a cartridge assembly that is used as part of a CE-ESI mass spectrometry system in accordance with one potential embodiment of the innovations presented herein.

FIGS. 9A and 9B show an additional view of one potential embodiment of a cartridge 912 that in some embodiments is part of a cartridge assembly. Cartridge 912 includes installed capillary cassettes that are protected by the shown protective sheaths 945. In FIG. 9A, protective sheaths 945 are shown in a retracted position to allow separation capillary 942 and conductive fluid capillary 944 to interface with their respective vials as part of a CE analysis system. In FIG. 9B, protective sheaths 945 are shown in a protective non-retracted (extended) position such that the capillaries 942 and 944 are protected but also not able to operate or interface with the appropriate vials. Additionally, in the embodiment shown in FIGS. 9A and 9B, cartridge 912 includes insertion guides 998 that in some embodiments assist in the ease of connecting (or disconnecting) cartridge 912 with a CE analysis system. In some embodiments, such a CE analysis system has receiving slots that match insertion guides 998 to provide a secure position and placement of the cartridge 912 within the CE system, and to appropriately position the capillaries 942 and 944 and protective sheaths 945 so that the capillaries will be readily able to interface with the appropriate vial when a CE analysis system is operating.

Further still, in some embodiments insertion guides 998 assist in moving cartridge 912 within a CE analysis system. In certain embodiments, such as the embodiment shown in FIG. 7, a CE analysis system has a set of vials, and includes automation for moving a capillary to the appropriate vial or for moving an appropriate vial to a capillary. In certain embodiments, a cartridge such as cartridge 912 is moved by and within a CE analysis system to multiple vials with protective sheath 945 protecting the capillaries during movement. In certain embodiments, multiple vials are moved by and within a CE analysis system to an at least one capillary housed in a cartridge such as cartridge 912 with protective sheath 945 in some embodiments protecting the capillaries during vial movement.

Figure 10C:
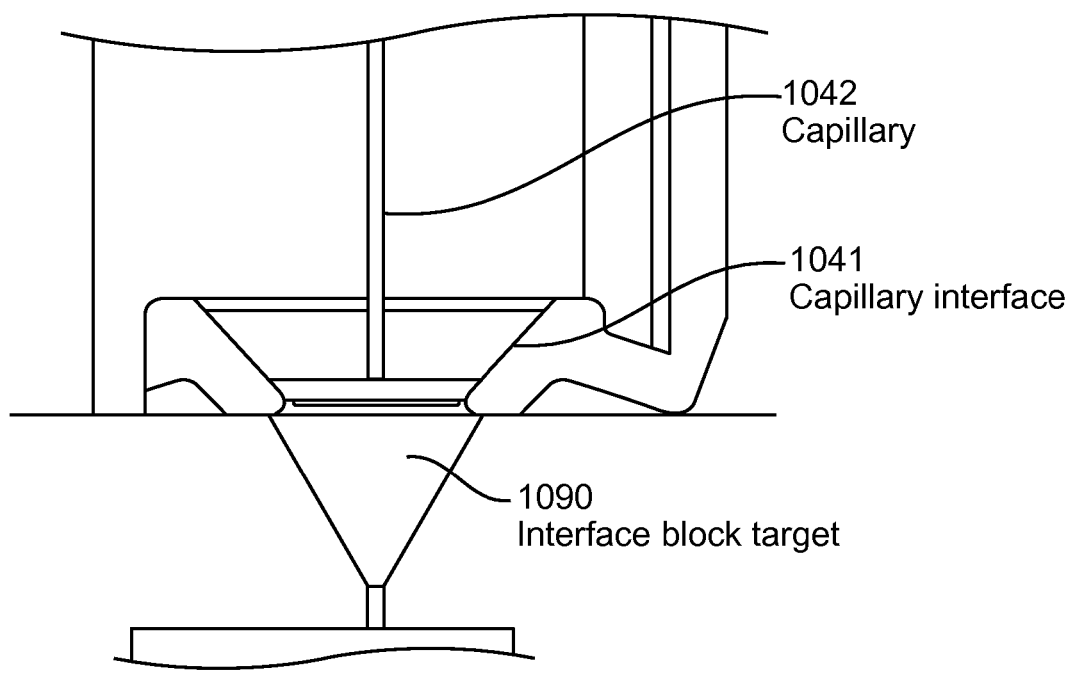
FIG. 10C illustrates a portion of a cartridge assembly including a capillary protection cover (sheath in extended position and including a guide pass through) that is used as part of a CE-ESI mass spectrometry system in accordance with one potential embodiment of the innovations presented herein.

FIGS. 10A, 10B, 10C, and 10D show further additional detail of some alternative embodiments of capillary cassettes and of protective sheaths. FIG. 10A shows protective sheath 1045 in a protective extended position. FIG. 10B shows protective sheath 1045 in a retracted position. FIGS. 10A and 10B additionally show seal 1043, capillary interface 1041, and separation capillary 1042. Capillary interface 1041 provides a path for the separation capillary 1042 to extend from the protective sheath 1045 when the sheath 1045 is in the refracted position as in FIG. 10B. Seal 1043 surrounds the separation capillary 1042 at a point that provides a stop for coolant fluid that surrounds separation capillary 1042 and cools it, such that the conductive fluid is contained by a cooling tube and various seals including seal 1043 that allows separation capillary 1042 access to a sample vial while the conductive fluid that cools the separation capillary 1042 is contained and prevented from leaking As shown in FIG. 10A, in some embodiments capillary interface 1041 is structured to fit with a portion of seal 1043 that surrounds a portion of separation capillary 1042 when the protective sheath 1045 is retracted as in FIG. 10B. In certain embodiments, similar structures exist for an associated conductive fluid capillary.

FIG. 10C shows one potential alternative embodiment including a capillary cassette and protective sheath as described above. In certain embodiments, the capillary interface 1041 functions as a guide to direct the capillary out of a protective sheath without damaging the capillary. In some embodiments, this further functions with an interface block target 1090 which accepts capillary 1042 as it is guided out of capillary interface 1041 into an interface block having interface block target 1090, such that the capillary is guided while in use to limit damage to capillary 1042 and to guide the capillary. Thus, in some embodiments, in order to ensure the end of capillary 1042 is aligned correctly with an interface block, a capillary interface 1041 is integrated into the bottom of the sheath with a tapered guiding feature. In some embodiments, the guide feature has a narrow pass through that is designed to always fall within the interface block target 1090. The top of the capillary interface 1041 guide feature is wider to allow for a higher degree of initial misalignment of the capillary. In some embodiments, this allows the capillary to physically rest on the wall of the guide feature in order to correct any lateral offset created by a poor exit angle of the capillary from the cartridge.

Figure 10D:
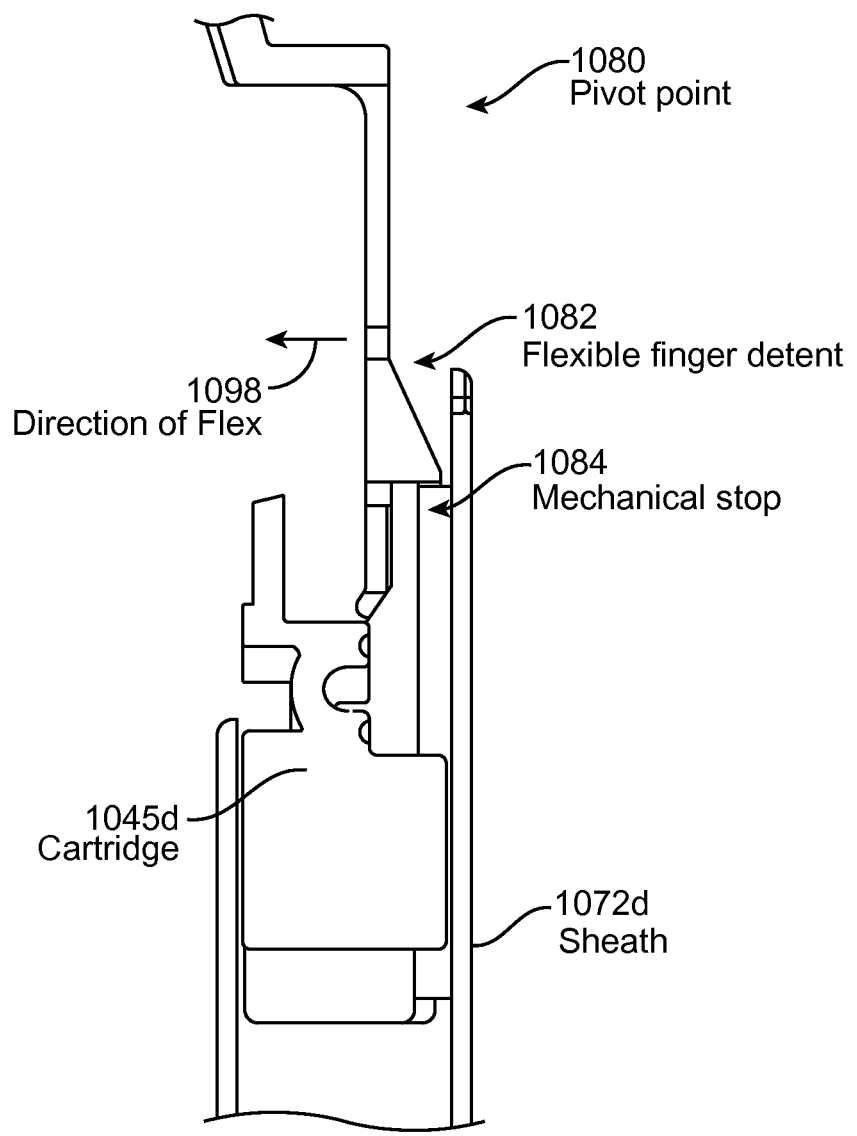
FIG. 10D illustrates a portion of a cartridge assembly including a capillary protection cover including a locking portion that is used as part of a CE-ESI mass spectrometry system in accordance with one potential embodiment of the innovations presented herein.

FIG. 10D shows a potential alternative embodiment including a sheath 1072d and cartridge 1045d having a mechanical stop 1084 to manage movement of sheath 1072d as it retracts and extends. As discussed above, to protect the exposed capillaries affixed to a cartridge, two sliding and lockable sheaths are attached to the separation (separation capillary) and conductive fluid (conductive fluid capillary) sides of a cartridge. The sheaths are capable of moving vertically to alternatively cover and expose the capillary ends for protection of the capillary ends. In one potential embodiment shown in FIG. 10D, the sheaths lock in place to prevent them from prematurely sliding upwards and exposing the capillary to potential damage. In certain embodiments, a separate feature prevents the sheaths from sliding completely off the cartridge.

FIG. 10D thus shows mechanical stop 1084 and flexible finger detent 1082 which connect to prevent the sheath from sliding upward and exposing the capillary to damage. Pivot point 1080 enables flexible finger detent 1082 to move in the direction of flex 1098 shown, so that in some embodiments flexible finger detent 1082 moves away from mechanical stop 1084, and the sheath slides upward to expose the capillary at the appropriate time. In certain embodiments, the cartridge assembly matches a CE instrument such that the locking feature itself is a combination of the mechanical stop 1084 on the sheath and the flexible finger detent 1082 on the cartridge that match an interface with a CE instrument. When the cartridge assembly is installed onto a correctly configured CE instrument, the flexible finger detent 1082 is disengaged allowing the sheath 1072d to slide upwards when pressed against an interface block. The actual method of disengagement can be variable. In certain embodiments the disengagement relies upon a cam lobe and dowel pin arrangement. In such an embodiment, upon removal of the cartridge assembly from the CE system, the sheaths are pulled downwards relative to the cartridge until the locking finger is aligned with the detent on the sheath.

In still further alternative embodiments, alternate means for controlling and managing the protective sheath and locking the sheath into position may be provided. For example, in one alternative embodiment, a spring loaded cartridge is structured with a spring instead of a flexible finger detent with a mechanical stop. Alternatively, magnetic latches, locking mechanisms with a plurality of screws to hold the sheath in place, or an external lock fitted to the outer surface of the sheath may be used. Such embodiments, however, must be designed to prevent arcing with a metal spring during operation, when the voltage operations described herein may result in arcs across gaps within the design parameters shown in the cartridge and sheath embodiments discussed herein.

Figure 11A:
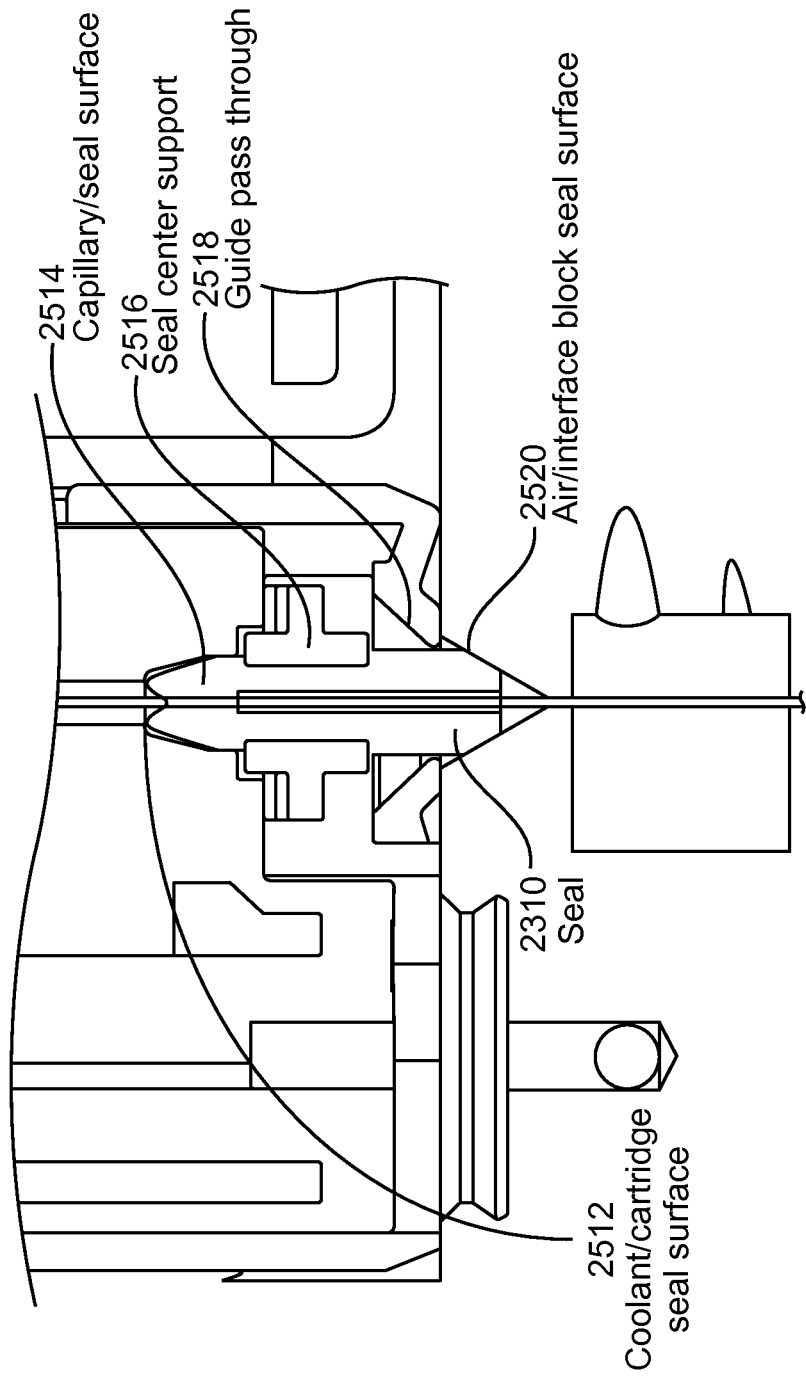
FIG. 11A illustrates a portion of a cartridge assembly including a capillary protection cover (sheath) that is used as part of a CE-ESI mass spectrometry system in accordance with one potential embodiment of the innovations presented herein.

Additional details of alternative embodiments of a cartridge and sheath are disclosed in FIGS. 11A-G. As detailed above, FIG. 10C describes a system including an interface block target 1090 and a capillary interface 1041 with guide features to assist in preventing capillary damage as the sheath is retracted and the capillary extended outside the sheath for use. FIG. 10C shows capillary 1042 in a protected position. FIG. 11A, shows an embodiment in a position with the capillary extended outside of the sheath.

As shown in FIGS. 10A-B, in some embodiments each capillary has a seal surrounding a portion of the capillary within a sheath, such that when the sheath is retracted, the capillary is guided through an interface, and the seal then comes in contact with the interface at the extreme position with the capillary extended outside the sheath. In some embodiments, in order to rinse, fill, or purge a capillary or to inject a sample into a capillary, an air tight seal is required between the capillary and the interface block. The liquid cooling system requires a liquid tight seal between the capillary and cartridge as well. The capillary must be retained within the consumable cartridge to prevent the capillary from pulling out of the assembly. In certain embodiments, the seal must be long enough to pass through a guiding feature in order to be able to fully contact the cartridge, capillary, and interface block at the same time.

The details of one potential embodiment in such a position are shown in FIG. 11A, with seal 2310 in contact with an interface block air/interface block seal surface 2520, the seal passing through guide pass through 2518, and the capillary extending from the capillary seal surface 2514 out through the seal at air/interface block seal surface 2520. Coolant inside the cartridge is blocked from exiting the cartridge at coolant/cartridge seal surface 2512 where the capillary enters the seal 2310 just above capillary/seal surface 2514. Seal center support 2516, that in some embodiments is a part of a seal clip discussed below, supports seal 2310 to prevent excessive lateral deformation which may damage the capillary. The upper portion of the seal thus serves to contain coolant within the cartridge and prevent leaks through the seal where the capillary has been inserted while the lower portion maintains a pressure seal against the interface block.

Figure 11C:
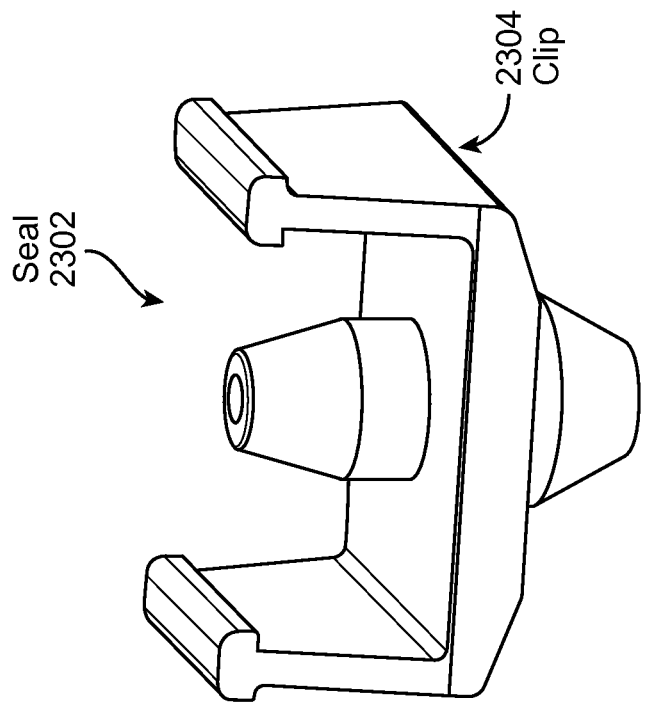
FIG. 11C illustrates a portion of a cartridge assembly including a seal that is used as part of a CE-ESI mass spectrometry system in accordance with one potential embodiment of the innovations presented herein.
Figure 11B:
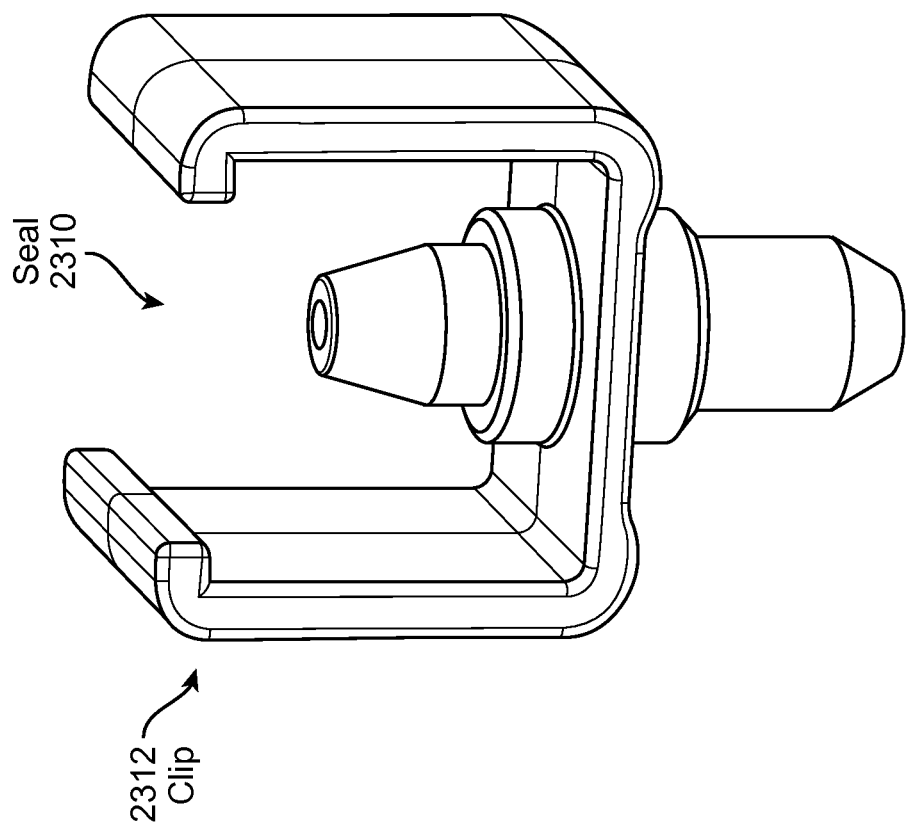
FIG. 11B illustrates a portion of a cartridge assembly including a seal that is used as part of a CE-ESI mass spectrometry system in accordance with one potential embodiment of the innovations presented herein.
Figure 11E:
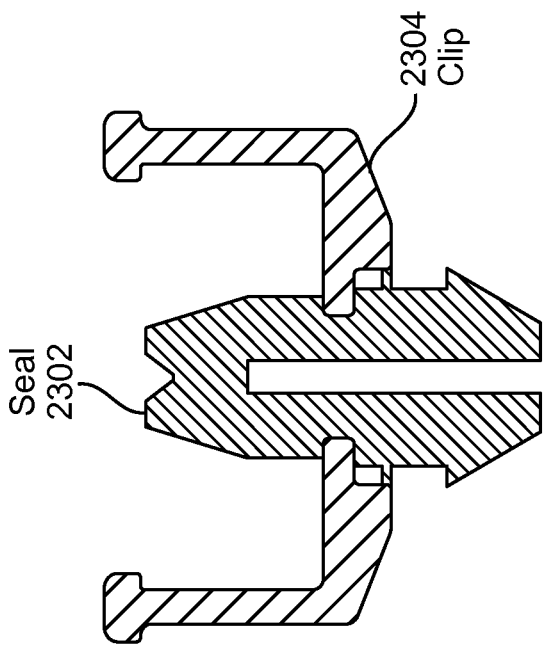
FIG. 11E illustrates a portion of a cartridge assembly including a seal that is used as part of a CE-ESI mass spectrometry system in accordance with one potential embodiment of the innovations presented herein.
Figure 11D:
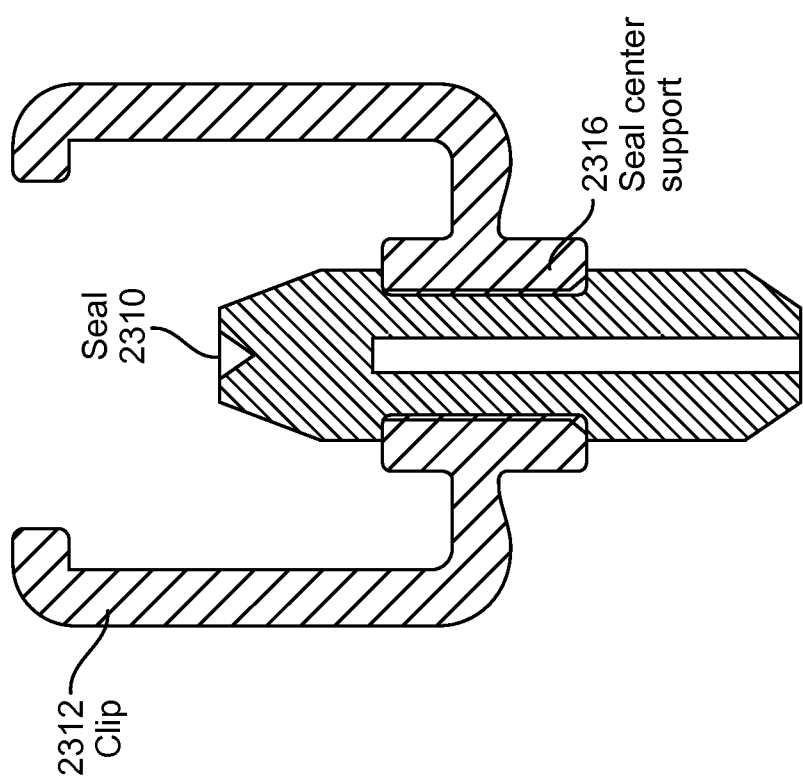
FIG. 11D illustrates a portion of a cartridge assembly including a seal that is used as part of a CE-ESI mass spectrometry system in accordance with one potential embodiment of the innovations presented herein.

Alternative examples of seals are shown in FIGS. 11B, 11C, 11D, and 11E. In FIGS. 11B and 11D, seal 2310 which is the same seal shown in FIG. 11A is detailed. Seal 2310 includes, in some embodiments, a longer seal surface than seal 2302 of FIGS. 11C and 11E, and thus is improved in certain embodiments by a seal center support 2316 which is part of clip 2312. In some embodiments clip 2312 functions to hold the seal 2310 in place in the cartridge when a capillary is inserted in seal 2310. This is especially true since minor forces on a capillary which is inserted in seal 2310 may push seal 2310 within a position inside the cartridge over many uses, and to provide adequate seal surfaces clip 2312 must hold the seal 2310 in the appropriate position. In some embodiments, the clip snaps onto the cartridge to retain the seal against the cartridge. The seal itself is pulled through the clip prior to being installed onto the cartridge. A cylindrical center section supports the long neck of the seal. Two shoulders on the seal are supported by the center section. In combination with each other, a long seal can be implemented that does not buckle under the compression load experienced during cartridge installation.

In certain embodiments, a septum at the top portion of the seal that is pierced by the capillary during the assembly process provides sufficient friction to retain the capillary within the assembly. In alternative embodiments, the septum is placed at other portions of the seal where the seal is in contact with the capillary, or in some embodiments any other suitable method such as an adhesive or additional clip is used to prevent movement of the capillary within seal 2310.

Figure 11F:
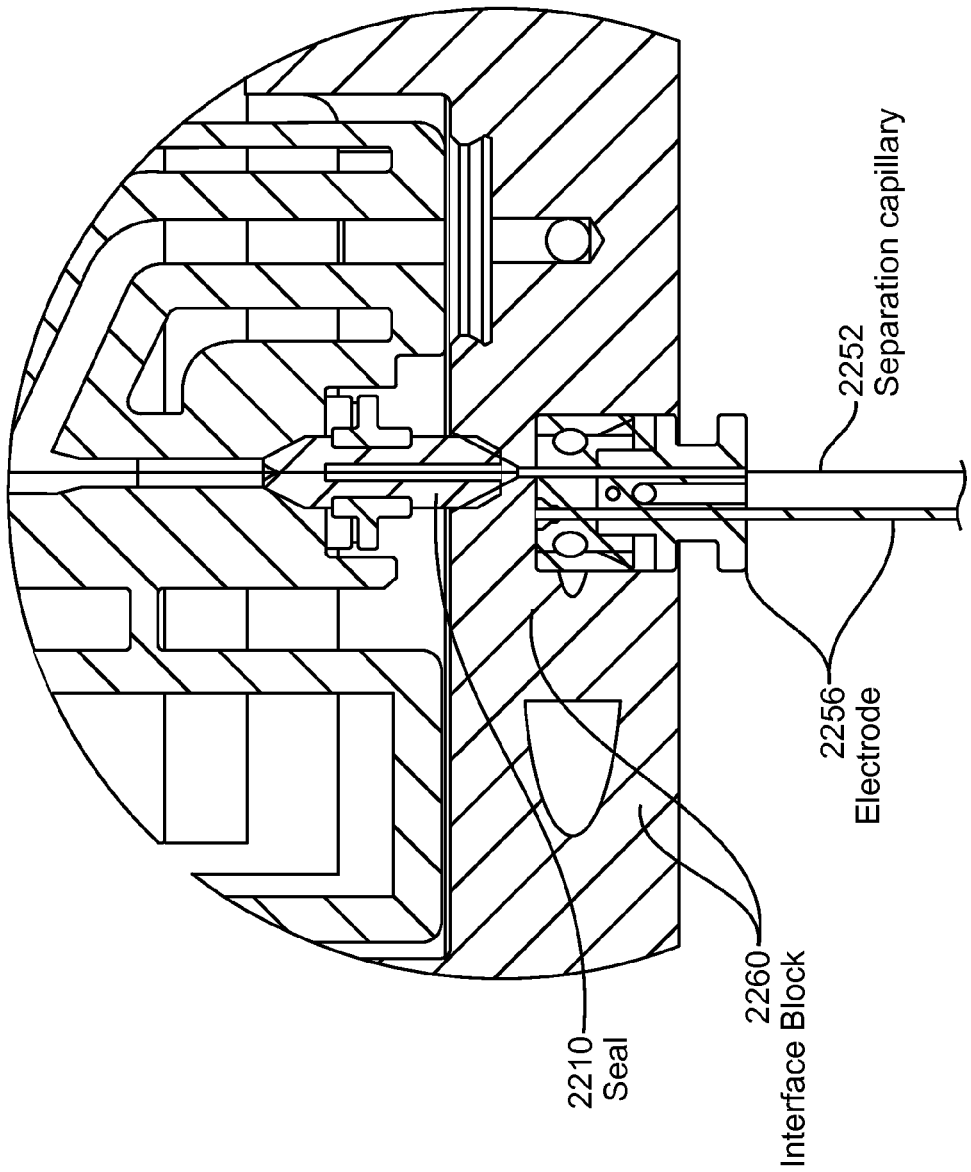
FIG. 11F illustrates a portion of a cartridge assembly including a capillary protection cover (sheath) that is used as part of a CE-ESI mass spectrometry system in accordance with one potential embodiment of the innovations presented herein.

FIG. 11F shows an additional illustration of an embodiment with seal 2210 in a position to interface with interface block 2260 on a side of a cartridge with the separation capillary (sample capillary) 2252 and electrode 2256.

Figure 11G:
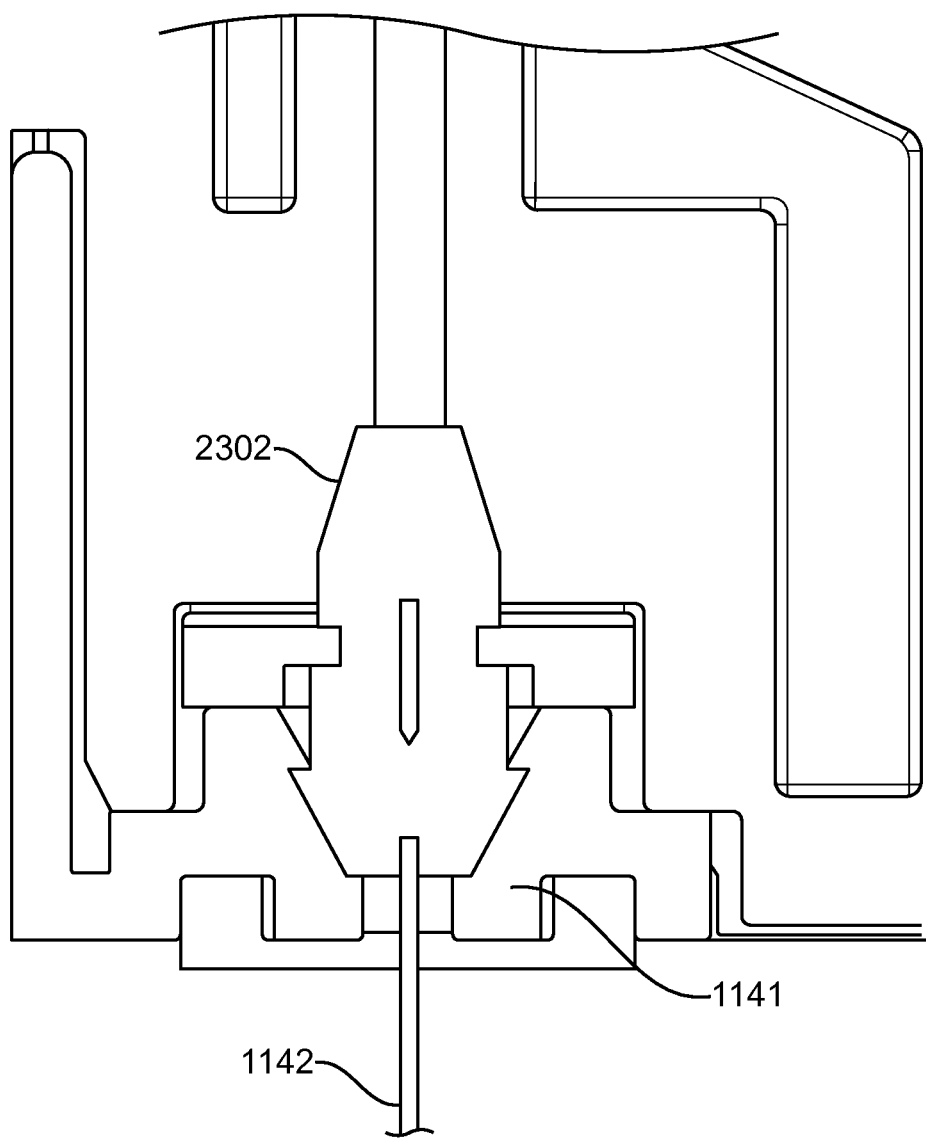
FIG. 11G illustrates a portion of a cartridge assembly including a capillary protection cover (sheath) that is used as part of a CE-ESI mass spectrometry system in accordance with one potential embodiment of the innovations presented herein.

FIGS. 11C, 11E, and 11G show an alternative embodiment of a seal 2302 with clip 2304. Additional detail of a seal 2302 at an interface position in a cartridge is shown in FIG. 11G, with capillary interface 1141 and separation capillary 1142 shown when the associated sheath is retracted, and separation capillary 1142 extends out from the protective sheath. In certain embodiments, the cartridge of FIG. 11G with seal 2302 does not include a capillary guide surface, and seal 2302 simply supports the capillary 1142 as it extends, with the capillary extending through a tube into the target area containing the separation material. In various alternative embodiments, the same type of seal is used on both the conductive fluid side and the separation side of a cartridge, or different types of seals are used on different sides of the cartridge. Similarly, the guide interface in conjunction with an interface block as described above is used on either, both, or neither side of the cartridge in some embodiments.

Figure 12:
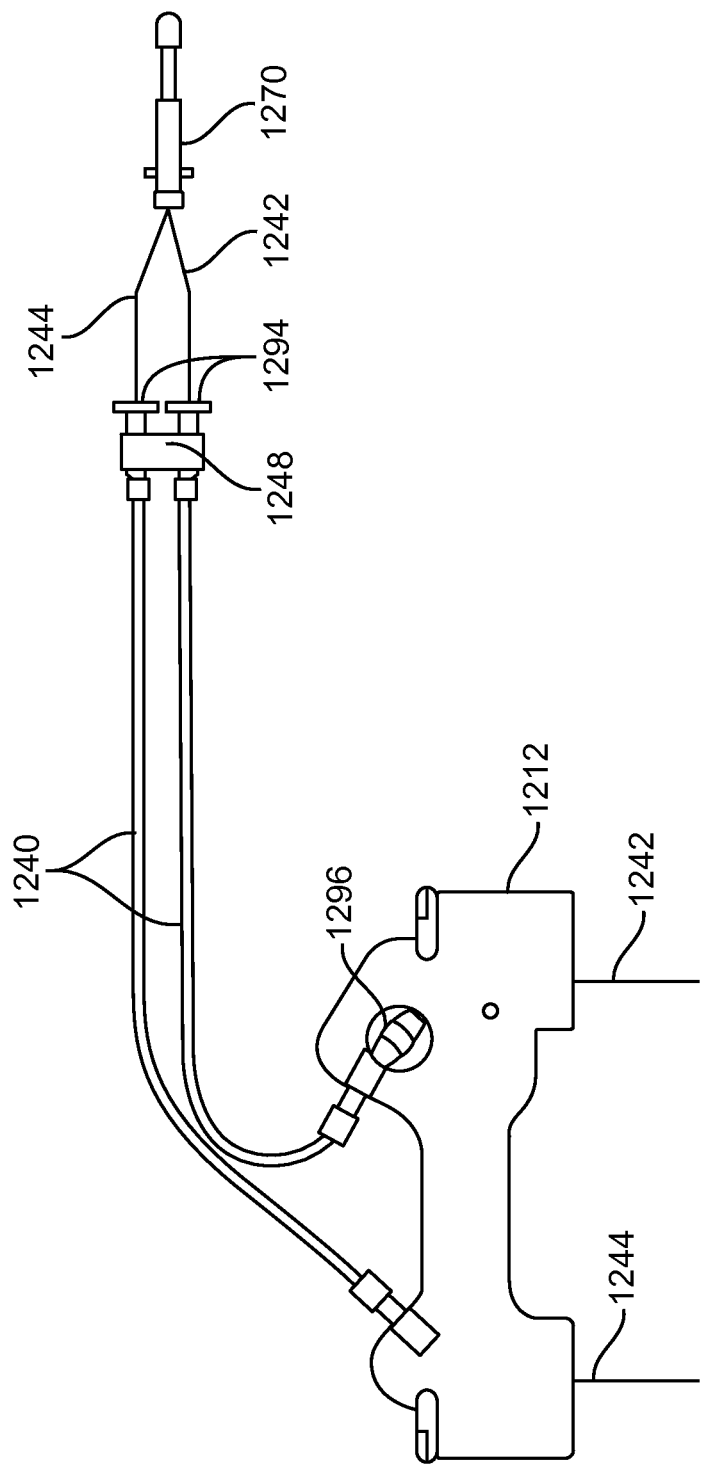
FIG. 12 illustrates a cartridge assembly that is used as part of a CE-ESI mass spectrometry system in accordance with one potential embodiment of the innovations presented herein.
Figure 13:
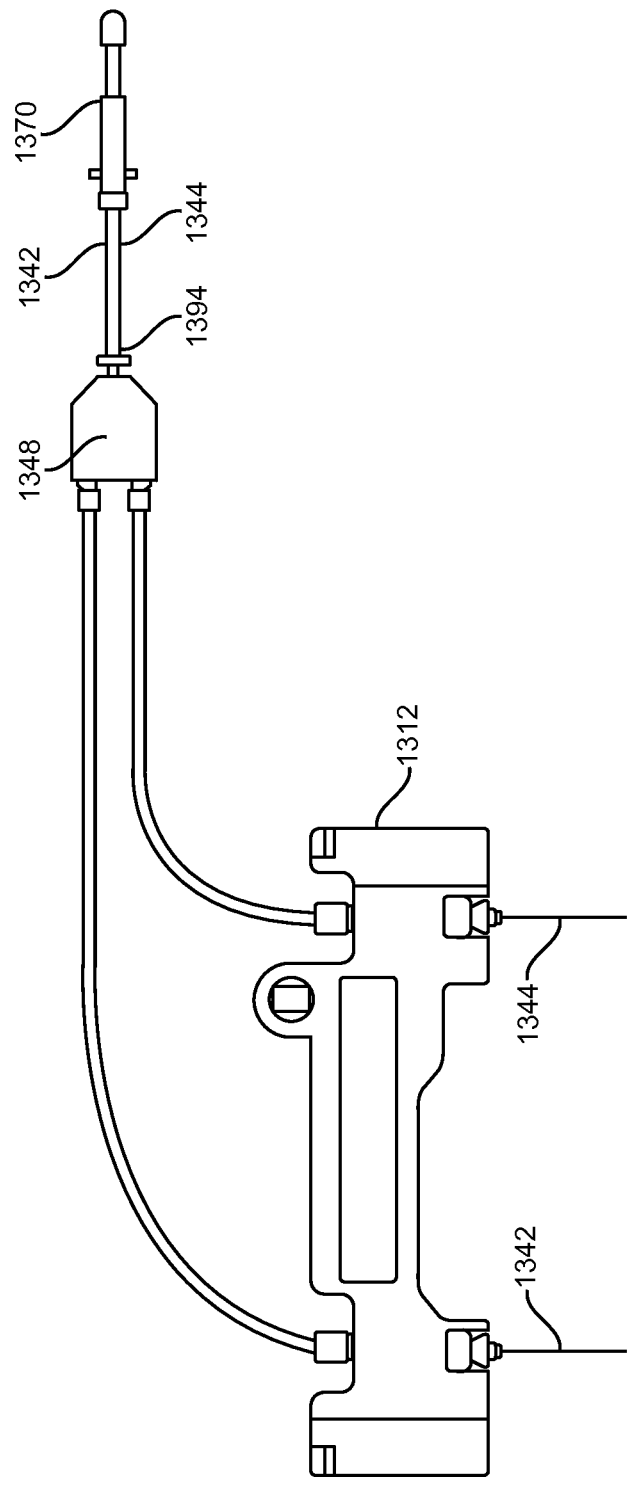
FIG. 13 illustrates a cartridge assembly that is used as part of a CE-ESI mass spectrometry system in accordance with one potential embodiment of the innovations presented herein.
Figure 14:
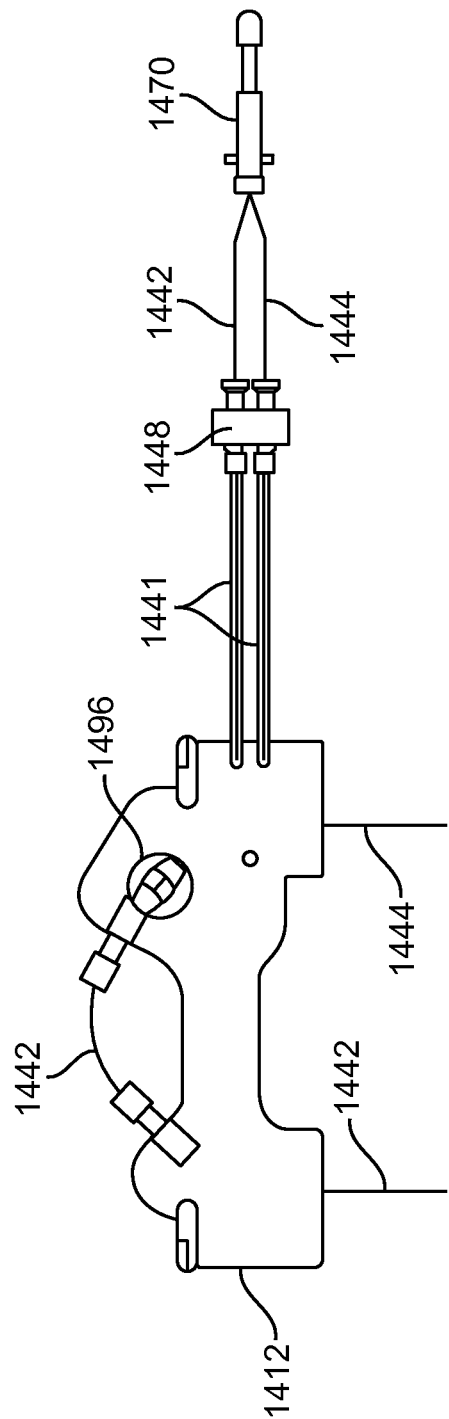
FIG. 14 illustrates a cartridge assembly that is used as part of a CE-ESI mass spectrometry system in accordance with one potential embodiment of the innovations presented herein.

FIGS. 12-14 show various alternative embodiments of a cartridge assembly for use with an improved CE-ESI-MS system. In FIG. 12, the ESI sprayer tipped separation capillary 1242 is at the outlet end of the cartridge 1212 and the conductive fluid capillary 1244 is at the inlet end of the cartridge 1212.

A portion of each capillary (1242 and 1244) is surrounded by a capillary temperature control fluid tube 1240. The temperature control fluid is pumped into the tubes 1240 by the CE system. Fluid enters into the cartridge 1212 from the inlet end (left side of FIG. 12) and exits back into the CE system from the outlet end (right side of FIG. 12). The fluid return block 1248 diverts the temperature control fluid from the inlet tube into the outlet tube. As compared to previously described embodiments, this means that the cooling fluid surrounds a portion of conducting fluid capillary 1244 as the fluid moves toward fluid return block 1248 and the cooling fluid surrounds a portion of separation capillary 1242 as the cooling fluid returns to cartridge 1212 from fluid return block 1248. The CE separation capillary 1242 and the conductive fluid capillary 1244 exit the fluid return block 1248 through sealed fittings 1294. A portion of each of the two capillaries is enclosed in a protective housing 1270 after exiting from the coolant return block 1248. Although not shown here, in some embodiments the whole assembly including coolant tubes 1240 is protected by an enclosure. By design, a user can easily mount the cartridge 1212 on a CE analysis system. In alternative embodiments, the temperature control fluid tubes 1240, the fluid return block 1248, and the capillary protective housing 1270 exit an associated CE analysis system from a side panel that covers a receiving slot for cartridge 1212. The protective housing 1270 in some embodiments then is mounted on a mechanical stage at the inlet of the MS to generate electrospray.

Additionally, cartridge 1212 has a window or optical aperture 1296. This enables the user to utilize an optical detector of a CE analysis system to detect sample during separation as the sample passes through the optical window. The sample then continues on to protective housing 1270 to be input to a mass spectrometer. In alternative embodiments, where use of the optical window is not required, the capillaries 1244 and 1242 in some embodiments switch positions, such that the conductive fluid capillary 1244 passes through window 1296. This does not provide any analysis benefit, but merely allows cartridge 1212 to be used versatilely, that is, in some embodiments with the right hand side (as seen in FIG. 12) of the cartridge housing a portion of conductive fluid capillary 1244 without any negative effects.

The arrangement shown in FIG. 13 is identical to the configuration of FIG. 12 except for a redesigned cartridge 1312, an alternate fluid return block 1348, and the location of the separation and conductive fluid capillaries in each cartridge. Cartridge 1312 is a simpler version of cartridge 1212. It is designed to simplify assembly of the product and save production cost. It does not have a window, which further simplifies the cartridge and reduces costs. FIG. 13 also discloses a different design for the fluid return block 1348 than the fluid return block of FIG. 12. In FIG. 12, the ESI sprayer tipped separation capillary 1242 and the conductive fluid capillary 1244 exit the fluid return block 1248 through two separate sealed fittings 1294. In FIG. 13, the ESI sprayer tipped separation capillary 1342 and the conductive fluid capillary 1344 exit the fluid return block 1348 through one sealed fitting 1394. The capillaries then continue into the sprayer housing 1370.

FIG. 14 shows an additional alternative embodiment for a cartridge assembly. FIG. 14 includes separation capillary 1442, conductive fluid capillary 1444, window 1496, protective tubes 1441, mounting block 1448, and sprayer housing 1470. Cartridge 1412 shows a capillary cartridge similar to cartridge 1212 of FIG. 12 modified such that the ESI sprayer tipped separation capillary 1442 and conductive fluid capillary 1444 exit from the side of the cartridge 1412. This design does not have capillary temperature control fluid tubes. Instead, protective tubes 1441 protect the capillaries 1442 and 1444 from mechanical damage after exiting from the cartridge. The capillaries are loaded into the cartridge 1412 through tubes 1441. The tubes guide the capillaries to appropriate ports of the cartridge 1412. The ESI sprayer tipped separation capillary 1442 passes through the optical aperture 1496. In some embodiments ESI sprayer tipped separation capillary 1442 has an optical capillary window at the cartridge aperture 1496 as described above to enable the user to utilize an optical detector of a CE analysis system to detect sample during separation as it passes through the optical window. The two capillaries pass through a mounting block 1448 which takes the place of the unnecessary fluid return block.

The mounting block 1448 helps to mechanically mount capillaries 1442 and 1444 to the side panel of a CE analysis system as they exit the instrument. In some embodiments the two capillaries are enclosed in a protective housing 1470 after exiting from mounting block 1448.

Although several cartridge assemblies are described above, the innovations presented herein are not limited to the configurations shown previously. Also included is any configuration which comprises a capillary holder which is readily mountable on a CE analysis system wherein the capillary holder includes an at least one retractable portion, an ESI sprayer tipped separation capillary, and a mechanical enclosure for the ESI sprayer tip of the separation capillary wherein the mechanical enclosure includes an at least one retractable portion and wherein the mechanical enclosure is readily mountable on a mass spectrometer to form an electrospray. The capillary temperature control fluid tubes, the fluid return block, the conductive fluid capillary, or a combination thereof are optional depending on the application and the design of the ESI sprayer tip. In some embodiments, the ESI sprayer tipped separation capillary has an optical window with, or optionally without, an integrated optical aperture allowing the separation capillary to interface with an optical detector. In certain embodiments it is preferable to have the optical detection, and thus the optical window, near the inlet of a mass spectrometer, just before the protective ESI sprayer tip housing. However in some embodiments the optical window on the separation capillary is located anywhere along its length. In some embodiments the separation capillary comprises a terminal portion that includes an ESI sprayer tip. In some embodiments the separation capillary comprises a terminal portion that includes a sheathless ESI sprayer tip, a non-limiting example of which is a High Sensitivity Porous Sprayer (HSPS) capillary tip. In some embodiments, the ESI sprayer tip with an associated capillary and the separation capillary are separate capillaries, being connected with each other by a suitable union device.

Figure 15:
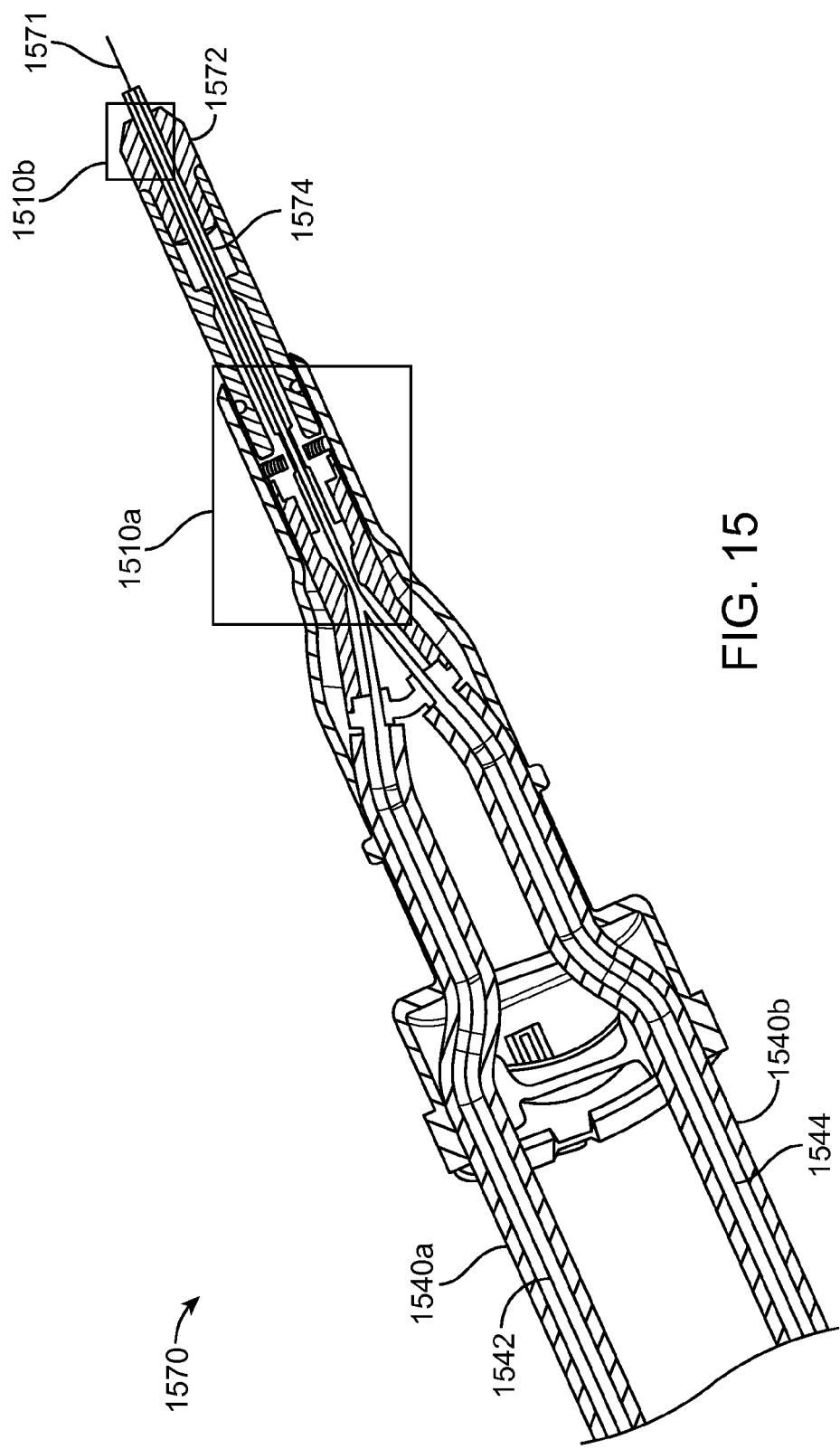
FIG. 15 illustrates an electrospray assembly that is used as part of a CE-ESI mass spectrometry system in accordance with one potential embodiment of the innovations presented herein.

FIG. 15 shows additional details of a sprayer housing 1570. As shown by FIG. 15, separation capillary 1542 with surrounding cooling tube 1540a, and conductive fluid capillary 1544 with surrounding cooling tube 1540b enter the sprayer housing 1570 at the bottom left hand side as shown in the figure. Conductive fluid contact portion 1510a, which is also shown as 1610a in FIG. 16A and described in greater detail in FIG. 17, depicts where the conductive fluid contacts a cylindrical inner surface of an electrically conductive slug (stainless steel slug 1722 of FIG. 17), occupies a cylindrical volume within a needle (needle 1728 of FIG. 17), and contacts an outer cylindrical surface of a portion of the separation capillary that is enclosed within the slug and needle. Conductive fluid contact portion 1510b, which is also shown as conductive fluid contact portion 1610b in FIG. 16A, depicts where the conductive fluid occupying a cylindrical volume within the needle contacts the etched portion of the separation capillary which is contained within the needle.

In certain embodiments with a fragile ESI capillary output such as ESI capillary output 1571 in FIG. 15 which in certain embodiments is an etched capillary tip used with a sheathless (no sheath flow) ESI sprayer, the capillary tip at the output is extremely fragile and susceptible to breaking with minimal contact. This is true in comparison to some non-etched tips and especially in comparison to steel needle assemblies, which provide greater strength but have reduced sensitivity and system resolving power. During use on a mass spectrometer in fragile etched capillary tip embodiments, it is necessary to have the etched capillary tip exposed in order to generate stable ESI flow. Certain embodiments thus use a spring loaded retractable sheath installed onto the housing that secures the etched capillary. In certain of such embodiments, the housing supports the capillary at a location where etching has not been performed, and the etched portion of the capillary is cantilevered from this point out of the housing. The retractable sheath surrounds the etched portion of the capillary, but does not contact the capillary in certain of such embodiments, and a spring holds the sheath in a fully extended position at any point that the assembly is not installed onto an adapter. In some of such embodiments, a feature on the sheath interfaces with the housing and prevents it from being ejected under the spring load. Examples of various embodiments of a retracting protective sheath are described in FIG. 15 and FIGS. 16A, 16B, and 16C.

FIG. 15 also describes retracting protective sheath 1572, sheath assembly 1574, and ESI capillary output 1571. Similar elements are shown in FIG. 16A as retracting protective sheath 1672, sheath assembly 1674, and ESI capillary output 1671. FIG. 15 shows retracting protective sheath 1572 in the retracted position. When sprayer housing 1570 is inserted into an adapter at the input of a mass spectrometer, retracting protective sheath 1572 is pushed back toward the open cavity/slot toward the back of sheath assembly 1574. Thus, the act of inserting the sprayer housing 1570 into the adapter removes the protective sheath 1572 and puts ESI capillary output 1571 in position to deliver separated molecules as electrospray to the mass spectrometer. Thus, ESI capillary output 1571 is a capillary output-proximal end portion of the capillary, with the other end of the ESI capillary being a capillary input-proximal end portion of the capillary.

Figure 16A:
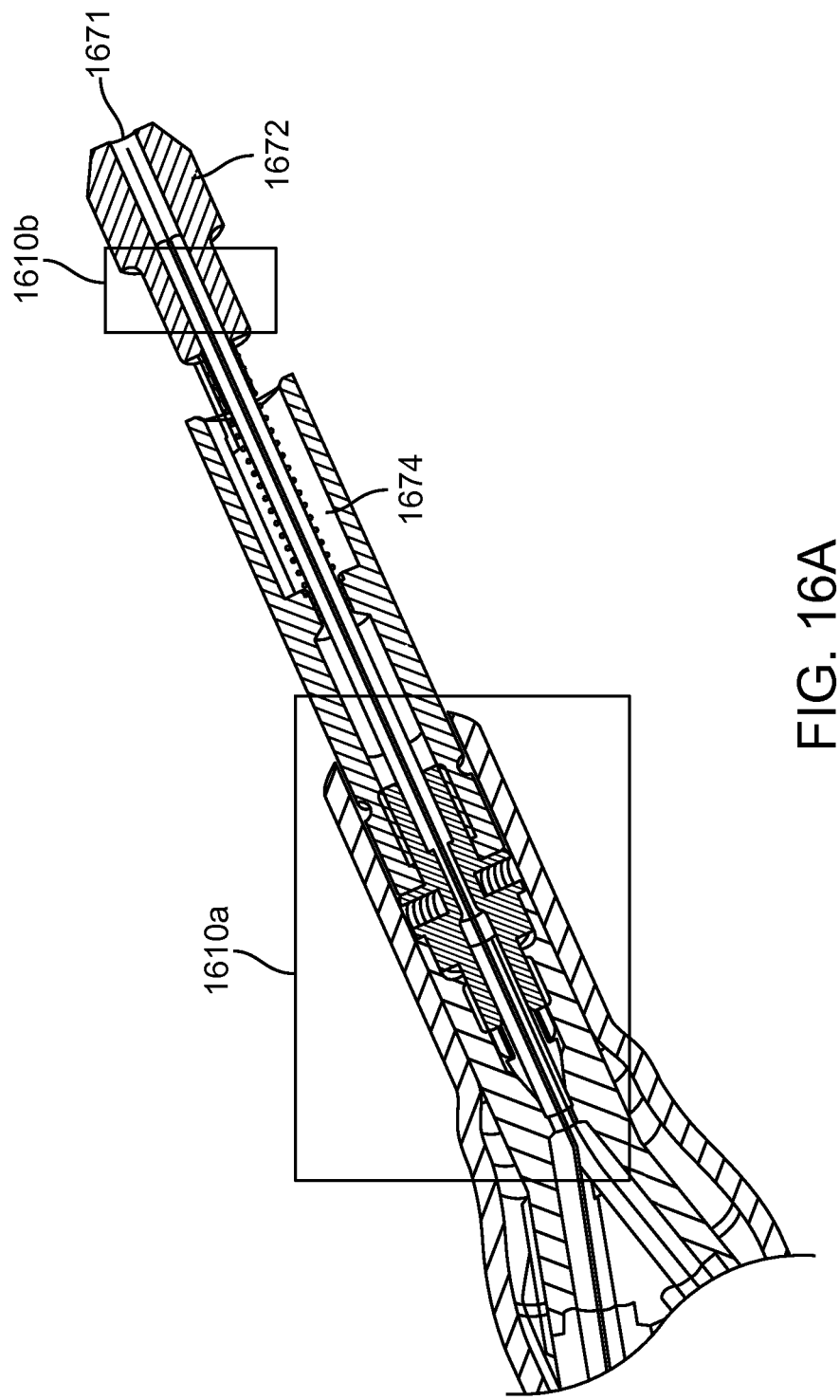
FIG. 16A illustrates an electrospray assembly that is used as part of a CE-ESI mass spectrometry system in accordance with one potential embodiment of the innovations presented herein.
Figure 16B:
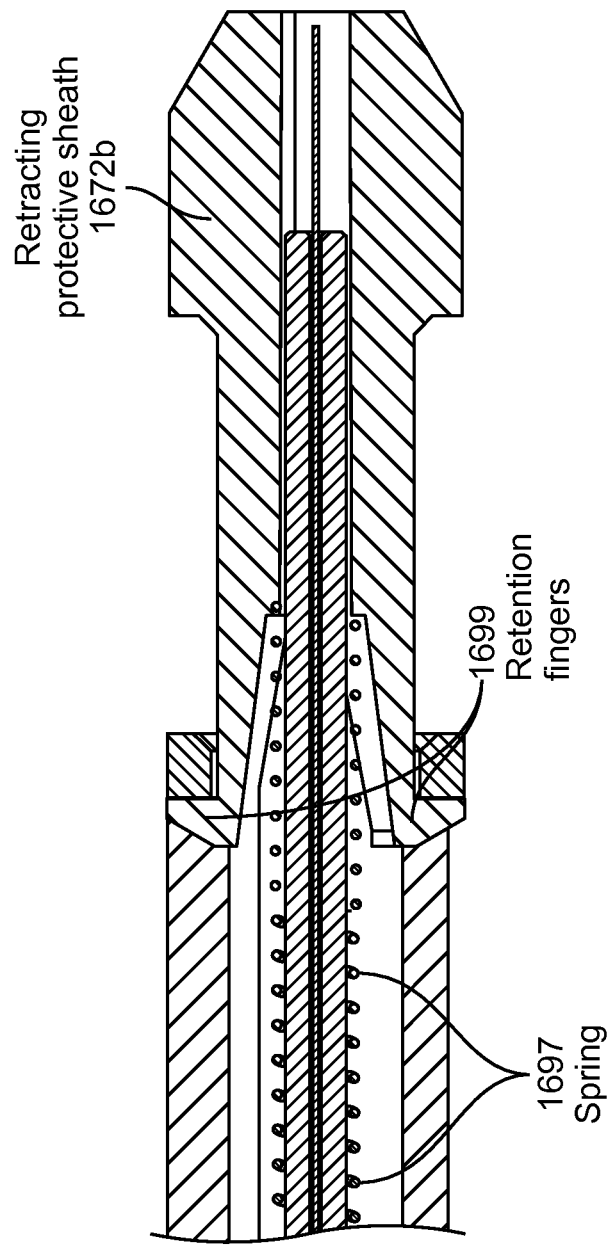
FIG. 16B illustrates an electrospray assembly that is used as part of a CE-ESI mass spectrometry system in accordance with one potential embodiment of the innovations presented herein.
Figure 17:
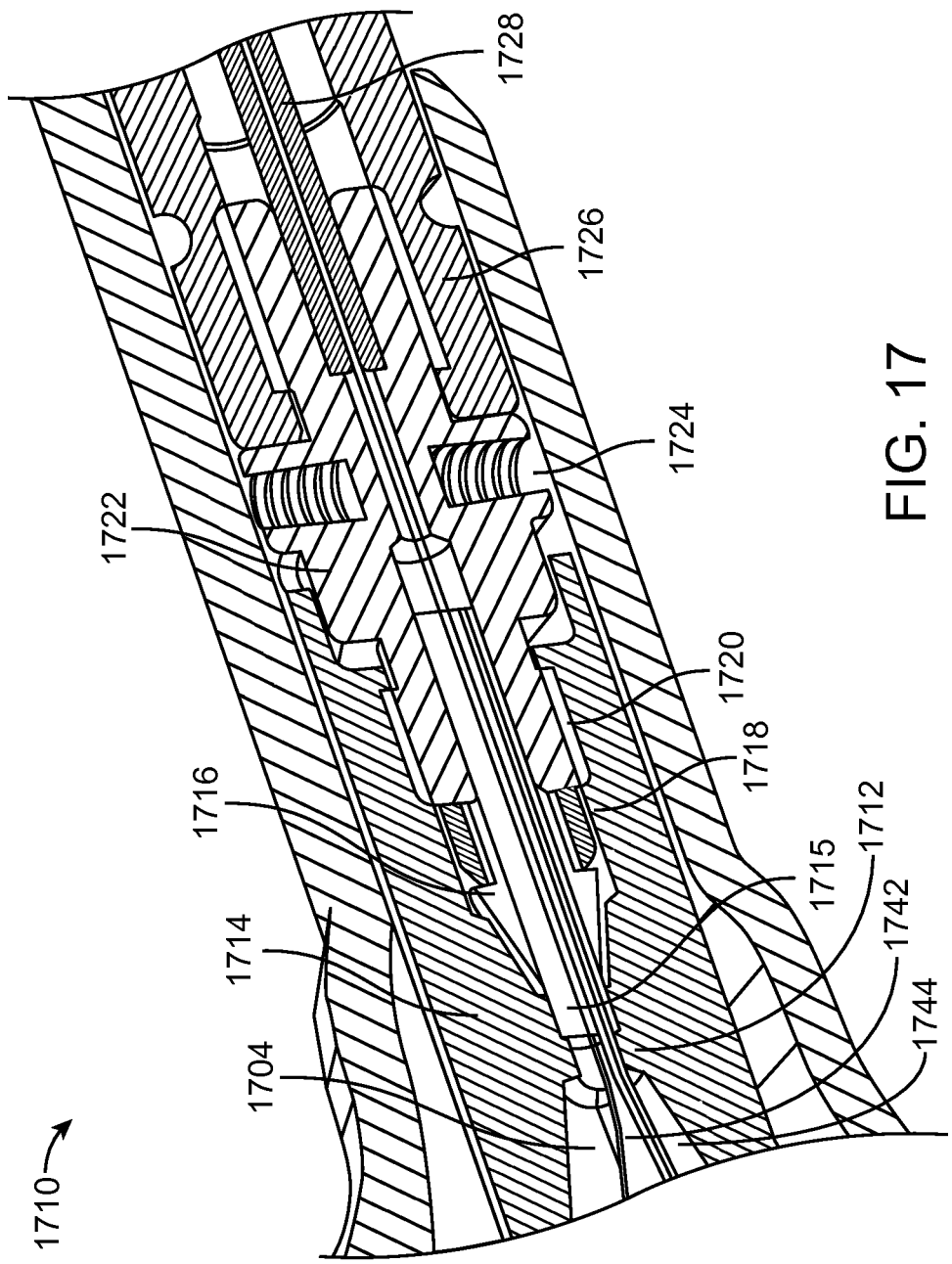
FIG. 17 illustrates an electrospray assembly that is used as part of a CE-ESI mass spectrometry system in accordance with one potential embodiment of the innovations presented herein.

FIGS. 16A, 16B, and 16C show additional details relating to aspects of embodiments including a retracting protective sheath. FIG. 16A shows retracting protective sheath 1672 in the protective position to cover ESI capillary output 1671. In some embodiments sheath assembly 1674 includes a spring or some other mechanism to hold the retracting protective sheath in the protecting position when the sprayer housing is not engaged with an adapter as shown in FIG. 16B.

FIGS. 16B and 16C show an embodiment including a spring 1697 which pushes retracting protective sheath 1672b out into a position where an ESI capillary output is protected by the sheath. In FIG. 16B, retracting protective sheath 1672b is extended, and in FIG. 16C, retracting protective sheath 1672b is retracted. Retention fingers 1699 function in opposition to spring 1697 such that when the retracting protective sheath 1672b is fully extended out into the protective position, retention fingers 1699 prevent the sheath from overextending due to the force of spring 1697. In various other alternative embodiments, the specific arrangements and shapes of the retractable sheath, spring, and housing assembly are arranged in different positions to fulfill the same function. While certain embodiments with an internal spring conserve space, in alternative embodiments, the spring is mounted externally and the sheath is retained internally. In other alternative embodiments, retention fingers are exchanged for other means such as a press fit bushing to hold the sheath on, quarter turn locks, other mechanical stops, or any other such retention means.

FIG. 17 shows conductive fluid contact portion 1710 of a sprayer tip housing for use with an improved CE-ESI-MS system. Conductive fluid contact portion 1710 includes coolant return 1704, separation capillary 1742, conductive liquid capillary 1744, liquid stop deformation portion 1712, coolant manifold 1714, double lumen tube 1715, ferrule 1716, stainless steel ring 1718, coolant manifold threads 1720, stainless steel slug 1722, slug thread 1724, sprayer housing body 1726, and needle 1728.

Coolant manifold 1714 acts with ferrule 1716 to deform double lumen tube 1715 such that the coolant in coolant return 1704 is sealed from leaking further to the right of deformed portion 1712. The capillaries both enter double lumen tube 1715. In some embodiments, the conductive fluid capillary 1744 extends into double lumen tube 1715. In other embodiments, the conductive fluid capillary 1744 extends through double lumen tube 1715. In some embodiments, including the embodiment shown in FIG. 17, the conductive fluid capillary 1744 extends through, but no further than, double lumen tube 1715. However, the separation capillary then enters needle 1728 which directs the capillary to the output of the sprayer housing where it acts as an input to the mass spectrometer. As part of the sprayer housing, sprayer tip housing body 1726 provides further structural support and protection for the separation capillary. In some embodiments slug thread 1724 includes a protruding screw, stud, or other contact that allows a connection to be made with an electrical contact of the adapter to provide the high voltage return connection to an isolated CE power supply. This electrical connection goes from the isolated CE power supply to the adapter, to the screw or electrical contact on the sprayer housing, to the stainless steel slug 1722, to the conductive liquid (from conductive liquid capillary 1744) within slug 1722, to the conductive liquid within needle 1728, and through the etched portion of the separation capillary wherein said etched portion is disposed within the terminal portion of needle 1728 that is nearest the output of the sprayer housing.

In one potential embodiment, sprayer housing body 1726, ferrule 1716, and coolant manifold 1714 are all created from polyether ether ketone (PEEK). In alternative embodiments, other materials that have the characteristic of being insusceptible to temperature, chemicals, or a combination thereof, and that do not present out gassing issues, are used in place of PEEK for any of the described elements of the sprayer housing.

Figure 18:
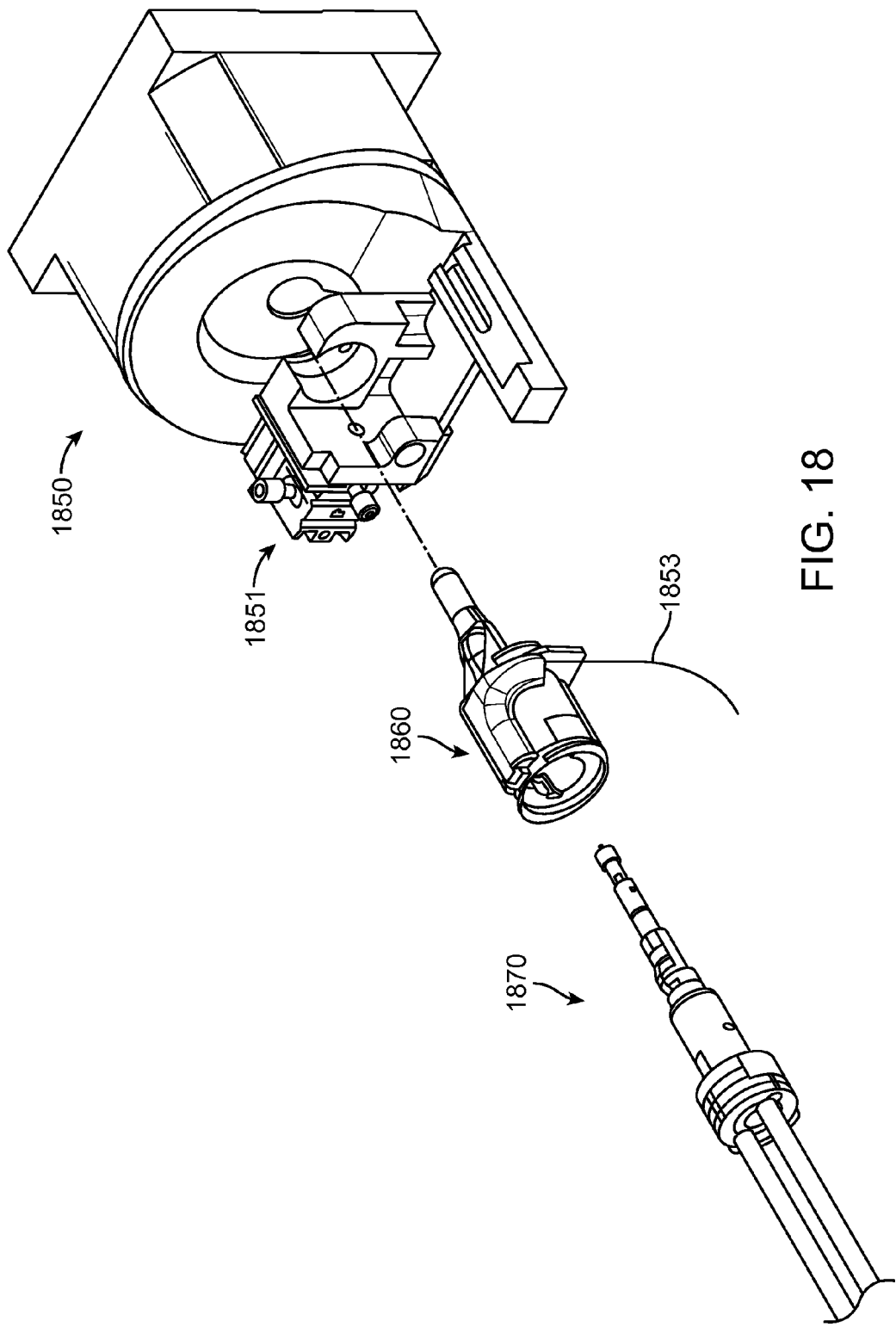
FIG. 18 illustrates an electrospray assembly including an adapter for a specific mass spectrometer that is used as part of a CE-ESI mass spectrometry system in accordance with one potential embodiment of the innovations presented herein.
Figure 19:
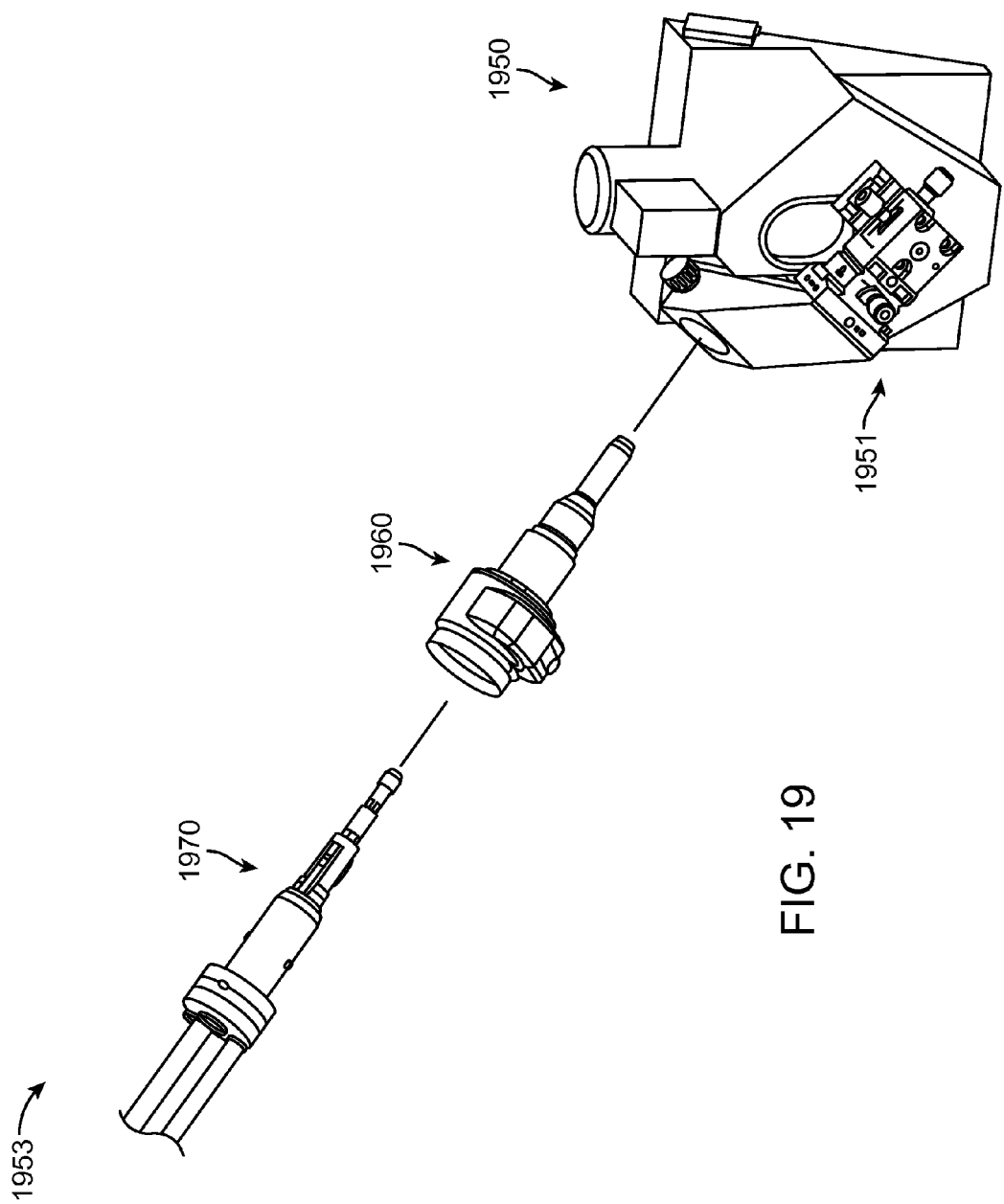
FIG. 19 illustrates an electrospray assembly including an adapter for a specific mass spectrometer that is used as part of a CE-ESI mass spectrometry system in accordance with one potential embodiment of the innovations presented herein.

FIGS. 18 and 19 show two embodiments of a sprayer housing, an adapter, and a mass spectrometer in accordance with certain embodiments of an improved CE-ESI-MS system according to the innovations presented herein. FIG. 18 shows sprayer housing 1870, adapter 1860, and mass spectrometer 1850. As previously described, adapter 1860 in some embodiments is mounted and aligned with mass spectrometer 1850. In some embodiments this attachment is transient and in other embodiments this attachment is long-standing or even permanent. A benefit of various embodiments of the innovations presented herein is the ability to make a complex and/or difficult attachment of the sprayer outlet to mass spectrometer 1850 by housing the sprayer outlet in sprayer housing 1870 which is operably connectable with adapter 1860 which is operably connectable with mass spectrometer 1850 to provide for leaving the adapter 1860 attached so that a much simpler and/or easier connection of the sprayer outlet to the mass spectrometer is sustained (or readily repeated).

As shown in FIG. 18 and described above, electrical connection 1853 is attached to adapter 1860, and enables an electrical connection from a power supply to the separation capillary through a number of elements including the conductive fluid from a conductive fluid capillary when sprayer housing 1870 is inserted into adapter 1860.

In one potential embodiment, adapter 1860 has a first interface for receiving a sprayer housing and a second interface for coupling with a mass spectrometer, with an axial capillary passageway extending from an opening of the first interface to an opening of the second interface. The axial capillary passageway is also referred to as a capillary lumen. The axial capillary passageway is positioned to allow a capillary from the sprayer housing to pass through the axial capillary passageway, out the second interface, and into an input of the mass spectrometer. In certain embodiments, the adapter also has an outer surface and an inner surface, where the inner surface defines at least a portion of the axial capillary passageway. As part of electrical connection 1853, adapter 1860 includes a resistive electrical adapter path from a first section of the outer surface to a first section of the inner surface, where the inner surface is in a position to interface with a resistive electrical path of the sprayer housing, such as slug 1722. When the resistive electrical path of the sprayer housing contacts the first section of the inner surface, a resistive electrical path is created as part of the circuit shown in FIGS. 1, 2B, and 3-6.

Sets of adapters thus are created in some embodiments such that a first adapter and a second adapter have identical or equivalent sprayer housing interface surfaces as part of the inner surface at an input portion of the first interface for each adapter. The second interface for each adapter in such embodiments, however, has differing outer surface areas which match different input topologies for different mass spectrometer devices. In this way, a set of adapters may be placed on different mass spectrometer devices to enable a single sprayer housing to interface with the different mass spectrometer devices.

Among some embodiments sprayer housing 1870 attaches to adapter 1860 in a variety of ways. In one potential embodiment, sprayer housing 1870 includes a protrusion that fits into a hooked groove in adapter 1860. As sprayer housing 1870 is inserted and twisted in adapter 1860, the hook and protrusion lock the pair together along with a spring force from a retracting sprayer sleeve (such as, as a non-limiting example, retracting protective sheath 1672 of FIG. 16A) at the tip of sprayer housing 1870. Other potential embodiments use latches, a plurality of screws used as screw fasteners, or any other acceptable attachment to secure the adapter 1860 with sprayer housing 1870.

Further, FIG. 18 shows x, y, z adjustment control 1851. Adjustment control 1851 allows fine adjustments to the electrospray input position to be made when calibrating the system for use. With sufficiently high tolerances on the interfaces between sprayer housing 1870 and adapter 1860, alignment and measurements are equivalent in some embodiments to calibrations made without sprayer housing 1870 and adapter 1860, with much lower connection time, and much greater ease of connection, once adapter 1860 is initially installed. In some embodiments, x, y, z adjustment control 1851 is controlled electronically using an electronic control system, or is manually adjustable by a user, or both. In various embodiments, x, y, z adjustment control 1851 mechanically adjusts the electrospray input position using adjustable screws which move the input position when the screw is rotated. Alternately, electronic, micro-electronic systems (MEMS), hydraulic, magnetic, or any other means are used in some embodiments to position the input as part of adjustment control 1851.

FIG. 19 shows another alternative embodiment including sprayer housing 1970, adapter 1960, and mass spectrometer 1950, with electrical connection 1953 and x, y, z adjustment control 1951. Although there are various different mass spectrometry systems with differing input connection requirements such as MS 1950 and MS 1850 of FIG. 18, the use of an adapter such as adapter 1960 and adapter 1860 of FIG. 18, respectively, enables uniform sprayer housing 1970 (1870 of FIG. 18) to interface with such different mass spectrometers, or any other mass spectrometer having an appropriately created adapter. This provides a benefit where the high use and fragile capillary components that are most likely to break are disposed so as to be compatible across systems in an easy to use interface, such that cartridge assemblies may be used across systems when, as a non-limiting example, a capillary is broken or some other part of a cartridge assembly is worn or non-functional.

In certain embodiments, a sprayer housing includes a protective sheath similar to retracting protective sheath 1672 shown in FIG. 16A and to 1672b shown in FIGS. 16B-C. In such embodiments, an etched tip that is extremely fragile and subject to damage during connection to, or during removal from, a MS device is protected. In some of such embodiments, the protective sheath 1672 (or 1672b) and a retention means such as retention fingers 1699 are specifically designed to match one side of an adapter such as adapter 1860 in FIG. 18 or adapter 1960 in FIG. 19. In such embodiments, the adapter is inserted into the MS device, accommodating significant adjustments and alignments without risk of damage to the fragile etched tip of a capillary.

Once the adapter is aligned, risk of damage to the etched capillary tip is significantly reduced, since the motion of insertion into the adapter is specifically designed to minimize the chance of a fragile etched capillary tip impacting a surface of the adapter. In some embodiments this is done by specifically designing the spring force from spring 1697, the surface and motion of the retracting protective sheath 1672 (or 1672b), and the restriction of retention fingers 1699 to match an associated adapter. Similarly, in some embodiments the maximum extension of an etched capillary tip is designed with the adapter, to fix the extension of an etched capillary tip outside of a sheath 1672 (or 1672b) in retracted position. Then, when a sprayer housing with a protective sheath is inserted into an adapter, the spring 1697 compresses and the retracting protective sheath 1672 (or 1672b) retracts so the etched tip of the capillary extends through the adapter and into the input of the MS device.

A use of an adapter specifically matched to a sprayer housing and retracting protective sheath 1672 (or 1672b) enables a finely managed movement of the fragile etched portion of a capillary into (and/or out of) the MS device. A single type of adapter such as, as a nonlimiting example, adapter 1860 in FIG. 18 or adapter 1960 in FIG. 19 on multiple MS devices thus allows multiple different MS devices to be used with one or more sprayer housings specifically designed for an adapter on the MS devices to minimize risk of damage to the tip of an etched capillary while enabling the flexibility of moving the sprayer to different MS devices.

FIG. 20 provides a schematic illustration of one embodiment of a computer system 2000 that in some embodiments is used with aspects of an improved CE-ESI-MS system, as described herein, and/or functions, for example, as various parts of capillary electrophoresis controller 110, mass spectrometer controller 160, CE analysis system 130, power supply 120, or mass spectrometer 150 of FIG. 1. In some embodiments computer system 2000 is usable for any component that requires control or electronic communication. It should be noted that FIG. 20 is meant only to provide a generalized illustration of various components, any one or more of which in some embodiments is (are) utilized, as appropriate. FIG. 20, therefore, broadly illustrates how individual system elements are implemented in a relatively separated fashion in some embodiments or in a relatively more integrated manner in other embodiments.

The computer system 2000 is shown comprising hardware elements that in some embodiments are electrically coupled via a bus 2005 (or are otherwise in communication, as appropriate). In some embodiments the hardware elements include one or more processors 2010, including, without limitation, one or more general-purpose processors and/or one or more special-purpose processors (such as digital signal processing chips, graphics acceleration chips, and/or the like); one or more input devices 2015, which in some embodiments include, without limitation, a mouse, a keyboard, and/or the like; and one or more output devices 2020, which in some embodiments include, without limitation, a display device, a printer, and/or the like.

In some embodiments the computer system 2000 further includes (and/or is in communication with) one or more storage devices 2025, which in some embodiments comprise, without limitation, local and/or network accessible storage and/or in some embodiments include, without limitation, a disk drive, a drive array, an optical storage device, a solid-state storage device such as a random access memory ("RAM") and/or a read-only memory ("ROM"), which in some embodiments is programmable, flash-updateable, and/ or the like. In some embodiments the computer system 2000 also includes a communications subsystem 2030, which in some embodiments includes, without limitation, a modem, a network card (wireless or wired), an infra-red communication device, a wireless communication device, and/or chipset (such as a Bluetooth® device, an 802.11 device, a WiFi device, a WiMax device, cellular communication facilities, etc.), and/or the like. The communications subsystem 2030 in some embodiments permits data to be exchanged with a network (such as the network described below, to name one non-limiting example), and/or any other devices described herein. In many embodiments, the computer system 2000 further comprises a working memory 2035 or additional memory systems, which in some embodiments include a RAM or ROM device, as described above.

In some embodiments the computer system 2000 also comprises software elements which in some embodiments comprise computer programs of the innovations presented herein, and/or are designed to implement methods of said innovations and/or configure systems of said innovations. Merely by way of non-limiting example, one or more procedures described with respect to the method(s) discussed above in some embodiments is (are) implemented as code and/or instructions executable by a computer (and/or a processor within a computer). In some embodiments a set of these instructions and/or code is (are) stored on a computer readable storage medium, such as the storage device(s) 2025 described above. In some embodiments, the storage medium is incorporated within a computer system, such as the system 2000. In other embodiments, the storage medium is separate from a computer system (i.e., a removable medium, such as a compact disc, etc.), and/or provided in an installation package, such that the storage medium in some embodiments is used to program a general purpose computer with the instructions/code stored thereon. In some embodiments these instructions take the form of executable code, which is executable by the computer system 2000 and/or in some embodiments takes the form of source and/or installable code, which, upon compilation and/or installation on the computer system 2000 (e.g., using any of a variety of generally available compilers, installation programs, compression/decompression utilities, etc.), then takes (take) the form of executable code.

It will be apparent to those skilled in the art that substantial variations are in some embodiments made in accordance with specific requirements. For example, in some embodiments customized hardware also is used, and/or particular elements are implemented in hardware, software (including portable software, such as applets, etc.), or both. Further, connection to other computing devices such as network input/output devices is employed in some embodiments.

The terms "machine-readable medium" and "computer readable medium", as used herein, refer to any medium that participates in providing data that causes a machine to operate in a specific fashion. In an embodiment implemented using the computer system 2000, various machine-readable media are involved in providing instructions/code to processor(s) 2010 for execution and/or are used to store and/or carry such instructions/code (e.g., as signals). In many implementations, a computer readable medium is a physical and/or tangible storage medium. Such a medium takes many forms among various embodiments, including but not limited to, non-volatile media, volatile media, and transmission media. Non-volatile media includes, for example, optical or magnetic disks, such as the storage device(s) 2025. Volatile media includes, without limitation, dynamic memory, such as working memory shown as working memory 2035 in FIG. 20. Transmission media includes coaxial cables, copper wire, and fiber optics, antenna, including wires that comprise the bus 2005, as well as various components of the communications subsystem 2030 (and/or media by which the communications subsystem 2030 provides communication with other devices). Hence, transmission media also in some embodiments take the form of waves (including, without limitation, radio, acoustic, and/or light waves, such as those generated during radio-wave and infra-red data communications).

Various forms of machine-readable media are involved in some embodiments in carrying one or more sequences of one or more instructions to the processor(s) 2010 for execution. Merely by way of non-limiting example, the instructions in some embodiments are initially carried on a magnetic disk and/or optical disc of a remote computer. In some embodiments a remote computer loads the instructions into its dynamic memory and sends the instructions as signals over a transmission medium to be received and/or executed by the computer system 2000. These signals, which are in some embodiments in the form of electromagnetic signals, acoustic signals, optical signals, and/or the like, are all non-limiting examples of carrier waves on which instructions are encoded, in accordance with various embodiments of the invention.

The communications subsystem 2030 (and/or components thereof) in some embodiments will receive the signals, and the bus 2005 then in some embodiments carries the signals (and/or the data, instructions, etc., carried by the signals) to the working memory 2035, from which the processor(s) 2010 retrieve(s) and execute(s) the instructions.

Sheathless Interface Capillary

Capillary electrophoresis (CE) is an intrinsically low flow separation technique and includes, but is not limited to, Capillary Zone Electrophoresis (CZE; also known as free-solution CE [FSCE]), Capillary Gel Electrophoresis (CGE), Capillary Isoelectric Focusing (CIEF), Isotachophoresis (ITP), Electrokinetic Chromatography (EKC), Micellar Electrokinetic Capillary Chromatography (MECC OR MEKC), Micro Emulsion Electrokinetic Chromatography (MEEKC), Non-Aqueous Capillary Electrophoresis (NACE), and Capillary Electrochromatography (CEC).

Electroosmotic flow (EOF), also known as electroosmosis, is bulk fluid motion when an electric field is applied across a capillary or microchannel. The velocity of this motion is proportional to the applied electric field and is dependent on both the material used to construct the microchannel and the solution in contact with the microchannel wall. This motion results from electrical forces acting on ions in an electrical double layer (Debye Layer), a thin layer of ions that is located near a wall exposed to an aqueous solution. EOF can occur in, for example, natural unfiltered water, solutions of electrolye, and buffered solutions. EOF may be operative in chemical separation techniques, notably CE. For example, in CE a capillary column may comprise silica with silanol groups exposed on a channel surface of a tube wall. The exposed silanol groups are ionized above pH 3, thereby creating a negatively charged inner capillary surface. Cations present in ionic solutions will migrate toward the negatively charged wall forming a Debye Layer. Generation of an electrical potential across the column causes cations to migrate towards the cathode. EOF results as the solvated cations clustered at the capillary walls drag the bulk solution in tow towards the cathode during a CE separation. Generally, EOF of a buffer or electrolyte solution is greater than that of the electrophoretic flow of the analytes during a CE separation process.

A CE process can be coupled with an electrospray ionization-mass spectrometry (ESI-MS) process using a sheath flow interface, a split-flow interface, or a sheathless interface. Sheathless interface technology has been limited by a problem. Historically, it has been thought that significant EOF is needed to successfully couple CE and ESI-MS using a sheathless interface. For example, it has been thought to be impossible to use neutrally coated separation capillaries in a sheathless interface of a CE-ESI-MS system. As a result, most studies have reported the use of a positively charged capillary, which can generate a stable and strong EOF at acidic pH. In this context, using acidic pH, the potential interaction between analytes (positively charged at acidic pH) and the surface of the capillaries (positively charged as well) can be avoided. It is a finding of the innovations presented herein that, contrary to such expectation, significant EOF is not needed for sheathless interface coupling of a CE process and an ESI-MS process when using a separation capillary tube comprising a channel, a channel surface of a tube wall, and an etched capillary outlet-proximal end portion of a tube wall wherein the etched capillary outlet-proximal end portion of a tube wall of the separation capillary tube is porous to a flow of an electrical charge, and wherein the channel surface of a tube wall of the separation capillary tube underlies a coating layer proximal to the channel surface of a tube wall and a coating layer distal to the channel surface of a tube wall.

Reduction of flow with ESI into the nanoflow region has been reported to improve assay sensitivity and reduce ion suppression with ESI-MS. CE-ESI-MS performance parameters that are significantly improved as a result of the innovations presented herein include, but are not limited to: (a) an ability to generate a stable ESI at an ultra-low flow rate, upstream from an ESI process, of less than or equal to 20 nL/min, (b) an orders of magnitude enhancement of detection sensitivity into the femto-, atto-, or zepto-mole range (depending on selected analyte and mass spectrometer), (c) a decrease of ion suppression phenomenon, (d) an EOF that can be reduced to less than $1 \times 10^{-7}$ cm$^2 \cdot$V$^{-1} \cdot$S$^{-1}$, and (e) a peak capacity having a value of 200 or more.

Figure 21:
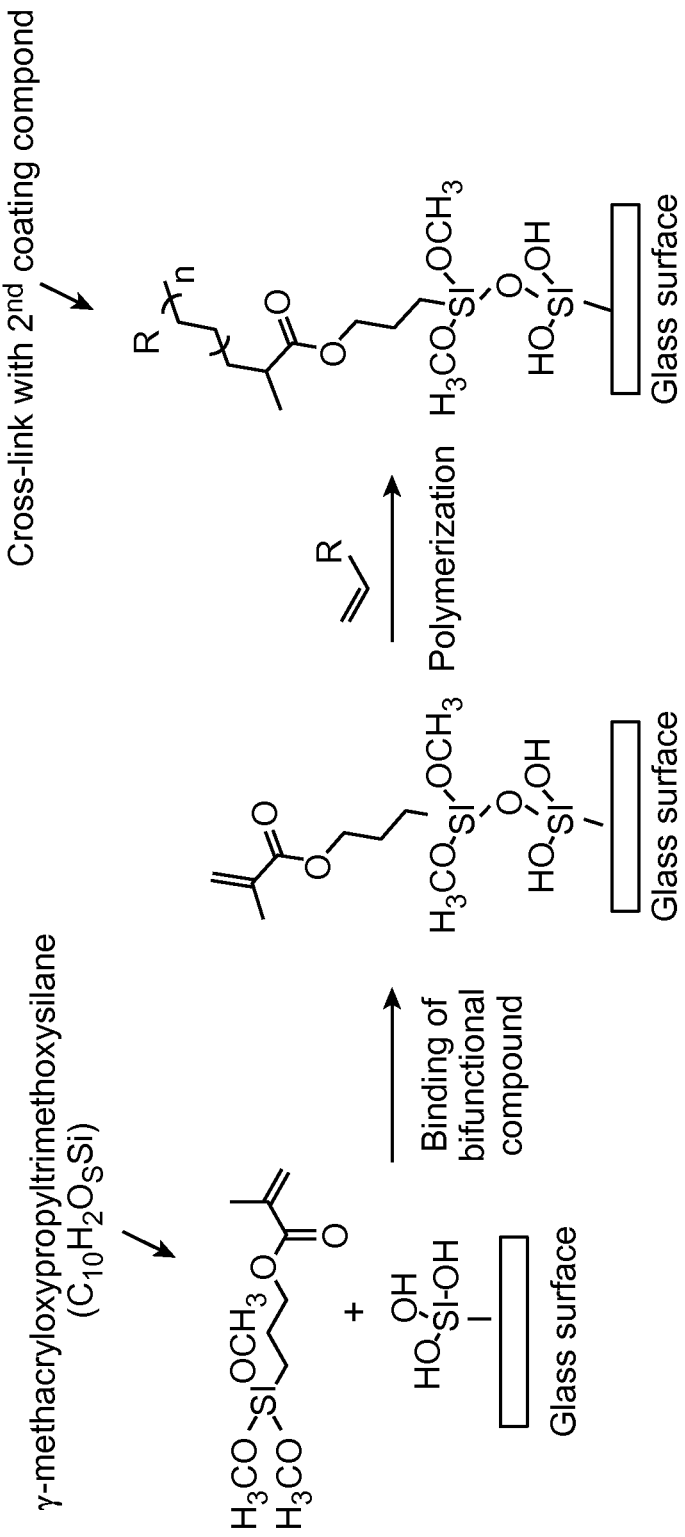
FIG. 21 illustrates a diagram of one potential implementation of a channel surface coating of a separation capillary tube useful as a sheathless interface for coupling a CE process and an ESI-MS process.

FIG. 21 provides a non-limiting example of a separation capillary tube that is useful with a sheathless interface for coupling a CE process and an ESI-MS process. A channel surface (glass surface) of a tube wall of a bare fused silica separation capillary tube is represented. The separation capillary tube may have dimensions comprising, as a non-limiting example, 30 μm inner diameter (i.d.)×150 μm outer diameter (o.d.). In another non-limiting example, the separation capillary tube may have dimensions comprising 30 μm i.d.×360 μm o.d. Such cross-sectional dimensions are in some embodiments combined with a length dimension of 100 cm or of 110 cm, as non-limiting examples. Silica groups (—Si(OH)$_3$) of said channel surface (glass surface) contact the hydrophilic bifunctional compound γ-methacryloxypropyltrimethoxysilane through a first covalent bond, and γ-methacryloxypropyltrimethoxysilane also contacts a second coating compound, cross-linked linear polyacrylamide, by a second covalent bond. Such capillary tubes comprising this two-layer coat are stored either in a dry condition or in a MES/citrate buffer without spermine.

An example of the innovations presented herein is the OptiMS Neutral Surface Cartridge (30 μm i.d.×100 cm total length) sold by Beckman Coulter, Inc. which includes an implementation of the separation capillary tube that is useful as a sheathless interface for coupling a CE process and an ESI-MS process. The OptiMS Neutral Surface Cartridge is used in the CESI 8000 High Performance Separation - ESI Module that also is sold by Beckman Coulter, Inc. and that is designed for mass spectrometry applications that include, but are not limited to, analysis of charged and polar molecules. It consists of a CESI cartridge coupled with an OptiMS sprayer housing. The assembly includes a temperature controlled separation capillary tube (30 μm i.d.×100 cm total length). Each capillary end is protected by a self-retracting housing.

In some embodiments of the innovations herein, the etched capillary outlet-proximal end portion of a tube wall of the separation capillary tube that is useful as a sheathless interface for coupling a CE process and an ESI-MS process comprises an inner tube diameter that does not taper or that has a constant value. In some embodiments the etched capillary outlet-proximal end portion of the separation capillary tube wall has a wall thickness of less than 10 μm. In some embodiments the etched capillary outlet-proximal end portion of the separation capillary tube wall has a wall thickness of 5 μm, or of about 5 μm. In some embodiments, the coating layer proximal to the channel surface of a tube wall comprises a hydrophilic bifunctional compound covalently bound to said channel surface of a tube wall. In some embodiments, the hydrophilic bifunctional compound is selected from the group consisting of γ-methacryloxypropyltrimethoxysilane, β-methacryloxypropyltrimethoxysilane, α-methacryloxypropyltrimethoxysilane, (3-glycidyloxypropyl) trimethoxysilane, 3-(trimethoxysilyl)propyl acrylate, 3-(trimethoxysilyl)propyl methacrylate, vinyltrimethoxysilane, vinyltriacetoxysilane, vinyltri(β-methoxyethoxy)silane, and vinyltrichlorosilane. In some embodiments, the hydrophilic bifunctional compound is γ-methacryloxypropyltrimethoxysilane.

In some embodiments, the coating layer distal to the channel surface of a tube wall of the separation capillary tube that is useful with a sheathless interface for coupling a CE process and an ESI-MS process comprises a surface that contacts an electrolyte solution during an electrophoresis process. It is this surface that contacts contents of the channel (e.g. electrolyte solution, buffered solution, water) during a CE process. In some embodiments, the surface that contacts an electrolyte solution during an electrophoresis process is a neutral surface. In some embodiments, the neutral surface comprises cross-linked linear polyacrylamide. In some embodiments, the neutral surface comprises cross-linked linear polyacrylamide that is covalently bound. In some embodiments, the neutral surface comprises cross-linked linear polyacrylamide that is covalently bound with the hydrophilic bifunctional compound that is covalently bound to the channel surface of a tube wall.

In some embodiments, the separation capillary tube that is useful as a sheathless interface for coupling a CE process and an ESI-MS process comprises, during its operation as a component of a sheathless interface of a CE process, an electroosmotic flow (EOF) having a value less than or equal to $1 \times 10^{-7}$ cm$^2 \cdot$V$^{-1} \cdot$S$^{-1}$. In some embodiments, the separation capillary tube comprises, during its operation as a component of a sheathless interface of a CE process, an EOF having a value less than or equal to $1 \times 10^{-6}$ cm$^2 \cdot$V$^{-1} \cdot$S$^{-1}$. In some embodiments, the separation capillary tube comprises, during its operation as a component of a sheathless interface of a CE process, an EOF having a value less than or equal to $1 \times 10^{-5}$ cm$^2 \cdot$V$^{-} \cdot$S$^{-1}$.

In some embodiments, the separation capillary tube that is useful as a sheathless interface for coupling a CE process and an ESI-MS process comprises, during its operation as a component of a sheathless interface of a CE process, a sensitivity having a value that is less than or equal to 1 femtomole. In some embodiments, the separation capillary tube comprises, during its operation as a component of a sheathless interface of a CE process, a sensitivity having a value that is less than or equal to 10 attomoles. In some embodiments, the separation capillary tube comprises, during its operation as a component of a sheathless interface of a CE process, a sensitivity having a value that is less than or equal to 100 zeptomoles.

In some embodiments, the separation capillary tube that is useful as a sheathless interface for coupling a CE process and an ESI-MS process comprises, during its operation as a component of a sheathless interface of a CE process, a flow rate upstream from an ESI process having a value that is less than or equal to 10 nL/min. In some embodiments, the separation capillary tube comprises, during its operation as a component of a sheathless interface of a CE process, a flow rate upstream from an ESI process having a value that is less than or equal to 100 nL/min.

In some embodiments, the separation capillary tube that is useful as a sheathless interface for coupling a CE process and an ESI-MS process comprises, during its operation as a component of a sheathless interface of a CE process, a peak capacity having a value greater than or equal to 50. In some embodiments, the separation capillary tube comprises, during its operation as a component of a sheathless interface of a CE process, a peak capacity having a value greater than or equal to 200. In some embodiments, the separation capillary tube comprises, during its operation as a component of a sheathless interface of a CE process, a peak capacity having a value greater than or equal to 400. Peak capacity is a measure of the number of peaks that are separable from one another during a CE-ESI-MS process.

In some embodiments, the separation capillary tube that is useful as a sheathless interface for coupling a CE process and an ESI-MS process comprises, during its operation as a component of a sheathless interface of a CE process, a capillary run life having a value that is greater than or equal to 75 runs. In some embodiments, the separation capillary tube comprises, during its operation as a component of a sheathless interface of a CE process, a capillary run life having a value that is greater than or equal to 100 runs. In some embodiments, the separation capillary tube comprises, during its operation as a component of a sheathless interface of a CE process, a capillary run life having a value that is greater than or equal to 300 runs. Capillary run life is the total number of runs during which a separation capillary provides acceptable performance.

In some embodiments, the separation capillary tube that is useful as a sheathless interface for coupling a CE process and an ESI-MS process comprises an inner tube diameter, wherein the inner tube diameter has a value selected from the group consisting of between 5 µm and 10 µm (inclusive), between 5 µm and 15 µm (inclusive), between 5 µm and 20µm (inclusive), between 5 µm and 25 µm (inclusive), between 5 µm and 30 µm (inclusive), between 5 µm and 35 µm (inclusive), between 5 µm and 40 µm (inclusive), between 5 µm and 45 µm (inclusive), between 5 µm and 50 µm (inclusive), between 30 µm and 50 µm (inclusive), between 25 µm and 35 µm (inclusive), and between 15 µm and 45 µm (inclusive).

In some embodiments, the separation capillary tube that is useful as a sheathless interface for coupling a CE process and an ESI-MS process comprises a length, wherein the length has a value selected from the group consisting of between 5 cm and 300 cm (inclusive), between 25 cm and 250 cm (inclusive), between 50 cm and 200 cm (inclusive), between 75 cm and 150 cm (inclusive), and between 100 cm and 125 cm (inclusive). In some embodiments, the separation capillary tube has dimensions including 30 µm inner diameter×150 µm outer diameter. In some embodiments, the separation capillary tube has dimensions including 30 µm inner diameter×360 µm outer diameter.

In some embodiments, the separation capillary tube that is useful as a sheathless interface for coupling a CE process and an ESI-MS process comprises an etched capillary outlet-proximal end portion of a separation capillary tube, wherein the etched capillary outlet-proximal end portion has a length, wherein said length has a value selected from the group consisting of between 5 mm and 100 mm (inclusive), between 10 mm and 90 mm (inclusive), between 15 mm and 85 mm (inclusive), between 20 mm and 80 mm (inclusive), between 25 mm and 75 mm (inclusive), between 30 mm and 70 mm (inclusive), between 35 mm and 65 mm (inclusive), and between 40 mm and 60 mm (inclusive).

Thus, the separation capillary tube that is useful as a sheathless interface for coupling a CE process and an ESI-MS process yields significant performance enhancements such as improved peak capacity and improved sensitivity, which are particularly important for analyzing, inter alia, peptides, proteins, drugs, metabolites, very complex samples that may only be available in minute amounts, or a combination thereof. The innovations herein provide for negligible non-specific interactions during a CE process between an inner wall of a capillary tube (or a coating surface thereof) and analytes (peptides, proteins, drugs, metabolites, and/or very complex samples), thereby allowing separations having improved efficiencies. Moreover, the innovations herein enable integration of very powerful pre-concentration methodologies including, but not limited to, transient isotachphoresis and electrokinetic supercharging.

Uses of the innovations herein include, but are not limited to, characterizing therapeutic proteins; identifying proteins that make up a specific proteome; characterizing post-translational modifications; studying a metabolomic fingerprint related to a particular condition; and quantifying drugs and their metabolites in a minute or complex sample matrix.

While the invention has been described with respect to exemplary embodiments, one skilled in the art will recognize that numerous modifications are possible. For example, the methods and processes described herein in some embodiments are implemented using hardware components, software components, and/or any combination thereof As a further non-limiting example to the embodiments described above, in certain embodiments, adjustments of an x, y, z control as described herein are automated using hardware, software, or a combination thereof Further, while various methods and processes described herein are described in some embodiments with respect to particular structural and/or functional components for ease of description, methods of the invention are not limited to any particular structural and/or functional architecture, but instead can be implemented on any suitable configuration. Similarly, while various functionalities are ascribed to certain system components, unless the context dictates otherwise, this functionality in some embodiments is distributed among various other system components in accordance with different embodiments of the invention.

As described above, potential uses of the innovations presented herein include, but are not limited to, analysis of protein complexes, proteins, peptides, glycans or drugs/metabolites using CE and characterization/identification of the resulting separated molecules using MS. Additionally, in some embodiments the innovations herein are used with molecular analysis, protein analysis, carbohydrate analysis, glycoprotein analysis, small molecule analysis, chiral analysis, ion analysis, drug analysis, and genetic analysis. Genetic analysis includes DNA sequencing, genotyping, single nucleotide polymorphism (SNP) analysis, short tandem repeat (STR) analysis, DNA fingerprinting analysis, nucleic acid analysis, genotyping analysis, oligonucleotide purity analysis, plasmid analysis, single-stranded conformational polymorphism (SSCP) analysis, and quantification by direct hybridization analysis. Further, this list is not exhaustive and is not limiting, as a person of ordinary skill in the art may recognize additional potential uses for various embodiments according to the innovations described herein.

Moreover, while the procedures comprised in the methods and processes described herein are described in a particular order for ease of description, unless the context dictates otherwise, various procedures may be reordered, added, and/or omitted in accordance with various embodiments of the invention. Moreover, the procedures described with respect to one method or process may be incorporated within other described methods or processes; likewise, system components described according to a particular structural architecture and/or with respect to one system may be organized in alternative structural architectures and/or incorporated within other described systems. Hence, while various embodiments are described with—or without—certain features for ease of description and to illustrate exemplary features, the various components and/or features described herein with respect to a particular embodiment can be substituted, added, and/or subtracted from among other described embodiments, unless the context dictates otherwise. Consequently, although the invention has been described with respect to exemplary embodiments, it will be appreciated that the invention is intended to cover all modifications and equivalents within the scope of the following claims.

Thus, according to various embodiments there are described various embodiments including but not limited to the embodiments below. There is described, for example, an electrical circuit comprising a first dc power supply having a first output and a first input; a first resistive electrical path connected to a ground that provides a first dc power supply return from the first output to the first input; a second dc power supply having a second output and a second input; a second resistive electrical path that provides a second dc power supply return from the second output to the second input, wherein the second resistive electrical path is isolated from the ground, and wherein the first output is electrically coupled with the second input; an isolated control circuit that is electrically coupled with the second dc power supply and is isolated from the ground, wherein the isolated control circuit is communicatively coupled with an interface board via a communication link, and wherein the communication link maintains isolation from the ground; and a DC/DC converter that provides isolated input power to the second dc power supply and the isolated control circuit.

There is also described an electrical circuit of wherein the second resistive electrical path is electrically coupled to an electro-spray (ES) assembly. There is also described an electrical circuit wherein the ES assembly is electrically coupled to an adapter, and wherein the ES assembly comprises a sprayer housing, and wherein the sprayer housing comprises a needle, a spring wound around the needle, a retracting protective sheath coupled to the spring. There is also described an electrical circuit wherein the ES assembly is coupled to a mass spectrometer via the adapter. There is also described an electrical circuit wherein the ES assembly comprises a conductive slug portion that provides a resistive electrical ES assembly path from an external surface of the ES assembly to a conductive fluid contact area inside the ES assembly; and wherein the second resistive electrical path comprises the resistive electrical ES assembly path.

There is also described an electrical circuit wherein the second resistive electrical path further comprises a resistive electrical adapter path as part of an adapter that couples the ES assembly to a mass spectrometer. There is also described an electrical circuit wherein the first output is electrically coupled with the second input via the resistive electrical ES assembly path. There is also described an electrical circuit wherein the first resistive electrical path comprises a conductive fluid capillary path that is part of a capillary electrophoresis (CE) analysis system. There is also described an electrical circuit wherein the interface board is part of the CE analysis system, and wherein the CE analysis system communicates with the isolated control circuit via the interface board to control the second DC power supply. There is also described an electrical circuit wherein the interface board is part of the CE analysis system; wherein the communications link is an optical communications link; wherein the interface board receives an analog control signal, converts the analog control signal to a digital logic pulse stream which is routed to the isolated control circuit; and wherein the isolated control circuit converts the digital logic pulse stream back into the analog control signal and controls the second DC power supply using the analog control signal.

There is also described an electrical circuit further comprising a voltage limit resistor coupled directly with the first dc power supply, wherein said voltage limit resistor is in the first resistive electrical path and is not in the second resistive electrical path. There is also described an electrical circuit wherein the communication link and the DC/DC converter each is able to withstand a voltage greater than or equal to a maximum output voltage of the first dc power supply, a maximum output voltage of the second dc power supply, or a voltage that is a sum of said maximum output voltages. There is also described an electrical circuit wherein the maximum output voltage of the first dc power supply is a value between −0 kV and +10 kV, inclusive. There is also described an electrical circuit wherein the maximum output voltage of the second dc power supply is a value between −30 kV and +30 kV, inclusive. There is also described an electrical circuit wherein the voltage limit resistor has a resistive value between 10 megaOhms and 500 megaOhms, inclusive. There is also described an electrical circuit further comprising a leakage detection circuit operably coupled with the voltage limit resistor that measures leakage current. There is also described an electrical circuit wherein the leakage detection circuit comprises: a sense resistor coupled directly to the voltage limit resistor; and an amplifier coupled with the sense resistor and the voltage limit resistor; wherein the sense resistor and the amplifier are disposed in the first resistive electrical path and are not disposed in the second resistive electrical path.

There is also described an electrical circuit wherein the leakage detection circuit comprises: a sense resistor coupled indirectly with the voltage limit resistor; and an amplifier coupled directly with the sense resistor, wherein the amplifier is indirectly coupled with a first side of the voltage limit resistor via the first DC power supply and is indirectly coupled with a second side of the voltage limit resistor via a mass spectrometer load and the sense resistor; and wherein the sense resistor and the amplifier are disposed in the first resistive electrical path and are not disposed in the second resistive electrical path.

There is also described an electrical circuit wherein the resistive value of the sense resistor is a value between 1 kOhm and 503 kOhms, inclusive. There is also described a cartridge assembly comprising: a cartridge including a housing; a protective sheath configured to be coupled with the cartridge; a capillary coupled with the protective sheath, wherein the capillary and the protective sheath are disposed to move with respect to one another between a first position and a second position, wherein an end portion of the capillary is protected in the first position and wherein the end portion of the capillary is operably disposed in the second position.

There is also described a cartridge assembly wherein the protective sheath is a first protective sheath, the capillary is a first capillary, and wherein the cartridge assembly comprises a second protective sheath and a second capillary. There is also described a cartridge assembly, wherein the second capillary and the second protective sheath are disposed to move with respect to one another between a third position and a fourth position, wherein an end portion of the second capillary is protected in the third position and wherein the end portion of the second capillary is operably disposed in the fourth position.

There is also described a cartridge assembly further comprising first and second cooling tubes respectively surrounding the first and second capillaries, wherein the first and second cooling tubes are configured to contain a cooling fluid. There is also described a cartridge assembly wherein the cooling fluid circulates in the first and second tubes in a cooling circuit. There is also described a cartridge assembly further comprising a seal between the capillary and the housing. There is also described a cartridge assembly wherein the protective sheath comprises a capillary interface, wherein the capillary interface is configured to receive the seal. There is also described a cartridge assembly wherein the housing of the cartridge comprises a window which exposes at least a portion of the capillary. There is also described a cartridge assembly further comprising a sprayer housing coupled with the capillary. There is also described a cartridge assembly wherein the protective sheath is a first protective sheath, and wherein the cartridge assembly further comprises a sprayer housing coupled with the capillary, wherein the sprayer housing includes a third protective sheath and a capillary output-proximal end portion of the capillary, the third protective sheath surrounding at least a portion of the capillary output-proximal end portion of the capillary.

There is also described a cartridge assembly wherein the third protective sheath is retractable; wherein the capillary and the third protective sheath are disposed to move with respect to one another between a fifth position and a sixth position as the third protective sheath retracts, wherein the capillary output-proximal end portion of the capillary is protected in the fifth position and wherein the capillary output-proximal end portion of the capillary is operably disposed in the sixth position, such that the third protective sheath guides the output-proximal end portion of the capillary to the sixth position.

There is also described a cartridge assembly wherein the sprayer housing further comprises a spring coupled to the third protective sheath and a body of the sprayer housing such that the spring compresses when the third protective sheath is retracted, and the spring exerts a force to extend the third protective sheath.

There is also described a cartridge assembly further comprising a needle disposed within the sprayer housing, the needle surrounding a portion of the first capillary such that the first capillary extends through the needle; wherein coils of the spring surround at least a portion of the needle. There is also described a cartridge assembly wherein the third protective sheath further comprises at least one retention finger that locks into a first area of the sprayer housing when the third protective sheath is in an extended position to prevent the third protective sheath from further extending away from the sprayer housing.

There is also described a cartridge assembly wherein the protective sheath comprises a tapered guide pass through in an end portion of the protective sheath, the tapered guide pass through being tapered such that an anterior portion of the tapered guide pass through that is proximal to the capillary is wider than an exterior portion of the guide pass through that is distal to the capillary, the tapered guide pass through positioned such that when the protective sheath is in the first position, the capillary is within the protective sheath and as the protective sheath moves to the second position, the end portion of the capillary passes through the tapered guide pass through to a position exterior to the protective sheath in the second position. There is also described a cartridge assembly further comprising a sprayer housing coupled with the capillary, wherein the sprayer housing comprises a double lumen tube, a coolant manifold, and a ferrule, wherein the ferrule is disposed to deform a portion of the double lumen tube.

There is also described a cartridge assembly further comprising a sprayer housing coupled with the capillary, wherein the sprayer housing comprises a first electrical contact configured to contact a second electrical contact on an adapter. There is also described a cartridge assembly, wherein the adapter is selected from the group consisting of at least a first adapter cooperatively configured with a first MS system, a second adapter cooperatively configured with a second MS system, and a third adapter cooperatively configured with a third MS system, wherein said at least first, second, and third adapters are cooperatively configured with said sprayer housing. There is also described a cartridge assembly wherein the cartridge comprises a flexible finger detent; and the protective sheath comprises a mechanical stop; and wherein with the capillary and the protective sheath in the first position, the flexible finger detent and the mechanical stop interface to prevent movement of the protective sheath to the second position, thereby disposing the protective sheath in a locked position, unless the flexible finger detent is flexed about a pivot point. There is also described a cartridge assembly further comprising: means for locking the protective sheath in the first position.

There is also described a cartridge assembly, wherein the protective sheath protects and guides an end portion of the capillary during its insertion into, or removal from, an interface block of a capillary electrophoresis system. There is also described a cartridge assembly, wherein the third protective sheath protects and guides the at least a portion of the capillary output-proximal end portion of the capillary, which is optionally etched, during its insertion into, or removal from, a mass spectrometry system.

There is also described an adapter, wherein said adapter is a part of a capillary electrophoresis electrospray ionization mass spectrometry (CE-ESI-MS) system that adapts an electrospray housing containing an end portion of a separation capillary to an input of a mass spectrometer of the CE-ESI-MS system, and wherein said adapter comprises: an inner surface; and an outer surface; and a first input comprising a first input opening and a first portion of the inner surface; and a first output, wherein an axial capillary passageway extends from the first input to the first output, the axial capillary passageway surrounded by at least a second portion of the inner surface; and a high voltage resistive path that extends from a first electrical contact on the outer surface to a second electrical contact on a section of the first portion of the inner surface. There is also described an adapter, wherein the first portion of the inner surface comprises a hooked groove. There is also described an adapter further comprising a plurality of screws extending from the outer surface to the first portion of the inner surface. There is also described an adapter, wherein the outer surface comprises a first portion of the outer surface that is structured to interface with a mass spectrometer input.

There is also described an adapter wherein the outer surface comprises a plurality of adjustment contact points coupled to an x, y, z adjustment control, the x, y, z adjustment control comprising a means for fine adjustments to the position and orientation of the first output. There is also described an adapter wherein the inner surface comprises: a means for interfacing with a retractable capillary sheath that is part of a sprayer housing; and a means for securing at least a first portion of the sprayer housing within a first portion of the axial capillary passageway.

What is claimed is:
1. A cartridge assembly comprising:
a cartridge:
a first protective sheath configured to be moveably coupled with the cartridge;
a first capillary disposed inside the first protective sheath, wherein the first capillary and the first protective sheath are disposed to move with respect to one another between a first position and a second position,
wherein an end portion of the first capillary is protected in the first position and wherein the end portion of the first capillary is operably disposed in the second position;
the cartridge assembly further comprising a second protective sheath moveably coupled with the cartridge and a second capillary, wherein the second capillary and the second protective sheath are disposed to move with respect to one another between a third position and a fourth position, wherein a first end portion of the second capillary is protected in the third position and wherein the first end portion of the second capillary is operably disposed in the fourth position;
the cartridge assembly further comprising a sprayer housing coupled with the first and second capillaries, wherein the sprayer housing comprises a double lumen tube, a coolant manifold, a ferrule, an electrically conductive slug having a cylindrical inner surface, and an electrospray ionization tip;
the cartridge assembly further comprising first and second cooling tubes respectively surrounding middle portions of the first and second capillaries;
the first and second capillaries and associated first and second cooling tubes extending into the coolant manifold and configured such that the first and second cooling tubes can contain a cooling fluid and where the coolant can divert from the first cooling tube to the second cooling tube;
the first and second capillaries extending further from the coolant manifold into first and second lumens, respectively, of the double lumen tube, the first capillary extending through the double lumen tube to the electrospray ionization tip; and wherein the ferrule deforms the double lumen tube at a position that prevents leakage of the coolant from the coolant manifold beyond a region between the deformed position of the double lumen tube and the electrospray ionization tip; and
wherein the electrically conductive slug surrounds the first capillary and a second end of the second capillary opens into a region between the cylindrical inner surface of the conductive slug and the first capillary.

2. The cartridge assembly of claim 1 wherein the cooling fluid circulates in the first and second cooling tubes in a cooling circuit.

3. The cartridge assembly of claim 1 further comprising a seal between the first and second capillaries and the cartridge.

4. The cartridge assembly of claim 3 wherein the first and second protective sheaths comprises a capillary interface, wherein the capillary interface is configured to receive the seal.

5. The cartridge assembly of claim 1 wherein the first protective sheath comprises a tapered guide pass through in an end portion of the first protective sheath, the tapered guide pass through being tapered such that an anterior portion of the tapered guide pass through that is proximal to the first capillary is wider than an exterior portion of the guide pass through that is distal to the first capillary, the tapered guide pass through positioned such that when the first protective sheath is in the first position, the capillary is within the first protective sheath and as the first protective sheath moves to the second position, the end portion of the first capillary passes through the tapered guide pass through to a position exterior to the first protective sheath in the second position.

6. The cartridge assembly of claim 1 wherein the sprayer housing also comprises a first electrical contact configured to contact a second electrical contact on an adapter, said adapter being cooperatively configured with an MS system and with said sprayer housing.

7. The cartridge assembly of claim 1 wherein the cartridge comprises a window which exposes at least a portion of the first or second capillary.

8. The cartridge assembly of claim 1 wherein the cartridge comprises a flexible finger detent; and
the first protective sheath comprises a mechanical stop; and
wherein with the first capillary and the first protective sheath are in the first position, the flexible finger detent and the mechanical stop interface to prevent movement of the protective sheath to the second position, thereby disposing the first protective sheath in a locked position, unless the flexible finger detent is flexed about a pivot point.

9. The cartridge assembly of claim 1 wherein the cartridge assembly further comprises means for locking the first protective sheath in the first position.

10. The cartridge assembly of claim 1 wherein the first and second protective sheaths protects and guides the end portion of the first capillary and the first end of the second capillary during their insertion into, or removal from, an interface block of a capillary electrophoresis system.

11. The cartridge assembly of claim 1 wherein the sprayer housing further comprises a third protective sheath and a capillary output-proximal end portion of the first capillary, the third protective sheath surrounding at least a portion of the capillary output-proximal end portion of the first capillary.

12. The cartridge assembly of claim 11 wherein the third protective sheath is retractable;

wherein the first capillary and the third protective sheath are disposed to move with respect to one another between a fifth position and a sixth position as the third protective sheath retracts, wherein the capillary output-proximal end portion of the first capillary is protected in the fifth position and wherein the capillary output-proximal end portion of the first capillary is operably disposed in the sixth position, such that the third protective sheath guides the output-proximal end portion of the capillary to the sixth position.

13. The cartridge assembly of claim 12 wherein the sprayer housing further comprises a spring coupled to the third protective sheath and a body of the sprayer housing such that the spring compresses when the third protective sheath is retracted, and the spring exerts a force to extend the third protective sheath.

14. The cartridge assembly of claim 13 further comprising a needle disposed within the sprayer housing, the needle surrounding a portion of the first capillary such that the first capillary extends through the needle;

wherein coils of the spring surround at least a portion of the needle.

15. The cartridge assembly of claim 12, wherein the third protective sheath protects and guides the at least a portion of the capillary output-proximal end portion of the first capillary, which is etched, during its insertion into, or removal from, a mass spectrometry system.

16. The cartridge assembly of claim 1 wherein the first capillary is etched and has a coating layer that comprises a hydrophilic bifunctional compound covalently bound to a surface of the first capillary wherein the hydrophilic bifunctional compound selected from the group consisting of γ-methacryloxypropyltrimethoxysilane, β-methacryloxypropyltrimethoxysilane, α-methacryloxypropyltrimethoxysilane, (3-glycidyloxypropyl) trimethoxysilane, 3-(trimethoxysilyl)propyl acrylate, 3-(trimethoxysilyl)propyl methacrylate, vinyltrimethoxysilane, vinyltriacetoxysilane, vinyltri(β-methoxyethoxy)silane, and vinyltrichlorosilane.

17. The cartridge assembly of claim 1 wherein the first capillary has a coating layer that comprises a neutral surface that comprises cross-linked linear polyacrylamide.

18. The cartridge assembly of claim 17 wherein the neutral surface comprises cross-linked linear polyacrylamide that is covalently bound with a hydrophilic bifunctional compound that is covalently bound to a surface of the first capillary wherein the hydrophilic bifunctional compound selected from the group consisting of γ-methacryloxypropyltrimethoxysilane, β-methacryloxypropyitrimethoxysilane, α-methacryloxypropyltrimethoxysilane, (3-glycidyloxypropyl) trimethoxysilane, 3-(trimethoxysilyl)propyl acrylate, 3-(trimethoxysilyl)propyl methacrylate, vinyltrimethoxysilane, vinyltriacetoxysilane, vinyltri(β-methoxyethoxy)silane, and vinyltrichlorosilane.

19. The cartridge assembly of claim 1 wherein, the electrically conductive slug is electrically connected to an electrical circuit comprising:

a first dc power supply having a first output and a first input:

a first resistive electrical path connected to a ground that provides a first de power supply return from the first output to the first input;

a second dc power supply having a second output and a second input;

a second resistive electrical path that provides a second dc power supply return from the second output to the second input, wherein the second resistive electrical path is isolated from the ground, and wherein the first output is electrically coupled with the second input;

an isolated control circuit that is electrically coupled with the second dc power supply and is isolated from the ground, wherein the isolated control circuit is communicatively coupled with an interface board via a communication link, and wherein the communication link maintains isolation from the ground; and a DC/DC converter that provides isolated input power to the second dc power supply and the isolated control.

* * * * *